US011771693B2

(12) United States Patent
Iorio

(10) Patent No.: US 11,771,693 B2
(45) Date of Patent: Oct. 3, 2023

(54) DEVICE FOR DETERRING ABUSE OF DRUGS

(71) Applicant: EIGHTY EIGHT PHARMA, INC., Mansfield, MA (US)

(72) Inventor: Matthew Iorio, Foxboro, MA (US)

(73) Assignee: Eighty Eight Pharma, Inc., Foxboro, MA (US)

( * ) Notice: Subject to any disclaimer, the term of this patent is extended or adjusted under 35 U.S.C. 154(b) by 434 days.

(21) Appl. No.: 16/860,551

(22) Filed: Apr. 28, 2020

(65) Prior Publication Data
US 2020/0345721 A1 Nov. 5, 2020

Related U.S. Application Data

(60) Provisional application No. 62/940,299, filed on Nov. 26, 2019, provisional application No. 62/883,224, filed on Aug. 6, 2019, provisional application No. 62/841,370, filed on May 1, 2019.

(51) Int. Cl.
| | |
|---|---|
| *A61K 31/485* | (2006.01) |
| *A61J 1/14* | (2023.01) |
| *A61K 47/38* | (2006.01) |
| *A61K 47/12* | (2006.01) |
| *A61J 1/03* | (2023.01) |
| *A61J 7/04* | (2006.01) |
| *A61M 5/50* | (2006.01) |
| *A61M 39/10* | (2006.01) |

(52) U.S. Cl.
CPC ........... *A61K 31/485* (2013.01); *A61J 1/03* (2013.01); *A61J 1/1437* (2013.01); *A61J 7/0445* (2015.05); *A61K 47/12* (2013.01); *A61K 47/38* (2013.01); *A61M 5/5086* (2013.01); *A61M 39/1011* (2013.01)

(58) Field of Classification Search
CPC ......... A61J 1/1437; A61J 1/03; A61J 7/0445; A61J 7/0427; A61M 5/5086; A61M 39/1011
See application file for complete search history.

(56) References Cited

U.S. PATENT DOCUMENTS

| | | | | |
|---|---|---|---|---|
| 9,913,778 B2* | 3/2018 | Dvorak | ................ | A61J 7/0084 |
| 2007/0023444 A1* | 2/2007 | Holloway | ............... | G07F 11/44 |
| | | | | 221/7 |
| 2011/0226817 A1* | 9/2011 | Ortenzi | ..................... | A61J 1/18 |
| | | | | 222/424.5 |
| 2014/0278510 A1* | 9/2014 | McLean | ................ | G16H 20/13 |
| | | | | 705/2 |
| 2015/0278479 A1* | 10/2015 | Ervin | ........................ | A61J 1/03 |
| | | | | 700/237 |
| 2017/0079887 A1* | 3/2017 | Song | ........................ | A61J 1/03 |

* cited by examiner

*Primary Examiner* — Ariana Zimbouski
(74) *Attorney, Agent, or Firm* — McDonnell Boehnen Hulbert & Berghoff LLP

(57) ABSTRACT

The present disclosure relates to devices for deterring drug abuse and methods thereof. More particularly, the disclosure relates to devices for deterring drug abuse by using physical deterrents and/or deterrent substances, including a mechanism that releases a deterrent substance when improper access of the drug is attempted, and methods thereof.

8 Claims, 30 Drawing Sheets

Section view B-B

Section view B-B

Section view D-D

DEVICE FOR DETERRING ABUSE OF DRUGS

CROSS-REFERENCE TO RELATED APPLICATIONS

This patent application claims priority from U.S. Provisional Application No. 62/940,299 filed on Nov. 26, 2019, U.S. Provisional Application No. 62/883,224, filed on Aug. 6, 2019, and U.S. Provisional Application No. 62/841,370, filed on May 1, 2019, and are herein incorporated by reference in their entireties.

FIELD OF THE INVENTION

The present disclosure generally relates to devices for deterring drug abuse and methods thereof. More particularly, the disclosure relates to devices for deterring drug abuse by using physical deterrents and/or deterrent substances, including a mechanism that dispenses a deterrent substance before the drug can be improperly accessed. The present disclosure also relates to methods of accessing a drug from such devices.

BACKGROUND OF THE INVENTION

The opioid crisis has greatly increased the risk of medication diversion, i.e., when a legal controlled substance is used illegally. The drug theft occurs frequently in outpatient facilities, but may happen anywhere. The theft may come from a number of sources including the patient, friends and family of the patient, and even health care workers struggling with addition. Stealing medication from an IV line or a syringe and replacing it with another substance to prevent detection may lead to dangerous bloodstream infections.

SUMMARY OF THE INVENTION

It is against the above background that the disclosure provides certain advantages and advancements over the prior art. Although the disclosure herein is not limited to specific advantages or functionality, the invention disclosed herein provides devices and methods for deterring drug abuse.

In one aspect, the disclosure is a composition comprising a formulation comprising naltrexone hydrochloride ("HCl") in a solution comprising ethanol and water.

In some embodiments of the formulation, the naltrexone HCl is dissolved in the solution at a concentration of 23 mg/ml. In some embodiments of the formulation, the naltrexone HCl is dissolved in the solution at a concentration of 37 mg/ml.

In some embodiments of the disclosure, the composition further comprises one or more of: (a) a colorant; (b) a thickening or gelling agent; or (c) a foul odor. In some embodiments, the colorant is D&C Red No. 33, FD&C Red No. 40, FD&C Green No. 3, D&C Violet No. 2 or Vitamin B12, the thickening or gelling agent is hyroxypropyl cellulose, and the foul odor is butyric acid.

In another aspect, the disclosure comprises a method for deterring drug abuse comprising contacting an opioid drug dose with a composition comprising a formulation comprising naltrexone HCl in a solution comprising ethanol and water for a suitable amount of time to compromise the integrity of the drug dosage. In some embodiments, the physical integrity of the opioid drug dose is compromised before or simultaneously with contacting the drug dose with the formulation of claim 1.

In some embodiments, the opioid drug dose comprises: an immediate release tablet, caplet or capsule; an extended release tablet, caplet or capsule; a liquid formulation for oral consumption; a liquid formulation for IV injection; a syrup or liquid concentrate; a pharmaceutical film; or an orally dissolving tablet.

In some embodiments, the drug dosage is contacted with the composition comprising a formulation comprising naltrexone HCl in a solution comprising ethanol and water for between 2 minutes and 24 hours. In some embodiments, the drug dosage is contacted with the composition for between 0 and 10 seconds.

In another aspect, the disclosure comprises a device for deterring drug abuse, the device comprising:

a housing configured to contain a drug that may be accessed through an access port located on a lid attached to the housing;

a rotatable portion of the housing or the lid which is capable of rotating a carousel or rotating relative to the carousel when in an unsecured position;

a locking mechanism coupled with the rotatable portion of the housing or the lid, the locking mechanism having a locked mode, wherein the rotatable portion of the housing or the lid is not normally able to move from the secure position;

the locking mechanism further coupled with a piston;

the device being configured such that attempts to improperly access the drug:

a) when the rotatable portion of the housing or the lid is in the secure position, and b) when the locking mechanism is in the locked mode, move the piston and activate the release of the deterrent substance to the drug.

In some embodiments, the deterrent substance comprises one or more of a drug antagonist, a chemical irritant, a gelling agent, a colorant, an emetic, or an encapsulating agent.

In some embodiments, the locking mechanism is coupled to a timer, the locking mechanism locking after a predefined time.

In some embodiments, the locking mechanism is coupled to a dosage counter, the locking mechanism locking after a predefined dosage has been released from the housing.

In some embodiments, the device further comprises a physical deterrent that is part of the housing. In some embodiments, the device further comprises a physical deterrent that is external to the housing.

In some embodiments, cutting a wall of the housing activates the piston, crushing the drug and releasing the deterrent substance into the space holding the drug.

In some embodiments, the housing has hollow walls under negative pressure.

In another aspect, the disclosure comprises a method of accessing a drug provided inside a housing having a physical deterrent and a chemical deterrent, the method comprising:

providing:

a housing configured to contain a carousel wherein a drug is stored, a lid attached to the housing, the lid having an access port through which the drug may be accessed, a physical deterrent that prevents rotation of the carousel or rotation of a lid relative to the carousel, and blocks access to the access port when the physical deterrent is in a secure position, a locking mechanism that prevents and/or significantly hinders the physical deterrent from moving from the secure position to an unsecured position, wherein the physical deterrent no longer blocks access to the access port when in the unsecured position, and a chemical deterrent substance located in the carousel that is released when the drug is accessed while the physical deterrent is in the secure position and the locking mechanism is in the locked mode;

unlocking the locking mechanism;

moving the physical deterrent into the unsecure position; and accessing the drug.

In another aspect, the disclosure comprises a device for a fixed quantity unit of a drug, the device comprising: a carousel comprising: (i) a drug within one or more spaces; (ii) a piston adjacent to each space; (iii) a chemical deterrent substance within the piston; and (iv) a trigger attached to the carousel, wherein the trigger is capable of activating the release of the chemical deterrent substance onto the drug. In some embodiments, the device is disposable.

In some embodiments, the device further comprises one or more of: a pharmaceutical foil which covers the top of the carousel; or a cover comprising cutouts to enable access to each space capable of holding the drug, wherein the cover attaches to the carousel.

In some embodiments, the device further comprises a protective case, wherein the device may be inserted into the protective case.

In some embodiments, the device further comprising a child-resistant cap comprising:

a lower piece comprising a tubular projection in the center, and ridges, teeth, slots or grooves on the top surface, wherein the tubular projection is striated and the tubular projection is inserted into and attaches to the center of the carousel;

an upper piece comprising a tubular projection in the center, and raised ridges or teeth on the bottom surface, wherein the tubular projection of the upper piece is inserted into and attaches to the tubular projection of the lower piece; and two or more access ports in the lower piece and the upper piece, wherein the upper piece and lower piece each include one access port through which a dose of medication may be dispensed and one access port that enables manual activation of the trigger;

wherein a dose of medication may be accessed by depressing the top of the upper piece of the child-resistant cap, which causes the upper piece to contact the lower piece, and turning the cap clockwise or counter-clockwise to the next available dose.

In some embodiments, the device further comprises: a housing comprising a physical deterrent configured to encase the carousel, wherein the housing is under negative pressure; a positioner, wherein the positioner is attached to the housing and is located between the housing and the carousel; and a lid, wherein the lid contains an access port for accessing the drug.

In some embodiments, the housing is fluidly connected to one or more of the carousel, the positioner, or the lid such that a reduction in or release of the negative pressure in the housing activates the pistons and releases the chemical deterrent substance to each space in the carousel.

In another aspect, the disclosure comprises a method of loading a drug into a carousel, the method comprising: providing the carousel configured to comprise: (i) a drug within one or more spaces; (ii) a piston adjacent to each space; (iii) a chemical deterrent substance within the piston; and (iv) a trigger, wherein the trigger is capable of activating the release of the chemical deterrent substance onto the drug; and inserting the drug into the appropriate number of spaces in the carousel.

In some embodiments, the method further comprises one or more of: covering the top of the carousel with pharmaceutical foil; or attaching a cover to the carousel, the cover comprising cutouts to enable access to each space capable of holding the drug.

In some embodiments, the method further comprises: providing: (i) a housing comprising a physical deterrent configured to encase the carousel; and (ii) a lid which contains an access port for accessing the drug; inserting the filled carousel into the housing; attaching the lid to the housing; and placing the housing under negative pressure through the valve.

In some embodiments, the piston is capable of compromising the physical integrity of the drug when activated.

In another aspect, the disclosure comprises a device for a fixed quantity unit of a drug, the device comprising a carousel comprising: (i) a drug within one or more spaces; (ii) threading on the outer surface of the carousel; (iii) a child-resistant cap comprising: a first piece comprising a tubular projection in the center, wherein the tubular projection is inserted into and attaches to the center of the carousel, wherein the first piece has one or more access ports for accessing one or more doses of medication; a second piece comprising a sealing surface or liner; a third piece comprising ridges, teeth, groves or slots on the top surface, and threading on the inner surface of the sides; and a fourth piece comprising raised ridges or teeth on the bottom surface; wherein the third piece is inserted into and attached to the fourth piece, and the combined third and fourth piece is attached to the carousel by the threading on the outer surface of the carousel, and wherein a dose of medication may be accessed by depressing the top of the child-resistant cap and turning in a counter-clockwise direction; (iv) a compartment on the bottom of the carousel that contains a mail-back or disposal bag; and (v) a removable cap which covers the compartment.

In another aspect, the disclosure comprises a method of loading a drug into a carousel, comprising providing the carousel configured to comprise: (i) a drug within one or more spaces; (ii) a piston adjacent to each space; (iii) a chemical deterrent substance within the piston; and (iv) a trigger; wherein the trigger is capable of activating the release of the chemical deterrent substance onto the drug; and inserting the drug into the appropriate number of spaces in the carousel.

In some embodiments, the method further comprises one or more of: covering the top of the carousel with pharmaceutical foil; or attaching a cover to the carousel, the cover comprising cutouts to enable access to each space capable of holding the drug.

In some embodiments, the method further comprises providing: (i) a housing comprising a physical deterrent configured to encase the carousel; and (ii) a lid which contains an access port for accessing the drug; inserting the filled carousel into the housing; attaching the lid to the housing; and placing the housing under negative pressure through the valve.

In some embodiments of the method, the piston is capable of compromising the physical integrity of the drug when activated.

In another aspect, the disclosure comprises a two-piece child-resistant cap comprising: a lower piece comprising: (i)

a tubular projection in the center, wherein the tubular projection is striated; (ii) ridges, teeth, grooves or slots on the top surface of the lower piece; (iii) an access port for dispensing a dose of medication; and (iv) one or more protrusions on the bottom surface, wherein the protrusions are capable of interacting with depressions on a container; an upper piece comprising: (i) a tubular projection in the center, wherein the tubular projection of the upper piece fits inside and attaches to the tubular projection of the lower piece; (ii) raised ridges or teeth on the bottom surface; and (iii) an access port for dispensing a dose of medication, wherein the access port of the upper piece is capable of lining up with the access port of the lower piece, and wherein a dose of medication may be accessed by depressing the top of the upper piece of the child-resistant cap and turning the cap clockwise or counter-clockwise.

In some embodiments, the child-resistant cap further comprises a second access port on the lower piece and the upper piece that are capable of lining up to expose a trigger and enable manual activation of the trigger.

In another aspect, the disclosure comprises a four-piece child-resistant cap comprising:
a first piece comprising:
  (i) a tubular projection in the center;
  (ii) an access port for dispensing a dose of medication; and
  (iii) one or more protrusions on the bottom surface, wherein the protrusions are capable of interacting with depressions on a container;
a second piece comprising a sealing surface or liner;
a third piece comprising:
  (i) threading on the inner surface of the sides;
  (ii) ridges, teeth, grooves or slots on the top surface; and
a fourth piece comprising raised ridges or teeth on the bottom surface;
wherein the third piece is inserted into and attached to the fourth piece, wherein the access port of the lower portion is capable of lining up with a dose of medication, and wherein a dose of medication may be accessed by depressing the top of the fourth piece of the child-resistant cap and turning the cap counter-clockwise.

In some embodiments, the child-resistant cap further comprises a second access port on the first piece that is capable of lining up with and exposing a trigger to enable manual activation of the trigger.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DETAILED DESCRIPTION OF THE INVENTION

Figure 1:
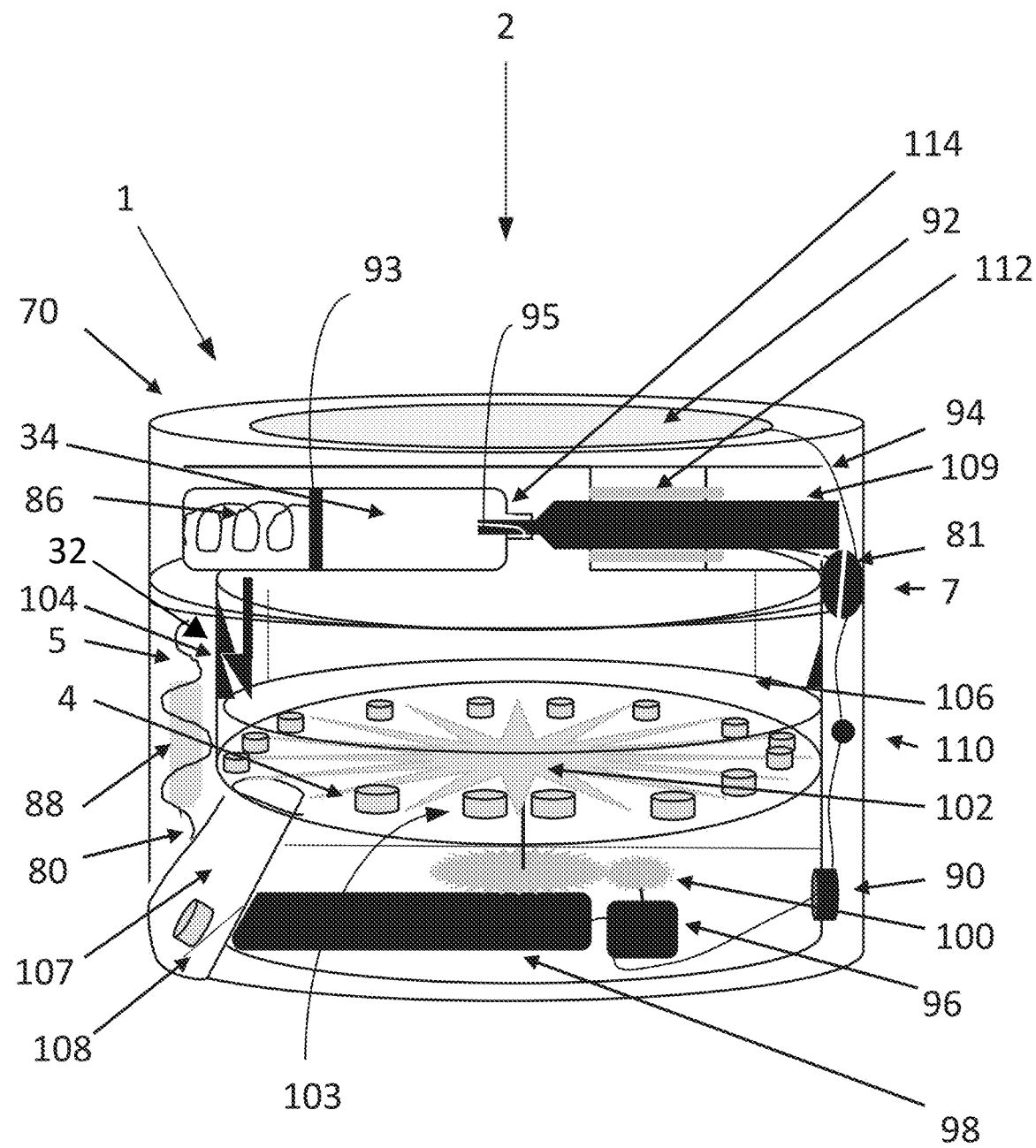
FIG. 1 schematically shows an embodiment of the abuse deterrent device that is built-in to the drug housing in accordance with illustrative embodiments of the invention.
Figure 2:
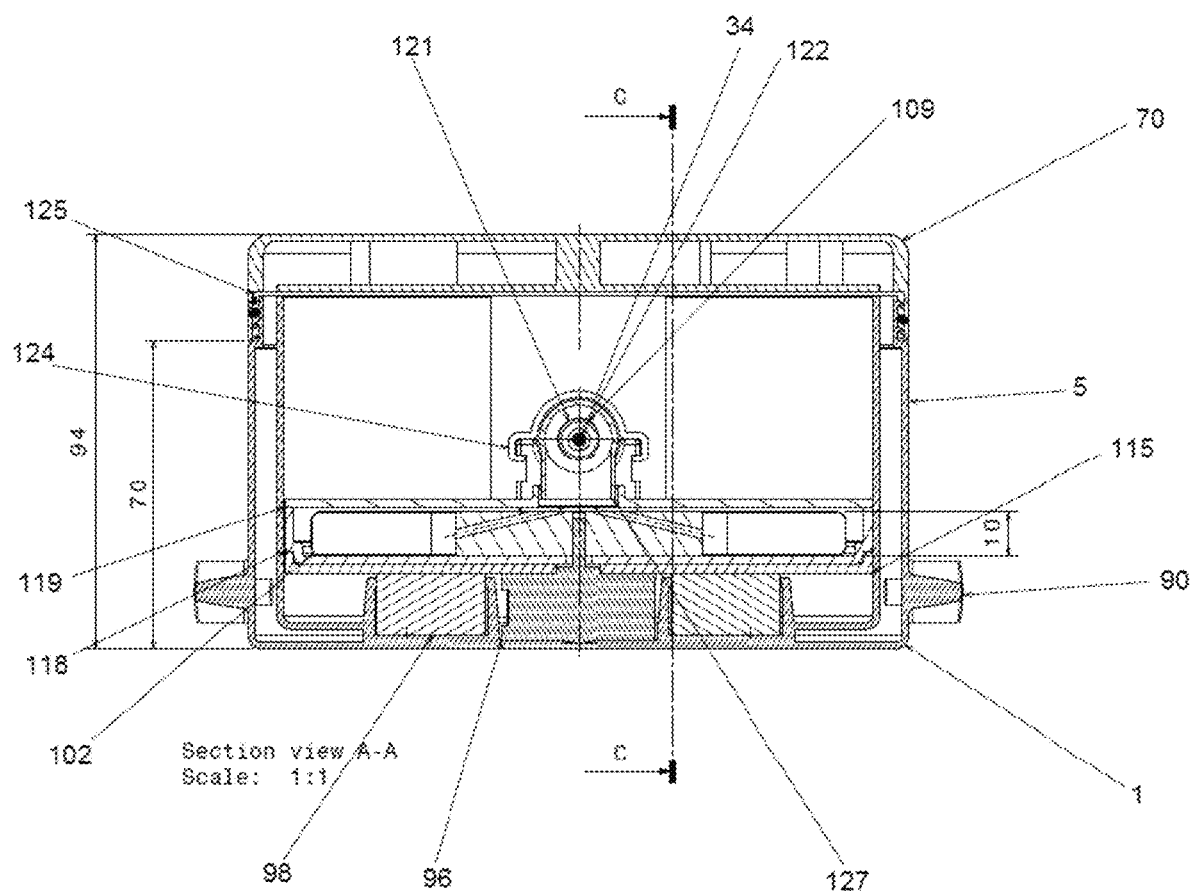
FIG. 2 schematically shows another alternative embodiment of the abuse deterrent device that is built-in to the drug housing in accordance with illustrative embodiments of the invention.
Figure 3:
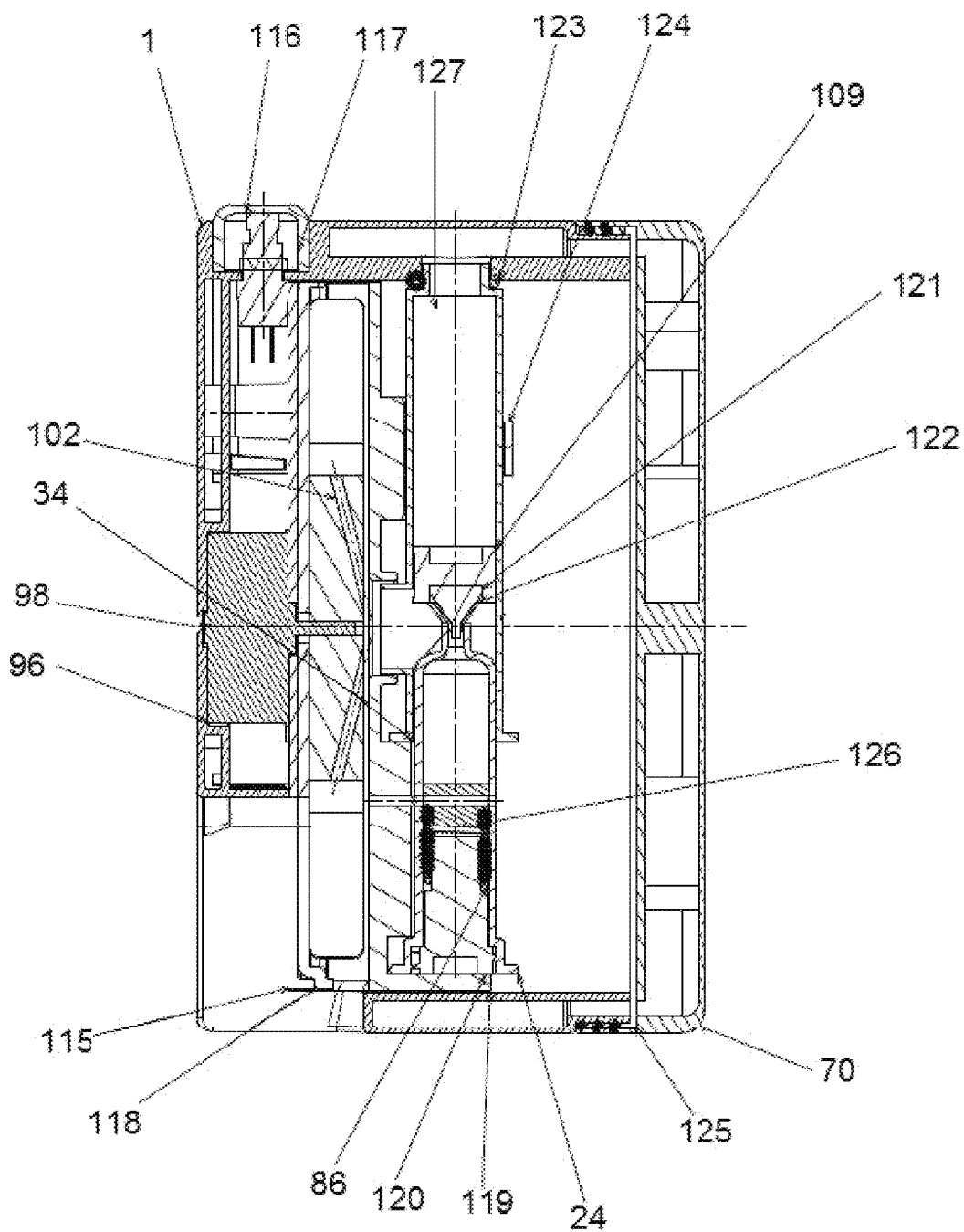
FIG. 3 schematically shows an alternative view of the abuse deterrent device that is built-in to the drug housing in accordance with illustrative embodiments of the invention, as shown in FIG. 2.
Figure 4:
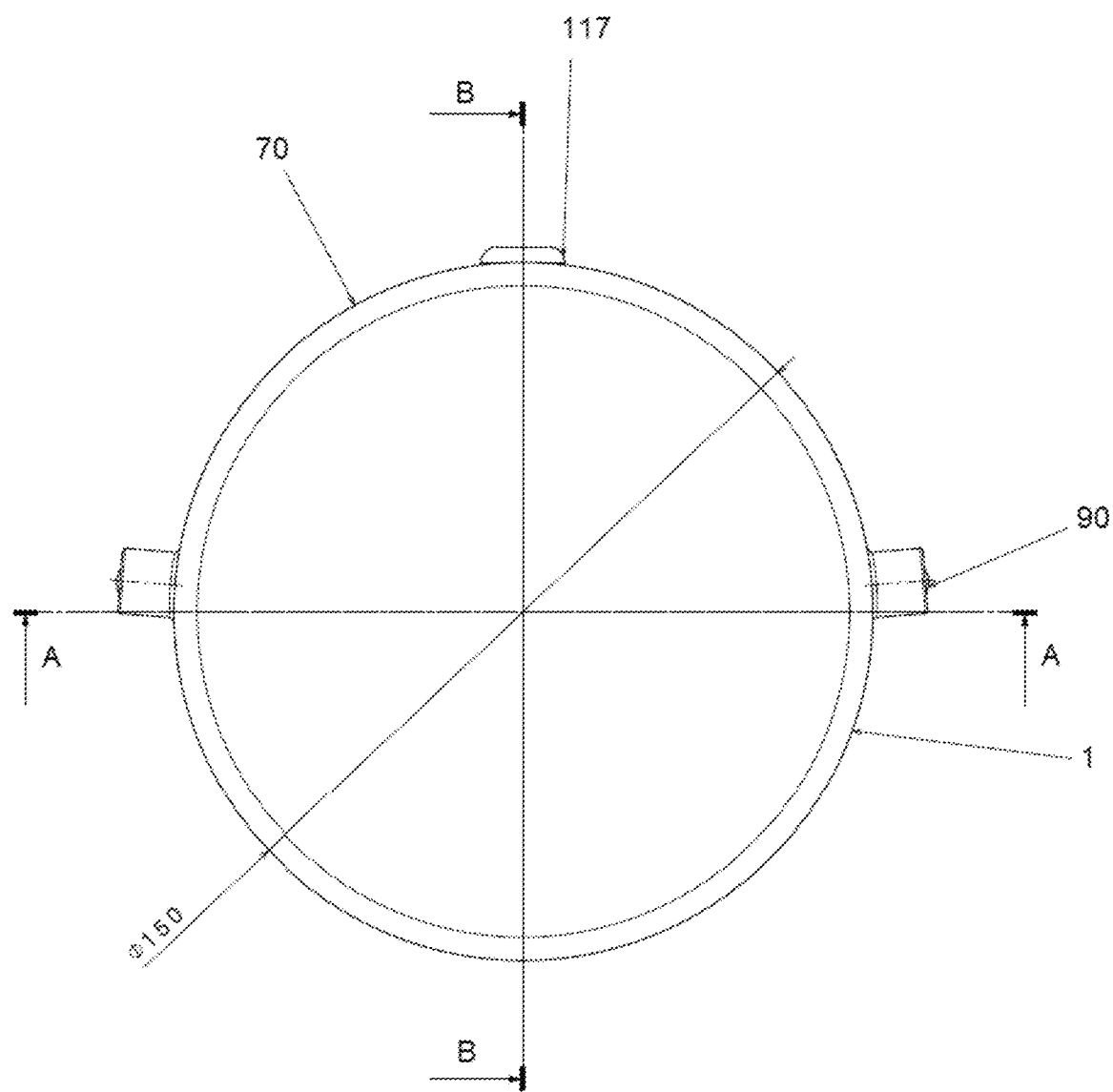
FIG. 4 schematically shows an alternative view of the abuse deterrent device that is built-in to the drug housing in accordance with illustrative embodiments of the invention, as shown in FIGS. 2 and 3.
Figure 5:
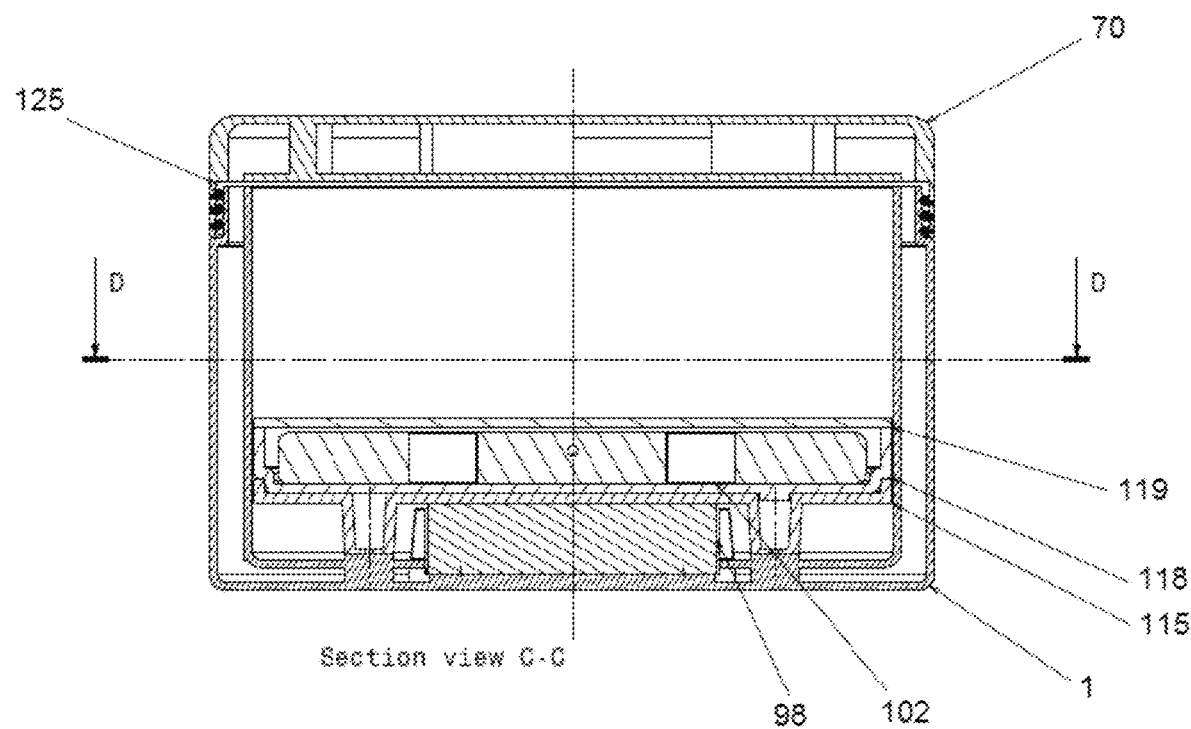
FIG. 5 schematically shows an alternative view of the abuse deterrent device that is built-in to the drug housing in accordance with illustrative embodiments of the invention, as shown in FIGS. 2-4.

Before the disclosed devices and methods are described in detail, it is to be understood that the aspects described herein are not limited to specific embodiments or configurations and, as such, may vary. It is also to be understood that the terminology used herein is for the purpose of describing particular aspects only and, unless specifically defined herein, is not intended to be limiting.

It is also to be understood that, unless clearly indicated otherwise by the context, embodiments disclosed for one aspect or embodiment of the disclosure may be used in other aspects or embodiments as well, and/or in combination with embodiments disclosed in the same or other aspects of the disclosure. Thus, the disclosure is intended to include such combinations, even where such combinations have not been explicitly delineated.

Definitions

Throughout the specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the specification and the appended claims, the singular forms "a," "an" and "the" include plural referents unless the context clearly dictates otherwise.

Values may be expressed herein as approximations by use of the antecedent "about," and it is understood that the particular value forms an aspect. Similarly, ranges may be expressed herein as from "about" one particular value, and/or to "about" another particular value. When such range is expressed, another aspect includes from the one particular value and/or to the other particular value. It will be further understood that the endpoints of each of the ranges are significant both in relation to the other endpoint, and independently of the other endpoint.

As used herein, the term "drug," "medicine," or "medication" includes pharmaceutical medications and pharmaceutical drug products. The pharmaceutical medication or drug may be in liquid, pill, tablet, capsule, gel cap, powder, syrup, concentrate, pharmaceutical film, orally dissolving tablet, or any other form appropriate for any of the devices, containers and methods disclosed herein.

As used herein, the term "deterrent substance" or "chemical deterrent" may be one or more of a drug antagonist (e.g., naloxone, naltrexone, methylnaltrexone, nalmefene, etc.), a colorant (e.g., bright colorant, D&C Red No. 33, FD&C Red No. 40, FD&C Green No. 3, or D&C Violet No. 2, Opadry®, Opacode®, Vitamin B 12), an emetic (e.g., ipecac syrup), a foul odor (e.g., pepsin, butanethiol, butyric acid etc.), a foul tasting agent (e.g., Bitrex® or Denatonium Benzoate), a gelling agent, an encapsulating agent (e.g., glue), a flushing agent (e.g., niacin), and/or an irritant (e.g., capsaicin), each of which are identified as non-limiting examples. Other useful opioid receptor antagonists are known (see e.g., Kreek et al., U.S. Pat. No. 4,987,136). In some embodiments "deterrent substance" refers to an activated carbon disposal pack.

As used herein, the term "deterrent system" includes a mail-back or disposal pouch. In some embodiments where the deterrent system refers to a mail-back pouch, abuse deterrence is achieved by enclosing the medicine in the mail-back pouch and removing the medicine from the patient location to a secure location.

As used herein, the term "piston" includes any material or component that is under tension in its inactive position, and when activated is released to move from an inactive position to an active position. For exemplary purposes only, a piston may include a pressure plate, a disk, a rubber membrane or other membrane of sufficiently rigid material, a balloon or a hammer, comprising any pharmaceutically acceptable material.

As used herein, the terms "rotate," "rotated" or "rotation" include turning, twisting, sliding, pivoting, opening or closing of, for example, a hinge, diaphragm, flap, shutter, etc.

As used herein, the term "tubular projection" refers to an elongated component of any appropriate diameter or length. A tubular projection may be segmented or non-continuous in its circumference, and/or may include ridges or striations of any appropriate size or depth. A tubular projection may include a collar or an open, mushroom-type cap, end, or lip.

As used herein, the term "striated" includes rows, lines, ridges or grooves of any appropriate length, width or depth, which may be used to attach, secure or engage components to, or in contact with, one another.

Formulation of Deterrent Substance

Illustrative embodiments may contain naltrexone as, or as part of, the deterrent substance. Naltrexone (e.g., naltrexone hydrochloride) is an opioid antagonist. Naltrexone markedly attenuates or completely blocks, reversibly, the subjective effects of intravenously administered opioids. Illustrative embodiments can administer a drug antagonist (such as, for example, Naltrexone) that is not associated with the development of tolerance or dependence. Clinical studies indicate that 50 mg of naltrexone hydrochloride blocks the pharmacologic effects of 25 mg of intravenously administered heroin for periods as long as 24 hours. Other data suggest that doubling the dose of naltrexone hydrochloride provides blockade for 48 hours, and tripling the dose of naltrexone hydrochloride provides blockade for about 72 hours. There is limited clinical experience with naltrexone overdosage in humans. In one study, subjects who received 800 mg daily naltrexone hydrochloride for up to one week showed no evidence of toxicity.

In the mouse, rat and guinea pig, the oral LD50s were 1,100 to 1,550 mg/kg; 1,450 mg/kg; and 1,490 mg/kg; respectively. High doses of naltrexone hydrochloride (generally >1,000 mg/kg) produced salivation, depression/reduced activity, tremors, and convulsions. Mortalities in animals due to high-dose naltrexone administration usually were due to tonic-clonic convulsions and/or respiratory failure. Illustrative embodiments of the device 2 may contain between about 10 mg and about 1200 mg of Naltrexone as the chemical deterrent. Some other embodiments may contain a fixed dose of antagonist per unit dose of drug 4 (e.g., opioid). As an example, between 2.5 mg and 30 mg of antagonist may be used per drug dose. Furthermore, illustrative embodiments contain a dosage of chemical deterrent that preferably does not cause over dosage in humans.

In some embodiments, the deterrent substance includes naltrexone base. In embodiments where a formulation of naltrexone base is used as the deterrent substance, formulations including an increased percentage of ethanol to water increases extraction or solubility of the opioid from the drug when the deterrent substance is in contact with the drug. In particular, for opioid agonists with greater solubility in alcohol than water, a deterrent solution with a higher percentage of ethanol is more effective at extracting the opioid agonist from the pill or tablet. In some embodiments, naltrexone base is solubilized in a solution of between about 70% ethanol/30% water and about 40% ethanol/60% water.

In some embodiments, the deterrent substance includes naltrexone hydrochloride ("naltrexone HCl"). In some embodiments, the deterrent substance includes a formulation of naltrexone HCl in a solution of ethanol and water. In some embodiments, the water is purified water. In some embodiments, the ethanol/water is present at a ratio sufficient to prevent freezing of the deterrent substance. In some embodiments, the percentage of ethanol and water is present at a ratio sufficient to reduce or eliminate microbial growth within the deterrent substance. In some embodiments, the formulation containing ethanol and water allows for greater adherence of naltrexone HCl to the drug 4. In some embodiments, the formulation of the deterrent substance extracts or solubilizes the opioid from the drug when the deterrent substance is in contact with the drug. In some embodiments, naltrexone HCl is solubilized in a solution of between about 70% ethanol/30% water and about 20% ethanol/80% water.

In some embodiments, naltrexone HCl is present at a concentration of about 2.5 mg/ml to about 50 mg/ml; e.g., about 2.5 mg/ml to about 45 mg/ml, or about 2.5 mg/ml to about 40 mg/ml, or about 2.5 mg/ml to about 37 mg/ml, or about 2.5 mg/ml to about 35 mg/ml, or about 2.5 mg/ml to about 30 mg/ml, or about 2.5 mg/ml to about 25 mg/ml, or about 2.5 mg/ml to about 20 mg/ml, or about 2.5 mg/ml to about 15 mg/ml, or about 2.5 mg/ml to about 10 mg/ml, or about 2.5 mg/ml to about 5 mg/ml, or about 5 mg/ml to about 45 mg/ml, or about 5 mg/ml to about 40 mg/ml, or about 5 mg/ml to about 37 mg/ml, or about 5 mg/ml to about 35 mg/ml, or about 5 mg/ml to about 30 mg/ml, or about 5 mg/ml to about 25 mg/ml, or about 5 mg/ml to about 20 mg/ml, or about 5 mg/ml to about 15 mg/ml, or about 5 mg/ml to about 10 mg/ml, or about 10 mg/ml to about 45 mg/ml, or about 10 mg/ml to about 40 mg/ml, or about 10 mg/ml to about 37 mg/ml, or about 10 mg/ml to about 35 mg/ml, or about 10 mg/ml to about 30 mg/ml, or about 10 mg/ml to about 25 mg/ml, or about 10 mg/ml to about 20 mg/ml, or about 10 mg/ml to about 15 mg/ml, or about 15 mg/ml to about 45 mg/ml, or about 15 mg/ml to about 40 mg/ml, or about 15 mg/ml to about 37 mg/ml, or about 15 mg/ml to about 35 mg/ml, or about 15 mg/ml to about 30 mg/ml, or about 15 mg/ml to about 25 mg/ml, or about 15 mg/ml to about 20 mg/ml, or about 20 mg/ml to about 45 mg/ml, or about 20 mg/ml to about 40 mg/ml, or about 20 mg/ml to about 37 mg/ml, or about 20 mg/ml to about 35 mg/ml, or about 20 mg/ml to about 30 mg/ml, or about 20 mg/ml to about 25 mg/ml, or about 20 mg/ml to about 23 mg/ml, or about 23 mg/ml to about 45 mg/ml, or about 23 mg/ml to about 40 mg/ml, or about 23 mg/ml to about 37 mg/ml, or about 23 mg/ml to about 35 mg/ml, or about 23 mg/ml to about 30 mg/ml, or about 23 mg/ml to about 25 mg/ml.

One of skill in the art will recognize that suitable total volume of the deterrent substance may be selected based on the size and shape of the medication 4 within the spaces 103. For example, the deterrent substance may be present in a volume of about 0.5 ml to about 40 ml; e.g., about 0.5 ml to about 35 ml, or about 0.5 ml to about 30 ml, or about 0.5 ml to about 25 ml or about 0.5 ml to about 30 ml, or about 0.5 ml to about 25 ml, or about 0.5 ml to about 20 ml, or about 0.5 ml to about 15 ml, or about 0.5 ml to about 10 ml, or about 0.5 ml to about 5 ml, or about 0.5 ml to about 2.5 ml, or about 2.5 ml to about 35 ml, or about 2.5 ml to about 30 ml, or about 2.5 ml to about 25 ml, or about 2.5 ml to about 20 ml, or about 2.5 ml to about 15 ml, or about 2.5 ml to about 10 ml, or about 2.5 ml to about 5 ml, or about 5 ml to about 35 ml, or about 5 ml to about 30 ml, or about 5 ml to about 25 ml, or about 5 ml to about 20 ml, or about 5 ml to about 15 ml, or about 5 ml to about 10 ml, or about 10 ml to about 35 ml, or about 10 ml to about 30 ml, or about 10 ml to about 25 ml, or about 10 ml to about 20 ml, or about 10 ml to about 15 ml, or about 15 ml to about 35 ml, or about 15 ml to about 30 ml, or about 15 ml to about 25 ml, or about 15 ml to about 20 ml.

In some embodiments, the deterrent substance includes a formulation that may be absorbed onto or into the medication 4 after a reasonable amount of time. In some embodiments, the deterrent substance may be absorbed onto or into the medication 4 after a range of about 2 minutes to about 24 hours; e.g., about 2 minutes to about 20 hours, or about 2 minutes to about 16 hours, or about 2 minutes to about 12 hours, or about 2 minutes to about 8 hours, or about 2 minutes to about 6 hours, or about 2 minutes to about 4 hours, or about 2 minutes to about 2 hours, or about 2 minutes to about 90 minutes, or about 2 minutes to about 60 minutes, or about 2 minutes to about 45 minutes, or about 2 minutes to about 30 minutes, or about 2 minutes to about 20 minutes, or about 2 minutes to about 15 minutes, or about 2 minutes to about 10 minutes, or about 2 minutes to about 5 minutes, or about 5 minutes to about 20 hours, or about 5 minutes to about 16 hours, or about 5 minutes to about 12 hours, or about 5 minutes to about 8 hours, or about 5 minutes to about 6 hours, or about 5 minutes to about 4 hours, or about 5 minutes to about 2 hours, or about 5 minutes to about 90 minutes, or about 5 minutes to about 60 minutes, or about 5 minutes to about 45 minutes, or about 5 minutes to about 30 minutes, or about 5 minutes to about 20 minutes, or about 5 minutes to about 15 minutes, or about 5 minutes to about 10 minutes, or about 10 minutes to about 20 hours, or about 10 minutes to about 16 hours, or about 10 minutes to about 12 hours, or about 10 minutes to about 8 hours, or about 10 minutes to about 6 hours, or about 10 minutes to about 4 hours, or about 10 minutes to about 2 hours, or about 10 minutes to about 90 minutes, or about 10 minutes to about 60 minutes, or about 10 minutes to about 45 minutes, or about 10 minutes to about 30 minutes, or about 10 minutes to about 20 minutes, or about 10 minutes to about 15 minutes, or about 15 minutes to about 20 hours, or about 15 minutes to about 16 hours, or about 15 minutes to about 12 hours, or about 15 minutes to about 8 hours, or about 15 minutes to about 6 hours, or about 15 minutes to about 4 hours, or about 15 minutes to about 2 hours, or about 15 minutes to about 90 minutes, or about 15 minutes to about 60 minutes, or about 15 minutes to about 45 minutes, or about 15 minutes to about 30 minutes, or about 15 minutes to about 20 minutes, or about 20 minutes to about 20 hours, or about 20 minutes to about 16 hours, or about 20 minutes to about 12 hours, or about 20 minutes to about 8 hours, or about 20 minutes to about 6 hours, or about 20 minutes to about 4 hours, or about 20 minutes to about 2 hours, or about 20 minutes to about 90 minutes, or about 20 minutes to about 60 minutes, or about 20 minutes to about 45 minutes, or about 20 minutes to about 30 minutes.

In some embodiments wherein the medication 4 is a liquid, a pharmaceutical film, an orally dissolving tablet, or the medication is tablet, capsule or caplet that is broken or crushed prior to or at the same time as the deterrent substance is dispensed, the deterrent substance may be absorbed or dispersed into the medication 4 from a range of about 0.1 seconds to about 30 seconds; e.g., about 0.1 seconds to about 25 seconds, or about 0.1 seconds to about 20 seconds, or about 0.1 seconds to about 15 seconds, or about 0.1 seconds to about 10 seconds, or about 0.1 seconds to about 5 seconds, or about 0.1 seconds to about 2.5 seconds, or about 0.1 seconds to about 1 second. In some embodiments, the deterrent substance is absorbed or dispersed into a liquid medication 4 instantaneously or immediately. In the case of liquid opioid agonist formulations, such as methadone liquid concentrate, the naltrexone formulation would become fully intermixed seconds after deployment. In the case of pharmaceutical film and orally dissolving opioid agonist formulations, such as buprenorphine film and buprenorphine orally dissolving tablets, the naltrexone formulation would become fully intermixed seconds after deployment. The present disclosure is especially effective with liquid, pharmaceutical film, and orally dissolving tablet formulations.

The deterrent substance is absorbed onto or into the medication 4 in an amount sufficient to diminish or eliminate the pleasure of abuse. In some embodiments, the amount of the deterrent substance absorbed onto or into the medication 4 in a range of about 0.4 mg to about 10 mg; e.g., about 0.4 mg to about 9.5 mg, or about 0.4 mg to about 9.0 mg, or about 0.4 mg to about 8.5 mg, or about 0.4 mg to about 8.0 mg, or about 0.4 mg to about 7.5 mg, or about 0.4 mg to about 7.0 mg, or about 0.4 mg to about 6.5 mg, or about 0.4 mg to about 6.0 mg, or about 0.4 mg to about 5.5 mg, or about 0.4 mg to about 5.0 mg, or about 0.4 mg to about 4.5 mg, or about 0.4 mg to about 4.0 mg, or about 0.4 mg, to about 3.5 mg, or about 0.4 mg to about 3.0 mg, or about 0.4 mg to about 2.5 mg, or about 0.4 mg to about 2.0 mg, or about 0.4 mg to about 1.5 mg, or about 0.4 mg to about 1.0 mg, or about 0.4 mg to about 1.0 mg, or about 0.4 mg to about 0.75 mg, or about 0.75 mg to about 9.5 mg, or about 0.75 mg to about 9.0 mg, or about 0.75 mg to about 8.5 mg, or about 0.75 mg to about 8.0 mg, or about 0.75 mg to about 7.5 mg, or about 0.75 mg to about 7.0 mg, or about 0.75 mg to about 6.5 mg, or about 0.75 mg to about 6.0 mg, or about 0.75 mg to about 5.5 mg, or about 0.75 mg to about 5.0 mg, or about 0.75 mg to about 4.5 mg, or about 0.75 mg to about 4.0 mg, or about 0.75 mg to about 3.5 mg, or about 0.75 mg to about 3.0 mg, or about 0.75 mg to about 2.5 mg, or about 0.75 mg to about 2.0 mg, or about 0.75 mg to about 1.5 mg, or about 0.75 g to about 1.0 mg, or about 1.0 mg to about 9.5 mg, or about 1.0 mg to about 9.0 mg, or about 1.0 mg to about 8.5 mg, or about 1.0 mg to about 8.0 mg, or about 1.0 mg to about 7.5 mg, or about 1.0 mg to about 7.0 mg, or about 1.0 mg to about 6.5 mg, or about 1.0 mg to about 6.0 mg, or about 1.0 mg to about 5.5 mg, or about 1.0 mg to about 5.0 mg, or about 1.0 mg to about 4.5 mg, or about 1.0 mg to about 4.0 mg, or about 1.0 mg to about 3.5 mg, or about 1.0 mg to about 3.0 mg, or about 1.0 mg to about 2.5 mg, or about 1.0 mg to about 2.0 mg, or about 1.0 mg to about 1.5 mg, or about 1.5 mg to about 9.5 mg, or about 1.5 mg to about 9.0 mg, or about 1.5 mg to about 8.5 mg, or about 1.5 mg to about 8.0 mg, or about 1.5 mg to about 7.5 mg, or about 1.5 mg to about 7.0 mg, or about 1.5 mg to about 6.5 mg, or about 1.5 mg to about 6.0 mg, or about 1.5 mg to about 5.5 mg, or about 1.5 mg to about 5.0 mg, or about 1.5 mg to about 4.5 mg, or about 1.5 mg to about 4.0 mg, or about 1.5 mg to about 3.5 mg, or about 1.5 mg to about 3.0 mg, or about 1.5 mg to about 2.5 mg, or about 1.5 mg to about 2.0 mg, or about 2.0 mg to about 9.5 mg, or about 2.0 mg to about 9.0 mg, or about 2.0 mg to about 8.5 mg, or about 2.0 mg to about 8.0 mg, or about 2.0 mg to about 7.5 mg, or about 2.0 mg to about 7.0 mg, or about 2.0 mg to about 6.5 mg, or about 2.0 mg to about 6.0 mg, or about 2.0 mg to about 5.5 mg, or about 2.0 mg to about 5.0 mg, or about 2.0 mg to about 4.5 mg, or about 4.0 mg, or about 2.0 mg to about 3.5 mg, or about 2.0 mg to about 3.0 mg, or about 2.0 mg to about 2.5 mg, or about 2.5 mg to about 9.5 mg, or about 2.5 mg to about 9.0 mg, or about 2.5 mg to about 8.5 mg, or about 2.5 mg to about 8.0 mg, or about 2.5 mg to about 7.5 mg, or about 2.5 mg to about 7.0 mg, or about 2.5 mg to about 6.5 mg, or about 2.5 mg to about 6.0 mg, or about 2.5 mg to about 5.5 mg, or about 2.5 mg to about 5.0 mg, or about 2.5 mg to about 4.5 mg, or about 2.5 mg to about 4.0 mg, or about 2.5 mg to about 3.5 mg, or about 2.5 mg to about 3.0 mg, or about 3.0 mg to about 9.5 mg, or about 3.0 mg to about 9.0 mg, or about 3.0 mg to about 8.5 mg, or about 3.0 mg to about 8.0 mg, or about 3.0 mg to about 7.5 mg, or about 3.0 mg to about 7.0 mg, or about 3.0 mg to about 6.5 mg, or about 3.0 mg to about 6.0 mg, or about 3.0 mg to about 5.5 mg, or about 3.0 mg to about 5.0 mg, or about 3.0 mg to about 4.5 mg, or about 3.0 mg to about 4.0 mg, or about 3.0 mg to about 3.5 mg, or about 3.5 mg to about 9.5 mg, or about 3.5 mg to about 9.0 mg, or about 3.5 mg or about 8.5 mg, or about 3.5 mg or about 8.0 mg, or about 3.5 mg or about 7.5 mg, or about 3.5 mg to about 7.0 mg, or about 3.5 mg to about 6.5 mg, or about 3.5 mg to about 6.0 mg, or about 3.5 mg to about 5.5 mg, or about 3.5 mg to about 5.0 mg, or about 3.5 mg to about 4.5 mg, or about 3.5 mg to about 4.0 mg, or about 4.0 mg to about 9.5 mg, or about 4.0 mg to about 9.0 mg, or about 4.0 mg or about 8.5 mg, or about 4.0 mg or about 8.0 mg, or about 4.0 mg or about 7.5 mg, or about 4.0 mg to about 7.0 mg, or about 4.0 mg to about 6.5 mg, or about 4.0 mg to about 6.0 mg, or about 4.0 mg to about 5.5 mg, or about 4.0 mg to about 5.0 mg, or about 4.0 mg to about 4.5 mg, or about 4.5 mg to about 9.5 mg, or about 4.5 mg to about 9.0 mg, or about 4.5 mg or about 8.5 mg, or about 4.5 mg or about 8.0 mg, or about 4.5 mg or about 7.5 mg, or about 4.5 mg to about 7.0 mg, or about 4.5 mg to about 6.5 mg, or about 4.5 mg to about 6.0 mg, or about 4.5 mg to about 5.5 mg, or about 4.5 mg to about 5.0 mg, or about 5.0 mg to about 9.5 mg, or about 5.0 mg to about 9.0 mg, or about 5.0 mg or about 8.5 mg, or about 5.0 mg or about 8.0 mg, or about 5.0 mg or about 7.5 mg, or about 5.0 mg to about 7.0 mg, or about 5.0 mg to about 6.5 mg, or about 5.0 mg to about 6.0 mg, or about 5.0 mg to about 5.5 mg.

In some embodiments, exposure to the deterrent substance may compromise the integrity of the medication 4. For example, the integrity of the medication may be compromised through disintegration of the medicine 4, or a viscoelastic, i.e., slimy appearance.

In some embodiments, the deterrent substance includes a thickening or gelling agent. In some embodiments, the thickening or gelling agent is Hydroxypropyl cellulose. In some embodiments, Hydroxypropyl cellulose may be present in the formulation at a concentration of about 0.2% to about 2.0%. For example, about 0.2% to about 1.8%, or about 0.2% to about 1.6%, or about 0.2% to about 1.4%, or about 0.2% to about 1.2%, or about 0.2% to about 1.0%, or about 0.2% to about 0.8%, or about 0.2% to about 0.6%, or about 0.2% to about 0.4%.

In some embodiments, the deterrent substance includes a colorant. The colorant may be soluble or formulated to suspend in solution. The colorant may be any suitable colorant. For example, the colorant may be methylene blue. In some embodiments, the colorant may be Opadry II. Opadry II may be present in a concentration of about 0.5% in the formulation. In some embodiments, the colorant may be D&C Red NO. 33. In some embodiments, the colorant may be FD&C Red NO. 40. In some embodiments, the colorant may be vitamin B12.

In some embodiments, the deterrent substance includes a component that emits a foul odor. In some embodiments, the component is butyric acid. Butyric acid may be present at any concentration suitable to emit a foul odor.

In some embodiments, the deterrent substance includes an acid in the formulation. In some embodiments, the acid is used as a pH adjuster. In some embodiments, the acid is citric acid.

In some embodiments, the deterrent substance includes a buffer and a preservative. In some embodiments, the deterrent substance includes propylene glycol. In some embodiments, the deterrent substance includes glycerin. In some embodiments, glycerin or propylene glycol is added to prevent freezing of the deterrent substance. Glycerin or propylene glycol may be present at any suitable concentration.

DESCRIPTION OF ILLUSTRATIVE EMBODIMENTS

In illustrative embodiments a device provides secure access to a drug and deters unauthorized access of the drug. The device includes a locking mechanism coupled to a physical barrier that prevents and/or mitigates access to the drug by unauthorized users, unauthorized dosages, and/or at unauthorized times. If the housing is improperly breached or accessed, a chemical deterrent is released. The chemical deterrent mixes with the drug, making the drug unsuitable for use.

FIG. 1 schematically shows another alternative embodiment of the abuse deterrent device 2 that is built-in to the housing 1 in accordance with illustrative embodiments of the invention. FIG. 1 schematically shows the physical deterrent 70 in the secured position. In this embodiment the abuse deterrent substance is pressurized by a spring 86. Alternatively, or additionally, the abuse deterrent container 34 may be pressurized by gas.

In some embodiments, the components of the device 2, including but not limited to the housing 1, the walls 5 of the housing 1, the physical deterrent 70 (e.g., lid) and the carousel 102 are formed from any pharmaceutically acceptable material, such as HDPE, polypropylene, polyethylene terephthalate, high density polyethylene, polyvinyl chloride, polystyrene, fluoropolymers, silicone, resins, polypropylene, polyethylene terephthalate and/or polylactide, which may be clear, tinted or opaque. The components of the device 2 are of a sufficient thickness and rigidity to prevent and/or significantly mitigate accessing the drug 4 by squeezing (e.g., as by a human grip trying to deform and/or open the housing 1, lid 70, or any part of the device 2). The housing 1 may be any container, e.g., a pharmaceutical bottle, and the housing 1 may hold the drug 4 therein. It should be understood that the housing 1 may come in a variety of sizes, e.g., as is typical with various pharmaceutical bottle sizes. In some embodiments, the walls 5 are integrally formed with the housing 1.

In some embodiments, the walls 5 of the housing 1 are hollow and filled with pressurized air. In alternative embodiments, the walls are filled with compressed nitrogen. Compressed nitrogen does not have water vapor in it and may keep the pressure within the walls 5 more steady than pressurized air. It should be understood that a variety of different compressed gases may be used, and that discussion of "air" is merely intended to facilitate discussion of illustrative embodiments, and not to limit them thereby.

The air pressure in the walls 5 pushes against a piston 109. At least a portion of the piston 109 is configured to move from the area of the pressurized bottle walls 5 (e.g., double layer walls) to the unpressurized environment inside the bottle (e.g., where the drugs 4 are). The piston 109 may be sealed with gaskets 112 to prevent pressure from escaping the bottle walls 5 while the piston 109 moves. In the embodiment shown, the tip 114 of the piston 109 presses into the abuse deterrent container 34 and seals it. When the tip 114 backs out of the abuse deterrent container 34, the pressure from the spring 86 pushes the plate 93 in the container 34, and causes the abuse deterrent substance, which is in the container 34, to spray out of the container 34 and down onto the medicine 4.

The tip 114 of the piston 109 may have a channel 95 through which deterrent substance may be dispensed. When the piston 109 partially backs out of the container 34, the channel 95 directs the abuse deterrent substance onto the drug 4. Thus, the channel 95 acts as a passageway that directs the deterrent substance towards the drug 4. In this manner, the pressure within the walls 5 keeps the abuse deterrent substance contained within the deterrent container 34.

The deterrent container 34 houses one or more deterrent substances such as, for example, a drug antagonist (e.g., naloxone, naltrexone, methylnaltrexone, and nalmefene), a bright colorant, D&C Red No. 33, FD&C Red No. 40, FD&C Green No. 3, D&C Violet No. 2, Vitamin B12, a black colorant (e.g., that makes the drug 4 less visually appealing as well as indicating that the antagonist has deployed), an emetic (e.g., ipecac syrup), a foul odor (e.g., pepsin and/or butanethiol), a gelling agent, an encapsulating agent (e.g., glue), a flushing agent (e.g., niacin), and/or an irritant (e.g., capsaicin). Other useful opioid receptor antagonists are known (see, e.g., Kreek et al., U.S. Pat. No. 4,987,136).

If the drug 4 is improperly accessed (e.g., by cutting through the walls 5), the pressure inside the wall 5 changes. The change in pressure activates the release of the deterrent substance. Like many containers that hold drugs 4, the housing 1 has a lid 70. The lid 70 is attached to the body of the housing 1 by a hinge 7. In some embodiments, the hollows walls 5 and the lid 70 are fluidly connected (e.g., by a tube 81) to form a connected uniform pressure. Thus, even if the user cuts through the lid 70, the pressure drop activates the release of the deterrent substance. Furthermore, in some embodiments there is a reservoir of compressed gas 100 inside the walls 5 to maintain a consistent pressure within the walls over time. In some embodiments, there is an adjustable pressure valve 90 that controls the pressure within the walls 5. To that end, a pharmacist who is giving out the medication may pressurize the container at the time of delivery to the patient and/or activate the deterrent system.

In some embodiments, the wall 5 and/or the lid 70 contain an electrically conductive matrix 80, such as a matrix of wires 80. If the wires 80 are broken and/or cut, this triggers a solenoid that pushes the tip 114 of the piston away from the container 34, and the deterrent substance is positioned (e.g., sprayed) onto the drug 4. Thus, illustrative embodiments release chemical deterrent when the user cuts and/or breaks through the housing 1 and/or the physical deterrent, including the lid 70.

Illustrative embodiments have a touchscreen 92 on the lid, through which the locking mechanism 32 may be accessed. In some embodiments the bottle is operated using simple buttons. The patient enters their code using the touchscreen 92 (for example, the code may be provided or set up by the medical practitioner). The touchscreen 92 thus may control a locking mechanism 32, act as a locking mechanism 32 by having a biometric scanner, it could have reminders and displays that notify the user (e.g., via sound or pop-up notifications), a calendar, and other normal functionalities associated with touch-screens (e.g., such as in a smartphone).

The signal from the touchscreen 92 may be sent through wires 94 to a motor 96 that is powered by a battery 98. The motor causes gears 88 to rotate, which in turn rotates a carousel 102. The carousel 102 has spaces 103 cut into it to accommodate a wide variety of medicine 4 shapes and sizes. In this embodiment the carousel has spaces 103 for 16 dosage units. However, the carousel may have more or less spaces 103. Not all the spaces 103 need to be filled by medicine 4. For example, one space 103 may be left empty so that there is not a drug 4 in the chute 107. Medicine 4 may be placed into the carousel 102 by a physician or pharmacist before the lid 70 is closed. In illustrative embodiments, once the lid 70 is closed, it cannot be opened without causing the abuse deterrent substance 34 to deploy, even if the passcode is correctly entered (e.g., because the passcode rotates the carousel 102—it does not open the lid 70). Furthermore, in some embodiments, there may be multiple tiers of the carousel 102 to facilitate holding more drugs. Illustrative embodiments of the carousel 102 may be porous so as not to prevent the deterrent substance from spraying through the tired carousel.

The lid 70 may be sealed closed by a clasp 104. The housing 1 may be sealed by a ring 106 that also holds the medicine 4 in place if the bottle is inverted. The ring 106 is porous, so as to not prevent the medicine 4 from being coated by the abuse deterrent substance 34. The carousel 102 may rotate and stop, positioning the medicine over the chute 107. The medicine then drops down the chute 107. The medicine may pass a counter 108. In this embodiment the counter 108 is a gate, however the counter may also be an optical counter. In some embodiments there is a gate and an optical counter that is located under the carousel 102. In some embodiments, the counter 108 only goes one-way, so as to prevent a user from trying to access the drug through the chute 107. In some embodiments, a sensor is connected to the chute 107 and to the valve 90, so that tampering with the chute 107 activates release of the deterrent substance (e.g., by opening the valve 90 and altering the pressure in the walls 5).

The bottle may be programmed by the physician or pharmacist to only dispense medication 4 at certain intervals. The bottle may also be programmed to provide reminders to take medication 4. The bottle may also be programmed to deploy the abuse deterrent substance after a certain interval, for example after a week, or after a month, of after six months. The timed deployment of the abuse deterrent substance removes the useful opioid from circulation, and thereby prevents an excess of unused opioid that could lead to misuse or abuse.

The device 2 may have a processor (not shown) that controls the valve 90. For example, the processor may be a part of the touchscreen 92. When the valve 90 is opened, the bottle walls 5 lose pressure, the abuse deterrent substance 34 is sprayed onto the drug 4. In some embodiments, the valve may open automatically at a week, month, three-months, six-months, and/or at the expiration of the medicine 4. Manipulation of the chute 107, the counter 108, and/or the carousel 102, may cause the valve 90 to open.

In alternative embodiments, the walls 5 may contain a conductive wire matrix (in addition to, or instead of, pressurized air), a solenoid may cause the abuse deterrent substance to deploy if a wire 80 is cut. In some embodiments, the walls may be pressurized and include an electrical matrix, thus, the bottle may have a pressure sensor 110 to monitor the pressure within the walls. The bottle walls 5 may be formed in part or in whole from a material that is porous, to allow a precisely controlled release of pressure. This precise release of pressure may cause the abuse deterrent substance to deploy after a predetermined period of time even if the electronics fail (e.g., after 1 month, or six months).

In some embodiments, the lock 32 is a biometric scanner such as a fingerprint scanner. Accordingly, the lock 32 does not open unless the fingerprint which has been programmed is pressed against the lock. The lock 32 may also incorporate a timer that is set to the expiration date of the contained medicine, or to a set interval of a treatment period assigned by a health care worker. As an illustrative example the timer could be set to lock the bottle after a 7 day course of pain medicine is complete.

In some embodiments, the device 2 may be coupled to a dosage counter. Depending on the type of drug 4, the dosage counter may be configured to count the dosage in number of pills, milliliters of fluid, and/or milligrams of drug that is released from the housing 1. After a threshold of dosage has been reached, the dosage counter may be configured to activate the locking mechanism. Furthermore, in some embodiments, an actuator may be coupled to the dosage counter and may cause the physical deterrent to move to the secured position.

Additionally, or alternatively, a dosing scheduler may be coupled to the locking mechanism and/or physical deterrent. The dosing scheduler may control the locking mechanism to unlock only during certain times of the day (e.g., for 30 minutes, between 9 AM and 10 AM, once every other day, etc.).

The device 2 may be network enabled (e.g., Wi-Fi), to receive updates from medical staff (e.g., prescribing doctor) regarding the amount and timing of drug to be released. Additionally, the device may forward data to the doctor regarding the timing and dosage of drug accessed. In some embodiments, the device 2 has network connectivity capabilities and may communicate with an external site and provide information or receive information. In some other embodiments, the device 2 may have an electronic display which may be a touchscreen. The device 2 may also incorporate audible, visual, vibratory or other types of alerts and reminders for the patient 8.

FIGS. 2-7 schematically show another alternative embodiment of the abuse deterrent device 2 that is built-in to the housing 1 in accordance with illustrative embodiments of the invention. FIGS. 2-7 schematically show different views of this embodiment with the physical deterrent 70 in the secured position. In this embodiment the abuse deterrent substance is pressurized by a spring 86. Alternatively, or additionally, the abuse deterrent container 34 may be pressurized by gas.

The housing 1 may be any container, e.g., a pharmaceutical bottle formed from pharmaceutically acceptable material, as described previously herein. As described previously, the bottle may hold the drug 4 therein.

In some embodiments, the walls 5 of the housing 1 may be hollow and filled with pressurized air. In alternative embodiments, the walls may be filled with compressed nitrogen. Compressed nitrogen does not have water vapor in it and may keep the pressure within the walls 5 more steady than pressurized air. It should be understood that a variety of different compressed gases may be used, and that discussion of "air" is merely intended to facilitate discussion of illustrative embodiments, and not to limit them thereby.

Figure 6:
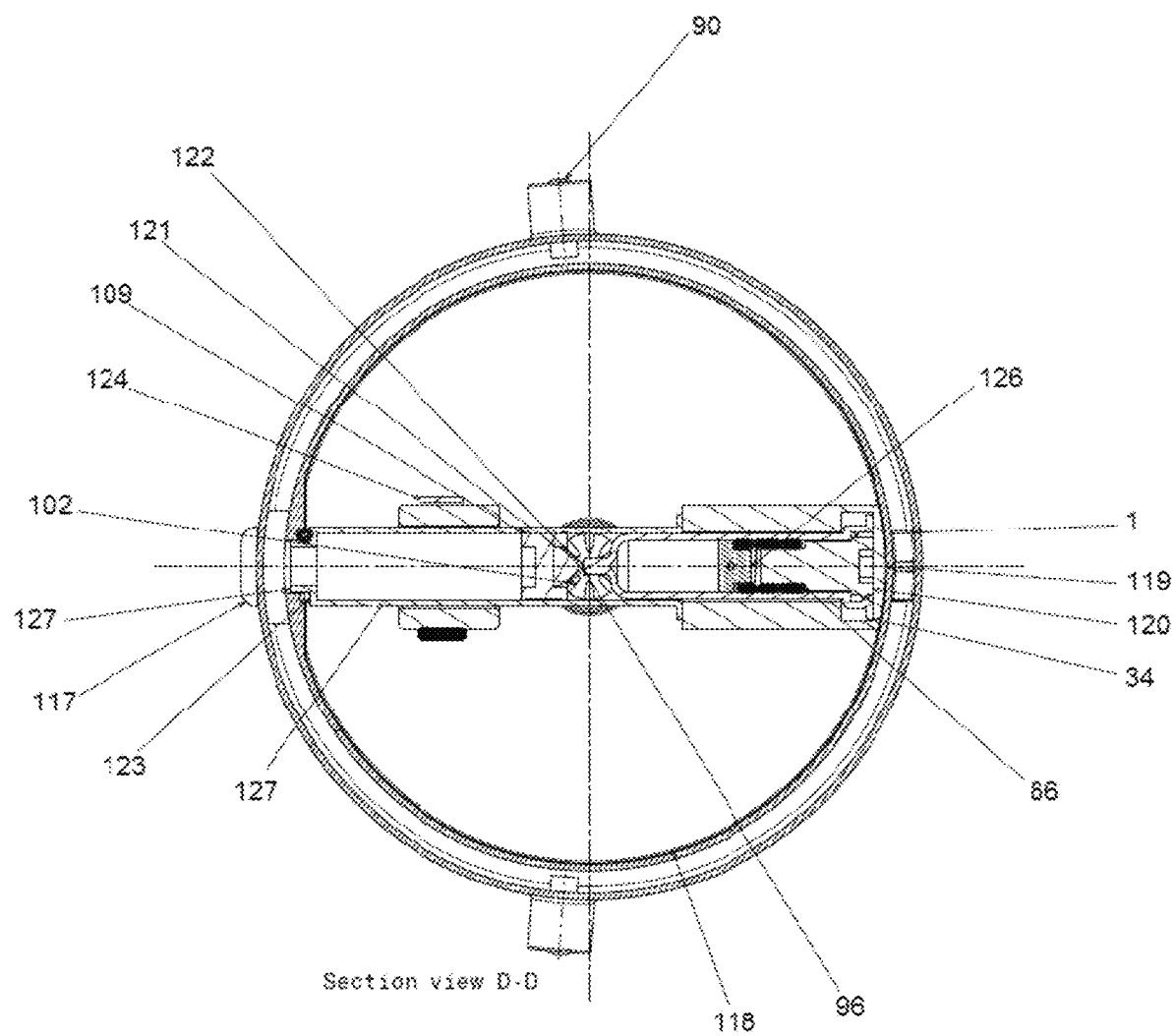
FIG. 6 schematically shows an alternative view of the abuse deterrent device that is built-in to the drug housing in accordance with illustrative embodiments of the invention, as shown in FIGS. 2-5.
Figure 7:
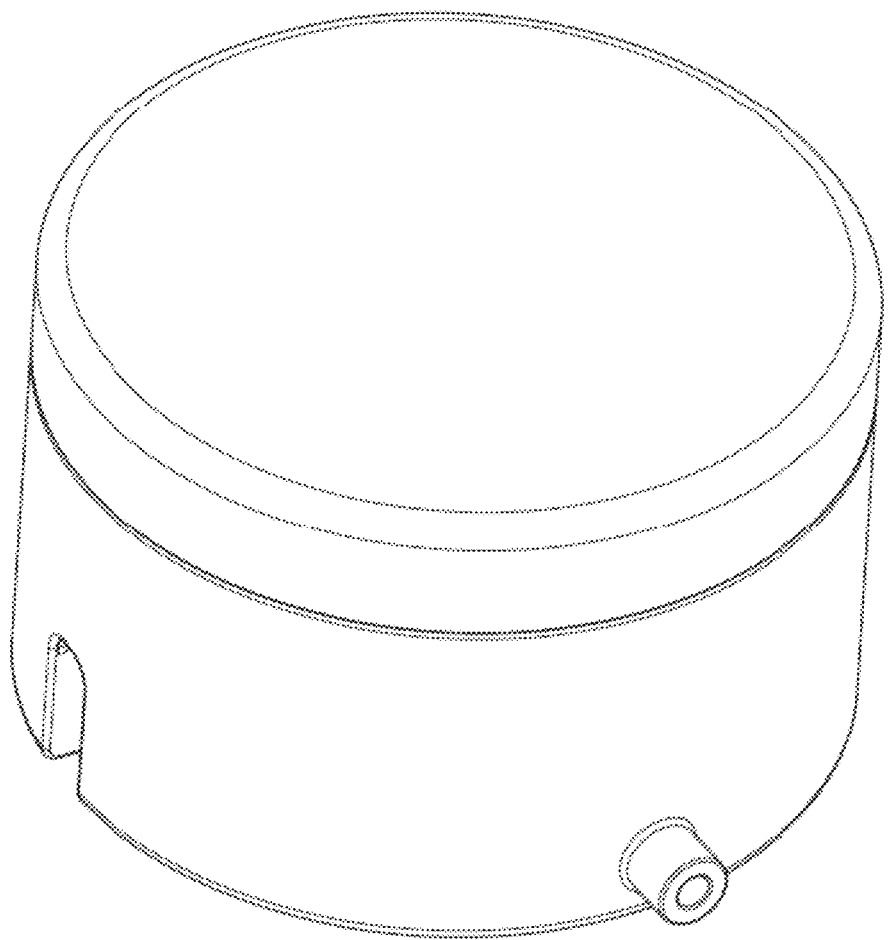
FIG. 7 schematically shows an isometric view of the abuse deterrent device that is built-in to the drug housing in accordance with illustrative embodiments of the invention, as shown in FIGS. 2-6.

In some embodiments, a pressure cylinder 127 is attached to a piston 109. In the embodiment shown, the piston 109 is a pressure piston 109 which is attached to a sealing needle 121 and sealing needle cover 122. The sealing needle 121 presses through the sealing needle cover 122, into the abuse deterrent container 34 and seals it. A locking piece 124 and an o-ring 123 are attached to the pressure cylinder 127. As shown in FIG. 6, when the pressure container 127, pressure piston 109, sealing needle 121 and sealing needle cover 122 back out of the abuse deterrent container 34, the pressure from the compression spring 86, which may include a spring support 120, pushes a piston 126 located in the abuse deterrent container 34, and causes the abuse deterrent substance, which is in the container 34, to spray out of the container 34 and down onto a carousel 102 and the medicine 4.

If the drug 4 is improperly accessed (e.g., by cutting through the walls 5), the pressure inside the wall 5 changes. The change in pressure activates the release of the deterrent substance. Like many containers that hold drugs 4, the housing 1 has a lid 70 and a sealing cup 125. In some embodiments, the hollows walls 5 and the lid 70 are fluidly connected (e.g., by a tube 81, as shown in FIG. 1) to form a connected uniform pressure. Thus, even if the user cuts through the lid 70, the pressure drop activates the release of the deterrent substance. Furthermore, in some embodiments there is at least one adjustable pressure valve 90 that controls the pressure within the walls 5. In some embodiments, there are two or more adjustable pressure valves. To that end, a pharmacist who is giving out the medication may pressurize the container at the time of delivery to the patient and/or activate the deterrent system.

Illustrative embodiments have a button 116 covered by a button cover 117 near the base of the housing 1. In other embodiments the button 116 may be many buttons, a touch screen, a biomentric sensor, or a wireless receiver. The term button is simply an illustrative term and not intended to limit the ways a user may attempt to unlock or access the medication 4.

In some embodiments, a motor 96 is attached to a battery 98. The motor 96, which may be a stepper DC motor, causes gears to rotate, which in turn rotates the carousel 102. The carousel 102 is supported by a carousel support 118 underneath and a carousel support on top 119. In some embodiments the carousel has spaces 103 for multiple dosage units (as shown in FIG. 1). However, the carousel may have more or less spaces 103. Not all the spaces 103 need to be filled by medicine 4. For example, one space may be left empty so that there is not a drug in the chute 107. Medicine 4 may be placed into the carousel 102 by a physician or pharmacist before the lid 70 is closed. In illustrative embodiments, once the lid 70 is closed, it cannot be opened without causing the abuse deterrent substance 34 to deploy, even if the button 116 is depressed or the passcode is correctly entered (e.g., because the button and/or the passcode rotate the carousel 102—they do not open the lid 70). Furthermore, in some embodiments, there may be multiple tiers of the carousel 102 to facilitate holding more drugs. Illustrative embodiments of the carousel 102 may be porous so as not to prevent the deterrent substance from spraying through the tired carousel.

In some embodiments there is no motor 96 (not shown). In these embodiments pressing the button 116 may allow for the manual rotation of the carousel within the bottle. In some embodiments, pressing the button 116 unlocks the carousel 102 for about one second, or about five seconds, or about ten seconds, or about twenty seconds, or about thirty seconds, or about forty-five seconds, or about one minute, or about two minutes, or about three minutes, or about four minutes, or about five minutes, or for an unlimited period of time. In some embodiments the bottle may rotate in half, or it may have a gear that is exposed and may be manually rotated. In some embodiments pressing the button does not automatically rotate the carousel, but rather unlocks the carousel to allow for manual rotation.

FIGS. 8-12 schematically show another alternative embodiment of the abuse deterrent device 2 that is built-in to the housing 1 in accordance with illustrative embodiments of the invention. FIGS. 8, 9, 11 and 12 schematically show different views of this embodiment with the physical deterrent 70 in the secured position.

The housing 1 may be any container, e.g., a pharmaceutical bottle formed from pharmaceutically acceptable material, as described previously herein. As described previously, the bottle may hold the drug 4 therein.

Figure 8:
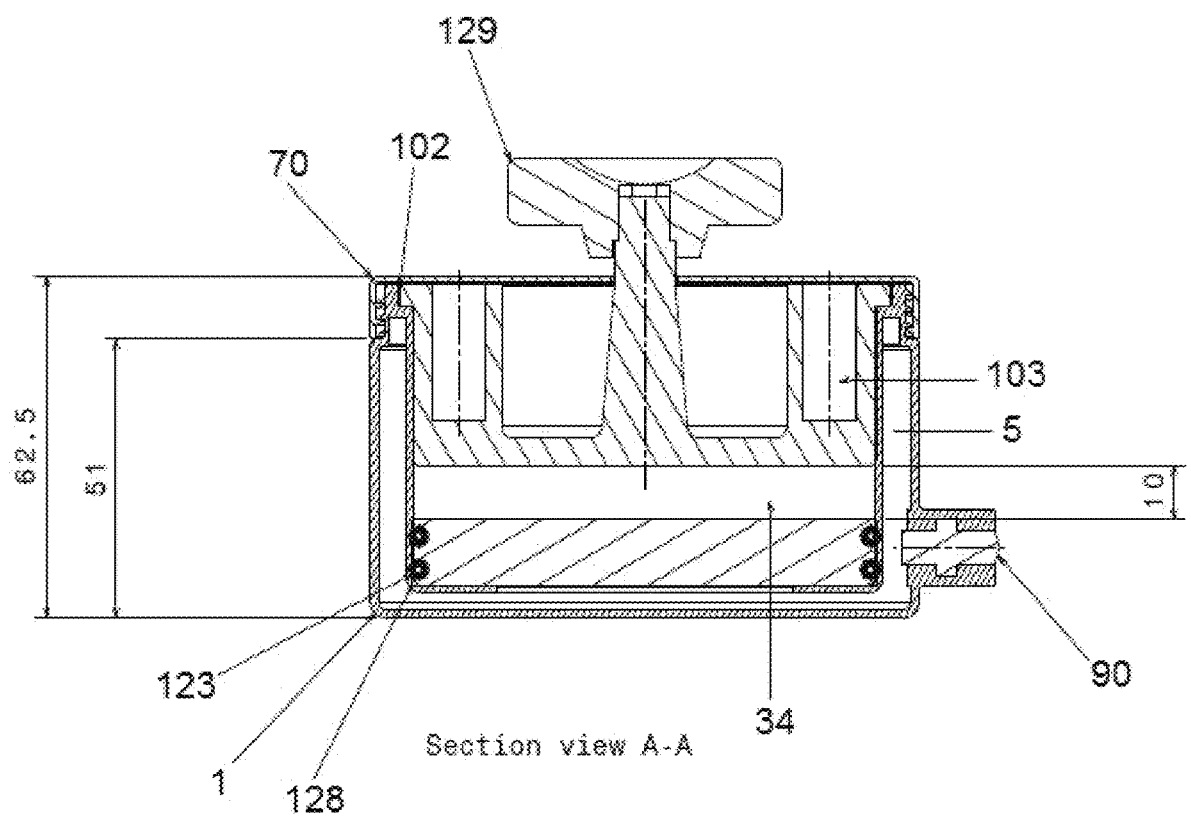
FIG. 8 schematically shows another alternative embodiment of the abuse deterrent device that is built-in to the drug housing in accordance with illustrative embodiments of the invention.
Figure 9:
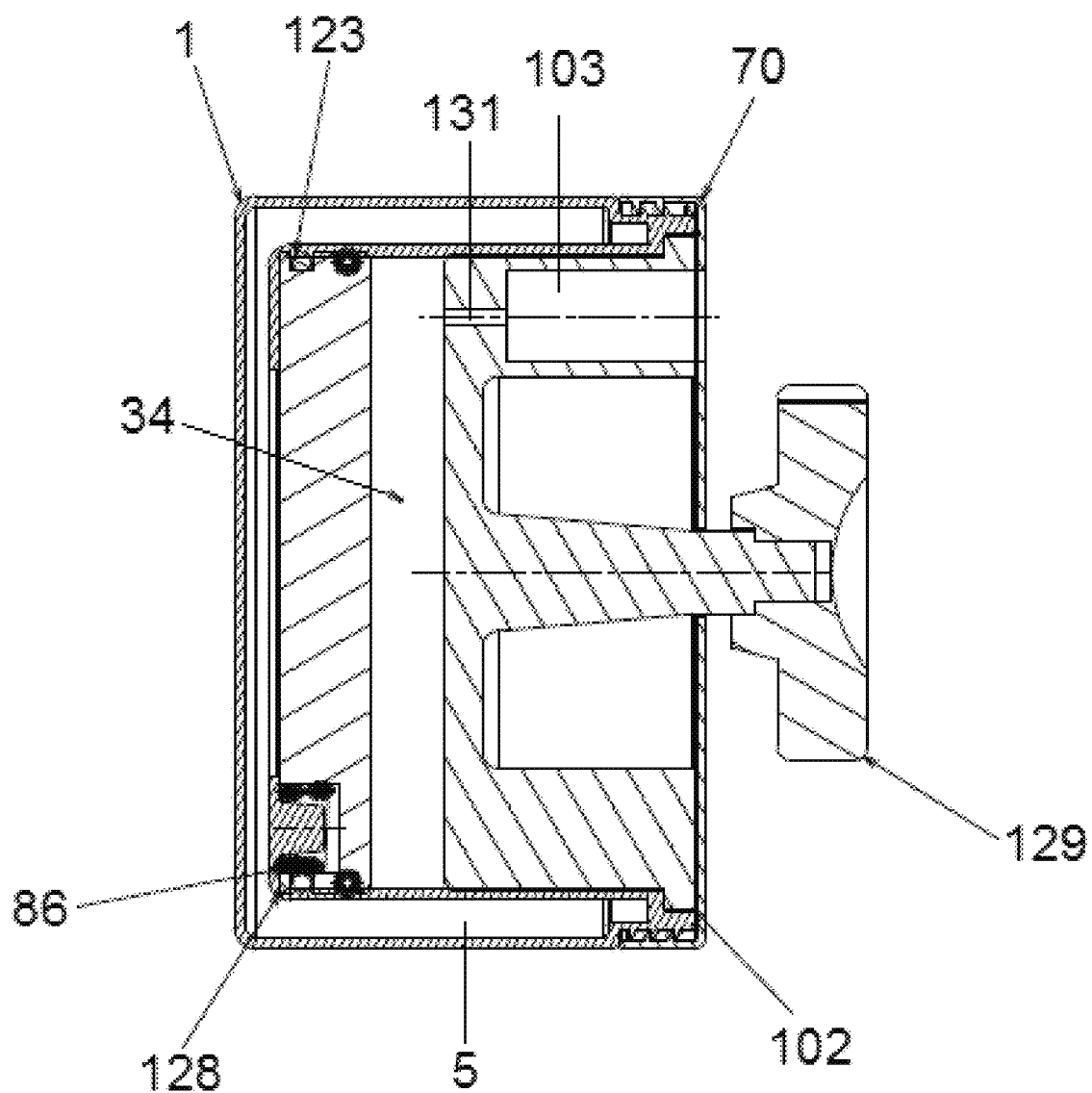
FIG. 9 schematically shows an alternative view of the abuse deterrent device that is built-in to the drug housing in accordance with illustrative embodiments of the invention, as shown in FIG. 8.
Figure 10:
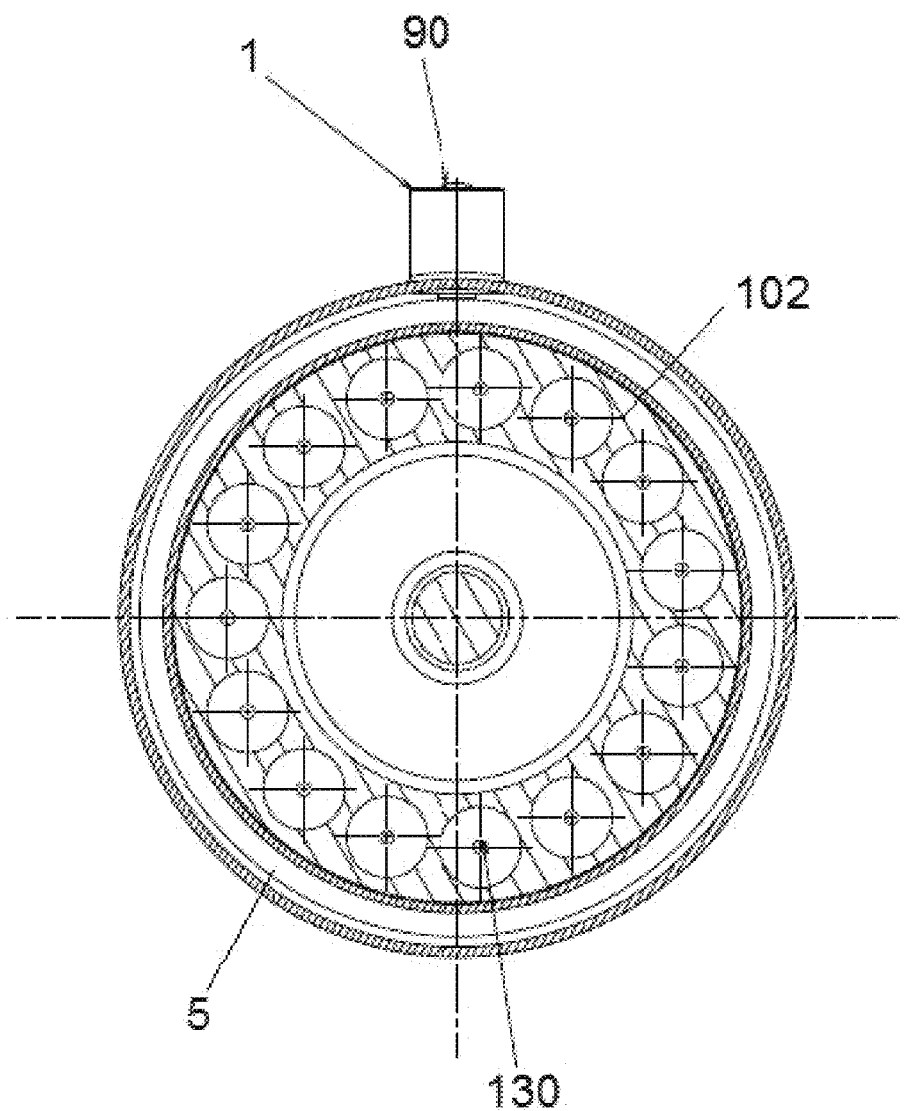
FIG. 10 schematically shows an alternative view of the abuse deterrent device that is built-in to the drug housing in accordance with illustrative embodiments of the invention, as shown in FIGS. 8 and 9.

In some embodiments, the walls 5 of the housing 1 may be hollow and under negative pressure, such as by vacuum. In some embodiments, a locking piece (not shown) and an o-ring 123 are attached to the housing 1. As shown in FIG. 8, when there is a pressure change in the walls 5 of the housing 1, a piston 128 raises, deploying the abuse deterrent substance 34 into the spaces 103 which hold the medicine 4. In such embodiments, the abuse deterrent substance 34 is contained in an area of the housing 1 on top of the piston 128. In some embodiments, the abuse deterrent substance 34 is contained in a 10 mm high area on top of the piston 128. In some embodiments, the abuse deterrent substance 34 is contained in a multitude of independent compartments on top of the piston 128. In some embodiments, the abuse deterrent substance 34 is contained in 15 independent compartments. In some embodiments, the abuse deterrent substance 34 is contained in an independent compartment for each medicine 4 dosage. The spaces 103 may hold the medicine 4 vertically or horizontally. In some embodiments, the carousel 102 includes a flap or cover attached to each of the spaces 103. In some embodiments, each flap or cover is maintained in the open position when the housing is under negative pressure or vacuum, and when the vacuum is released, each flap or cover moves to the closed position, covering each space 103. In some embodiments, the spaces 103 which hold the medicine 4 are porous or include a perforation, such as but not limited to a hole or a slit. As shown in FIG. 10, the spaces 103 are porous or perforated 130 at the bottom. In some embodiments and as shown in FIG. 9, a hollow tube 131 is located at the bottom of the spaces 103.

If the drug 4 is improperly accessed (e.g., by cutting through the walls 5 or breaking or cutting into the lid 70), the negative pressure inside the wall 5 changes. In illustrative embodiments, cutting through the walls 5 causes the pressure inside the walls 5 to equalize with pressure outside the walls 5. The release of vacuum removes the restraining force on the piston 128 which allows compressed springs 86 under the piston to activate the raising of the piston 128 and release of the deterrent substance. The housing 1 includes a device which prevents the deterrent substance from being released without a change in pressure. Said device may be, for example, a seal, cover, barrier shield, flap, or insert. Said device may also be a container that holds the deterrent substance that is pierced by a needle or a blade during a pressure change. Said device may be one or many containers. The activating piston may burst the container without a needle or a blade. The housing 1 may also have no device that would prevent the release of the deterrent to the medicine if the housing is inverted or shaken, in order to prevent common modes of tampering. The device may be formed from a pharmaceutically acceptable material. The device may be formed from one or more of fluoropolymers, silicone, resins, polypropylene, or polyethylene terephthalate. In some embodiments, said device is a movable seal, cover, barrier or shield which prevents the deterrent substance 34 from entering the spaces 103 containing the medication 4 through the perforation 130 or hollow tube 131. When the deterrent system is active, the device is located such that it covers the perforations 103 or hollow tubes 131 in the spaces 103 which store the medication 4. When the drug is improperly accessed, the device is moved or repositioned to uncover the perforations 130 or hollow tubes 131 in the spaces 103 containing the medication 4, allowing the deterrent substance to enter the spaces 103, and cover the medication 4. In some embodiments, the device moves or is repositioned by rotating or sliding. In embodiments where the deterrent substance is in a sealed container, a needle or blade may pierce the sealed container and allow the deterrent substance to enter the spaces 103. In some embodiments, the deterrent substance is in individual sealed containers, such as balloons, which are attached to each space 103 and inflated when under vacuum. In such embodiments, when the vacuum is released, the balloon deflates, releasing the deterrent substance into each space 103. In some embodiments it may be beneficial to allow the deterrent to enter the spaces 103 if the device is shaken or inverted and so there is no device to prevent this.

Figure 11:
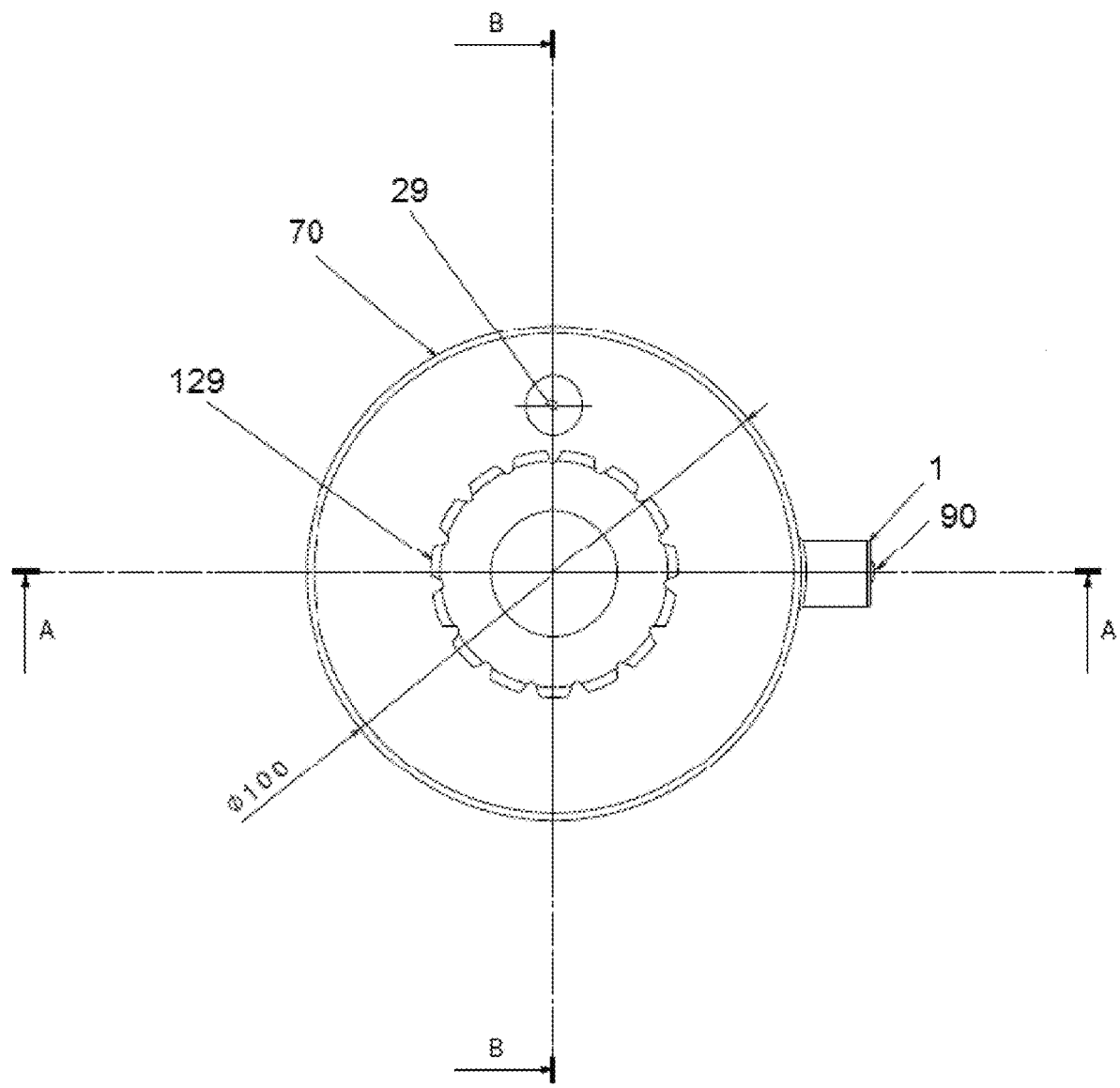
FIG. 11 schematically shows an alternative view of the abuse deterrent device that is built-in to the drug housing in accordance with illustrative embodiments of the invention, as shown in FIGS. 8-10.
Figure 12:
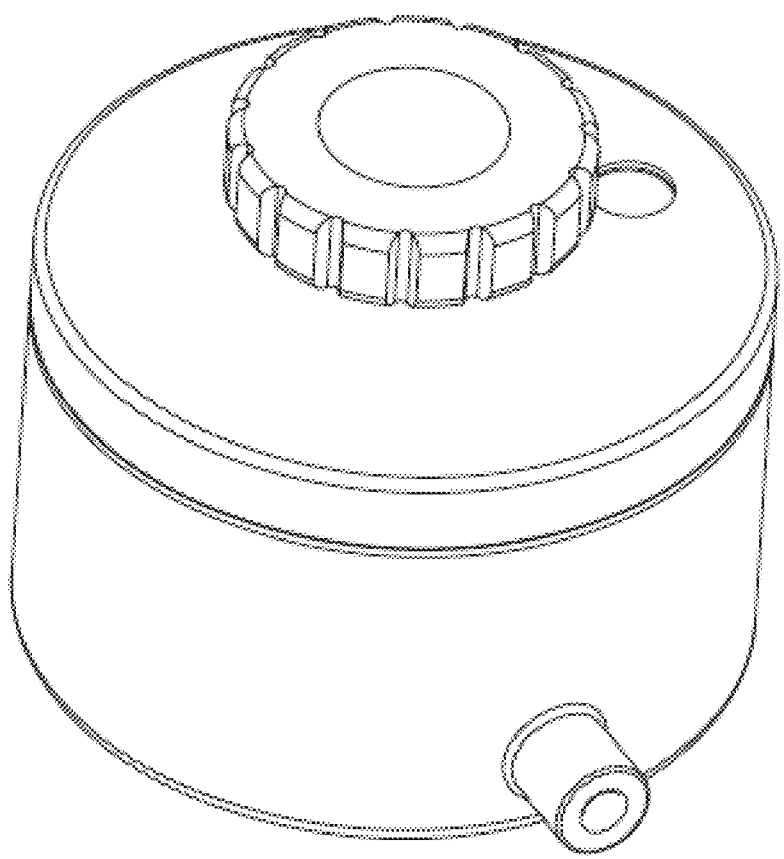
FIG. 12 schematically shows an isometric view of the abuse deterrent device that is built-in to the drug housing in accordance with illustrative embodiments of the invention, as shown in FIGS. 8-11.

Like many containers that hold medication 4, the housing 1 has a lid 70. In some embodiments, the lid 70 is clear, which provides a benefit of easy visibility to load the medication 4 and determine quantity of medication remaining in the container. In some embodiments, the lid 70 includes an access port 29, through which the medication 4 may be loaded and/or dispensed. (FIG. 11). In some embodiments, the hollows walls 5 and the lid 70 are fluidly connected (e.g., by a tube 81, as shown in FIG. 1) to form a connected uniform pressure. Thus, even if the user cuts through the lid 70, the reduction in negative pressure activates the release of the deterrent substance. Furthermore, in some embodiments the container includes at least one adjustable pressure valve 90 that controls the pressure within the walls 5. In some embodiments, there are two or more adjustable pressure valves. In some embodiments, the manufacturer may place the walls 5 of the container under negative pressure, e.g, by vacuum, and/or activate the deterrent system. In some embodiments, a pharmacist may place the walls 5 of the container under negative pressure, such as, by non-limiting example, by vacuum, and/or activate the deterrent system prior to or at the time of delivery to the patient.

Some embodiments may include a button which must be depressed to access the medication 4. In some embodiments, the button is located on the housing 1. In some embodiments, the button is located on the lid 70. In some embodiments, the button is located on a rotatable portion of the housing or the lid 129. In other embodiments the button may be many buttons, a touch screen, a biomentric sensor, or a wireless receiver. The term button is simply an illustrative term and not intended to limit the ways a user may attempt unlock or access the drug.

The rotatable portion of the housing or the lid 129 may be turned which causes rotation of the carousel 102. In some embodiments the carousel has spaces 103 for multiple dosage units (as shown in FIGS. 8, 9 and 10). However, the carousel may have more or less spaces 103. Not all the spaces 103 need to be filled by medicine 4. Medicine 4 may be placed into the carousel 102 by a physician or pharmacist before the lid 70 is closed. In illustrative embodiments, once the lid 70 is closed, it cannot be opened without causing the abuse deterrent substance to deploy, even if the button 116 is depressed or the passcode is correctly entered (e.g., because the button and/or the passcode rotate the carousel 102—they do not open the lid 70). Furthermore, in some embodiments, there may be multiple tiers of the carousel 102 to facilitate holding more drugs. Illustrative embodiments of the carousel 102 may be porous so as not to prevent the deterrent substance from spraying through the tiered carousel.

In some embodiments there is no motor 96. In these embodiments pressing the button 116 may allow for the manual rotation of the carousel within the housing 1. In some embodiments, pressing the button 116 unlocks the carousel 102 for about one second, or about five seconds, or about ten seconds, or about twenty seconds, or about thirty seconds, or about forty-five seconds, or about one minute, or about two minutes, or about three minutes, or about four minutes, or about five minutes, or for an unlimited period of time. In some embodiments pressing the button does not automatically rotate the carousel 102, but rather unlocks the carousel 102 to allow for manual rotation.

In some embodiments the device has sensors that will activate the release of the deterrent substance if tampering is detected. Illustrative sensors may detect immersion in water, inversion, shaking, freezing, heating, and or forcing the access port. In some embodiments the access port 29 is elongated and/or angled to prevent improper access of the drug 4. In some embodiments the port 29 is made of a material that will easily break or tear if manipulation of the port 29 is attempted. Example materials include foil or glass.

Figure 13:
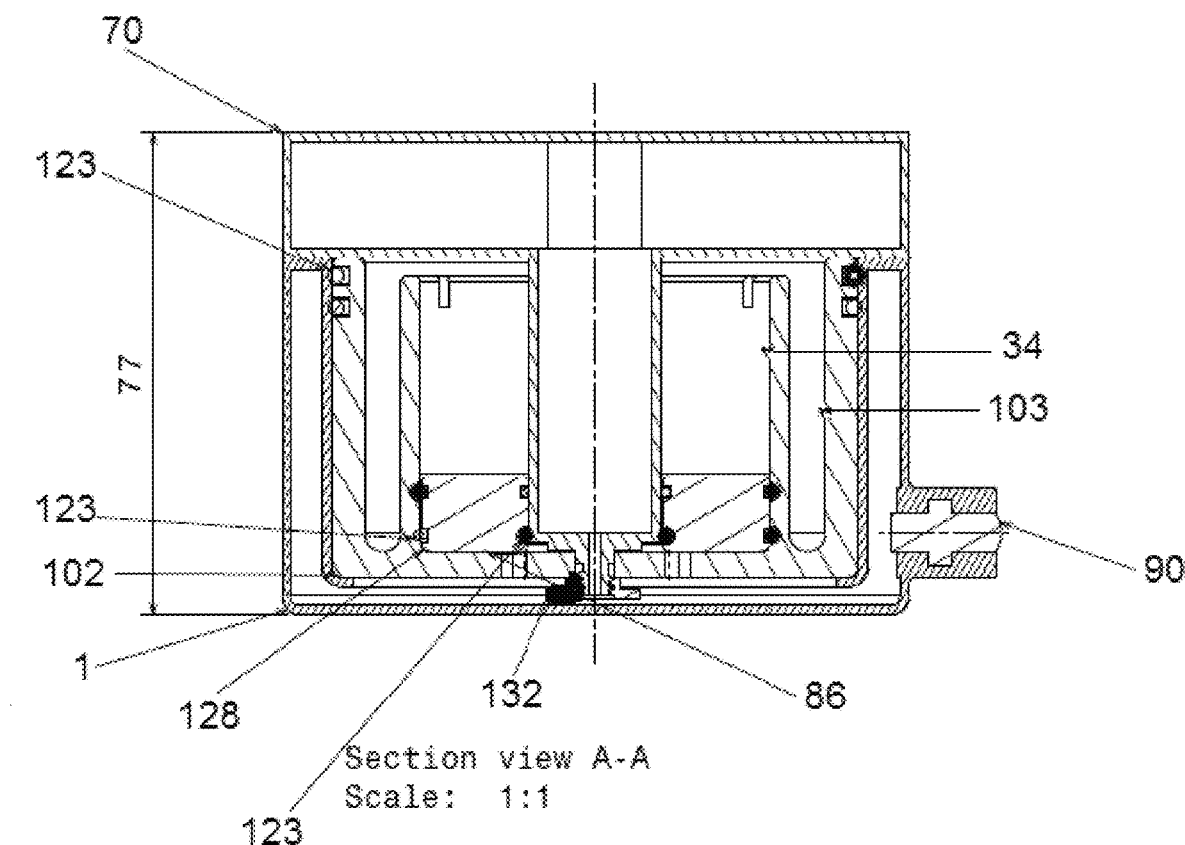
FIG. 13 schematically shows another alternative embodiment of the abuse deterrent device that is built-in to the drug housing in accordance with illustrative embodiments of the invention.
Figure 14:
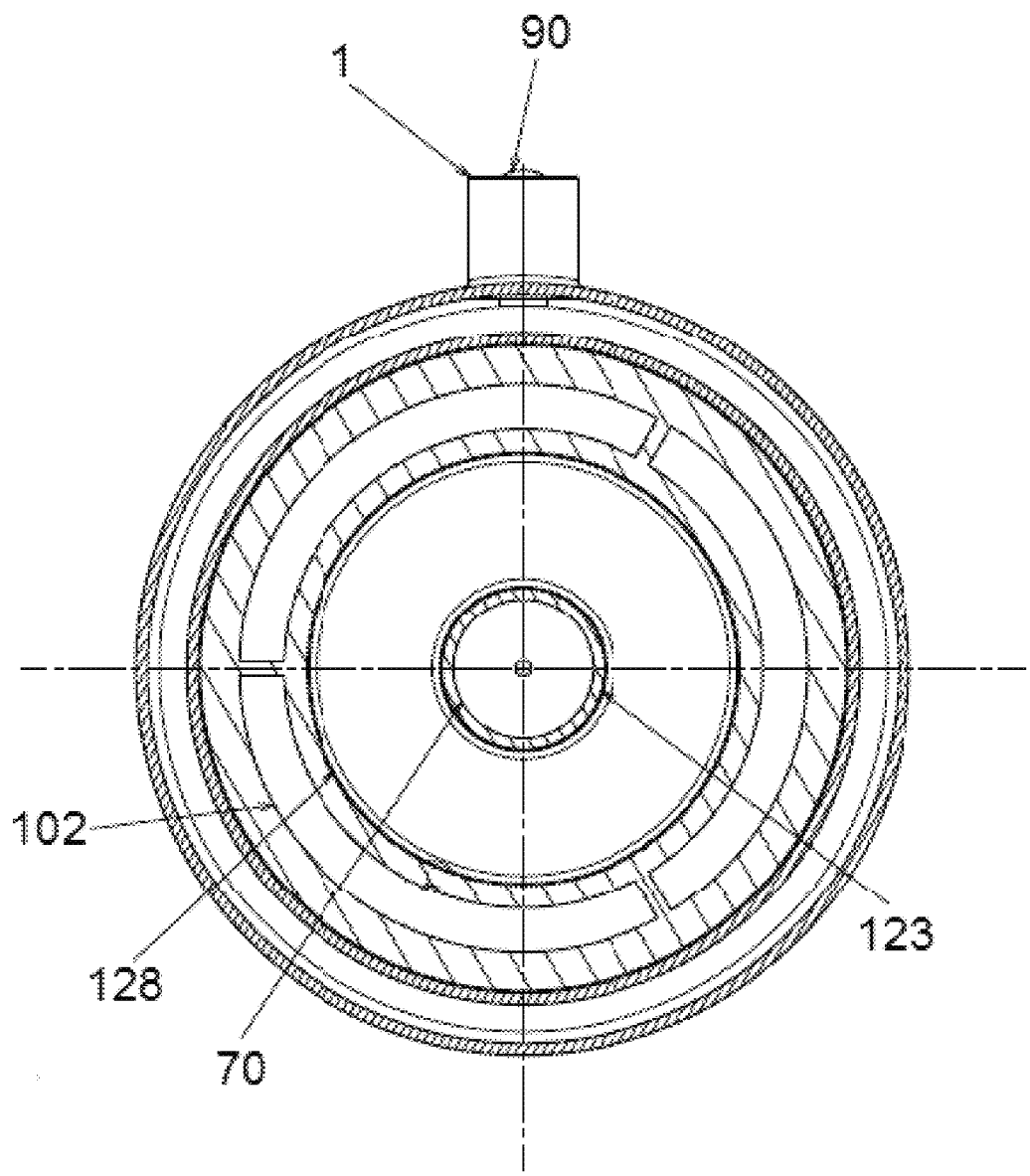
FIG. 14 schematically shows an alternative view of the abuse deterrent device that is built-in to the drug housing in accordance with illustrative embodiments of the invention, as shown in FIG. 13.

In some further embodiments of FIGS. 8-12, the spaces 103 are designed as cups to hold liquid formulation for oral consumption. Such embodiments are exemplified in FIGS. 13-15. In some embodiments, the carousel includes between 1 and 10 spaces. In some embodiments, for example, the carousel includes 1 space, or 2 spaces, or 3 spaces, or 4 spaces, or 5 spaces, or 6 spaces, or 7 spaces, or 8 spaces, or 9 spaces, or 10 spaces. The spaces 103 may hold between about 5 mL and 25 mL of liquid formulation for oral consumption. For example, the spaces 103 may hold between about 5 mL and about 20 mL, or about 5 mL and about 15 mL, or about 5 mL and about 10 mL, or about 10 mL and about 20 mL, or about 10 mL to about 15 mL of liquid formulation for oral consumption.

Figure 15:
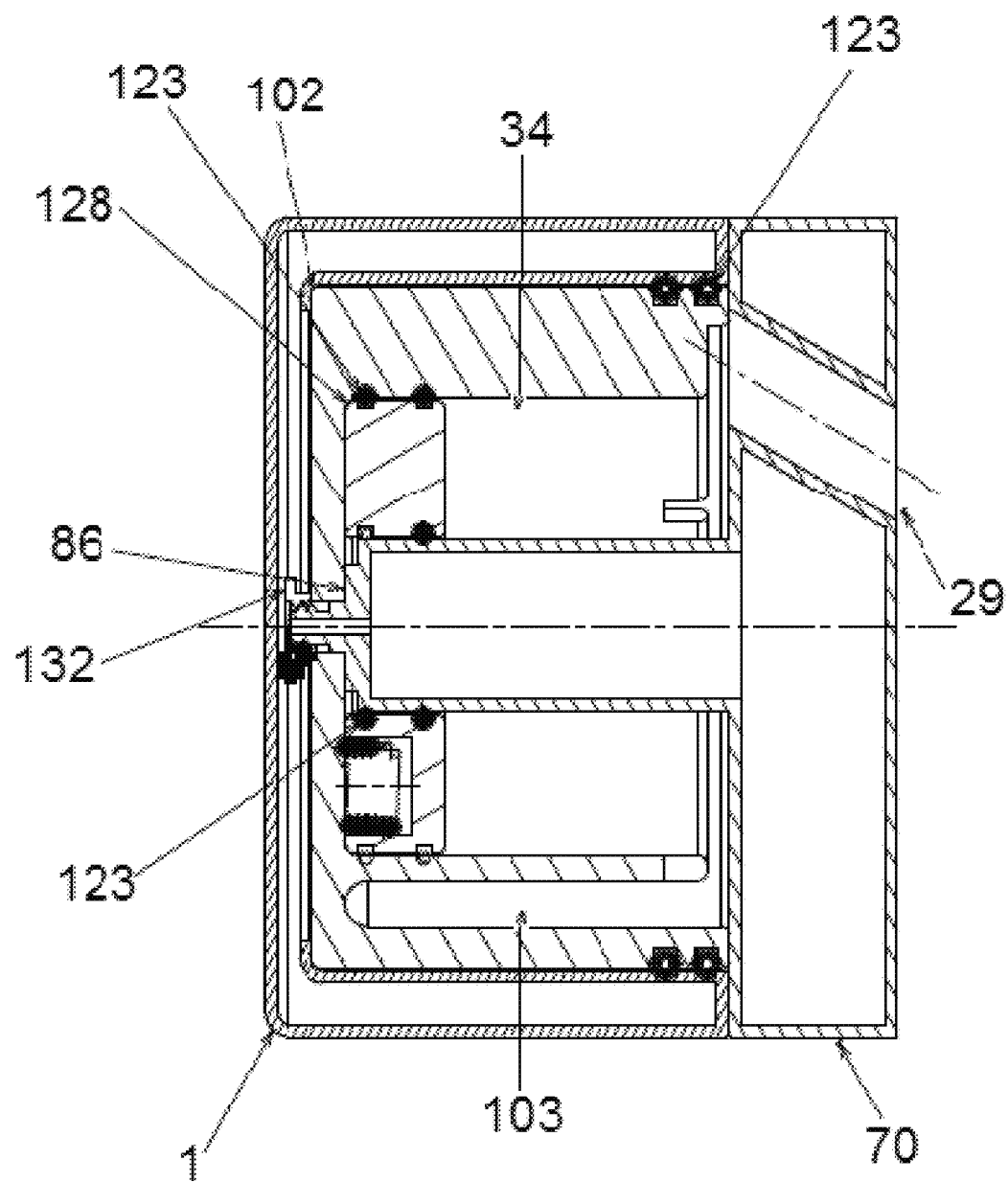
FIG. 15 schematically shows an alternative view of the abuse deterrent device that is built-in to the drug housing in accordance with illustrative embodiments of the invention, as shown in FIGS. 13 and 14.

In some embodiments, the lid 70 includes a rotatable portion 129 which may rotate the carousel 102 under appropriate circumstances. In some embodiments, the lid 70 includes a double wall that is continuous with the double wall of the housing 1. In some embodiments, the continuous double wall layer is under negative pressure. In some embodiments, the access port 29 within the lid 70 is elongated and/or angled to prevent improper access of the drug. (FIG. 15).

In some embodiments, the housing 1 includes a piece 132 which prevents the lid 70 from being detached from the housing 1. In some embodiments, the piece 132 is a nut. In some embodiments, the housing 1 includes a piston 128 located in the middle of the carousel 102.

In illustrative embodiments, if the housing 1 is improperly breached (e.g., cut open) then the pressure inside the walls 5 changes, resulting in insufficient counter pressure to block release of the contents within the deterrent compartment 34. Thus, the contents within the deterrent compartment 34 are released onto the drug 4. Additionally, or alternatively, in some embodiments a spring 86, the tip 114 of a piston 109, a piston itself (e.g., 128 or 132), or a plate 93, provides the counter pressure to prevent release of the contents of the deterrent compartment 34. The above described illustrative embodiments are merely exemplary, and are not intended to limit various embodiments of the invention. A person of skill in the art would understand numerous other ways through which the release of the deterrent substance within the deterrent container 34 can be activated (e.g., electronically opening/closing nozzle).

A person of skill in the art will be able to modify the device, shape and or material of the deterrent container 34, the spring 86 (e.g., stiffness), the piston etc. to prevent the accidental release of the deterrent substance in the compartment 34 during the normal use of the device 2. Thus, various embodiments may be configured to account for different circumstances that may be encountered normally in use (e.g., if a part of the device 2 is accidentally crushed—some embodiments may account for this change in pressure and are configured not to release the deterrent 34 absent a certain threshold change in pressure of the walls 5).

FIGS. 16-28 schematically show another alternative embodiment of an abuse deterrent device 2 that is a separate piece which may connect to or be inserted into a housing 1 in accordance with illustrative embodiments of the invention.

The housing 1 may be any container, e.g., a pharmaceutical bottle formed from pharmaceutically acceptable material, as described previously herein. The abuse deterrent device 2 may be any container which connects to or may be inserted into the housing 1, or may be part of any such container. In some embodiments, the abuse deterrent device is part of a carousel 102, as previously described herein, and the carousel 102 may hold the drug 4 therein. In such embodiments, the carousel 102 containing the abuse deterrent device 2 is a separate unit which may be inserted into the housing 1. In some embodiments, the carousel 102 is disposable. In some embodiments, the housing 1 is reusable.

Figure 21:
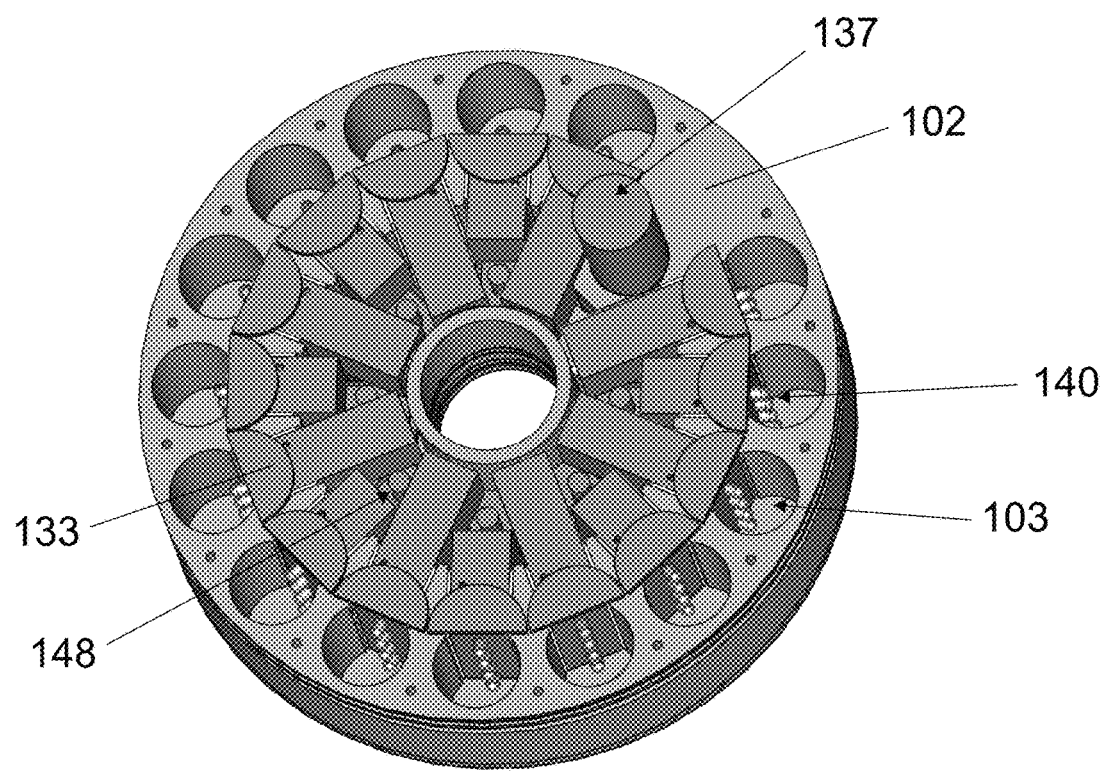
FIG. 21 schematically shows an alternative view of parts within the abuse deterrent device that is removable from and may be used apart from a reusable drug housing in accordance with illustrative embodiments of the invention, as shown in FIGS. 16-20.
Figure 22:
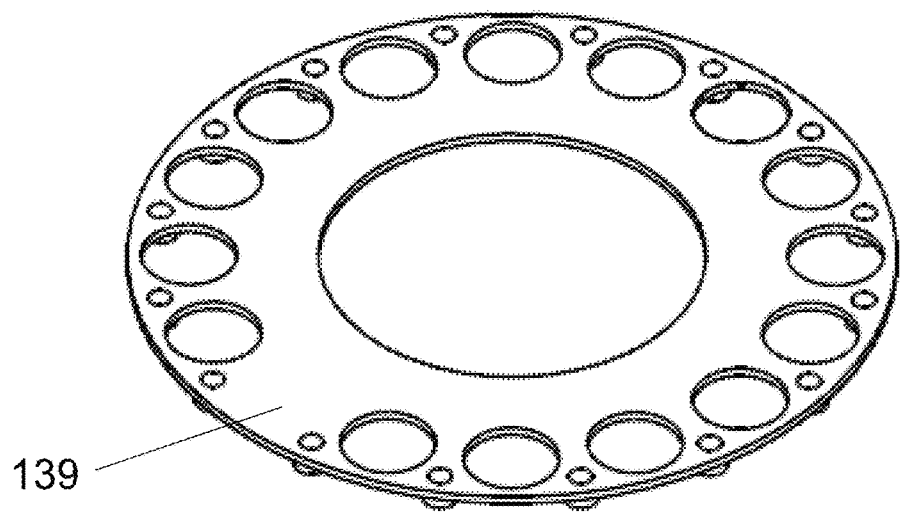
FIG. 22 schematically shows an alternative view of the cover to the abuse deterrent device and carousel in accordance with illustrative embodiments of the invention, as shown in FIGS. 16-21.

In some embodiments, the walls 5 of the housing 1 may be hollow and under negative pressure, such as by vacuum. In some embodiments, the abuse deterrent device 2 or the carousel 102 may also be under negative pressure, such as by vacuum. In some embodiments, the abuse deterrent substance 34 is contained in a multitude of independent compartments adjacent to the spaces 103 housing the drug 4. In some embodiments, the abuse deterrent substance 34 is contained in an independent compartment for each medicine 4 dosage. The spaces 103 may hold the medicine 4 vertically or horizontally. In some embodiments, the carousel 102 includes a piston 133 attached to each of the spaces 103. In such embodiments, the piston 133 is maintained in the inactive, or open, position when the housing 1, carousel 4, and/or abuse deterrent device 2 is under negative pressure or vacuum. As shown in FIGS. 21 and 22, when the negative pressure or vacuum is released in the walls 5 of the housing 1, the abuse deterrent device 2, the carousel 102, or any combination thereof, each piston 133 is activated, moving into the spaces 103 which house the drug 4, and crushing the drug 4. In some embodiments, each piston 133 includes one or more protrusions 140, such as spikes, on its tip, which aid in crushing the drug 4. In some embodiments, each piston 133 includes a compartment 134 which contains the abuse deterrent substance 34. In such embodiments, when the piston 133 is activated, crushing the drug 4, the abuse deterrent substance 34 is released into the space 103 housing the drug 4. In some embodiments, the pistons 133, partially or fully close each space 103, hindering or preventing access to or removal of the crushed drug 4. In some embodiments, the pistons 133 are spring-loaded with compressed springs 86 contained within one or more spring holders 147. In some embodiments, the spring-loaded pistons 133 are maintained in the open, or inactive, position by a retainer line 135. In some embodiments, the pistons 133 are maintained in the open, or inactive, position by another mechanism, such as by, for example, a magnet, a latch, a retaining ring, a peg, or a compressive force.

Figure 20:
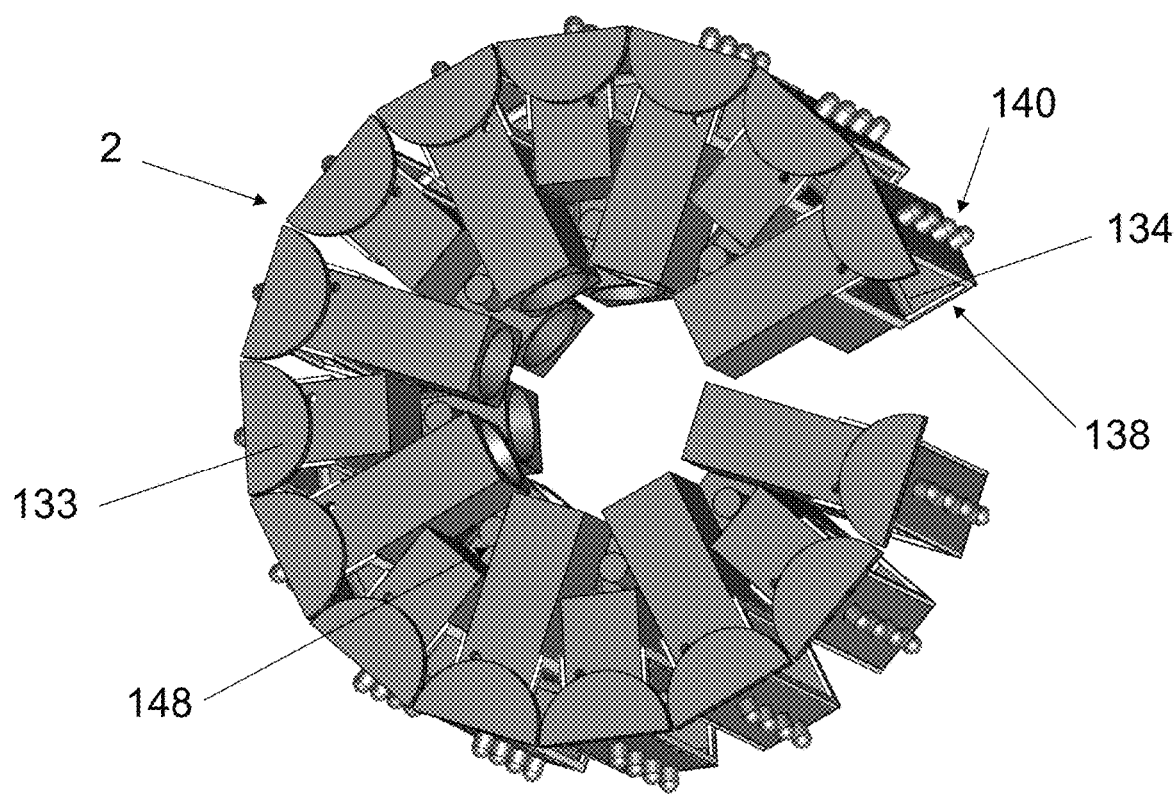
FIG. 20 schematically shows an alternative view of the abuse deterrent device in accordance with illustrative embodiments of the invention, as shown in FIGS. 16-19.
Figure 24:
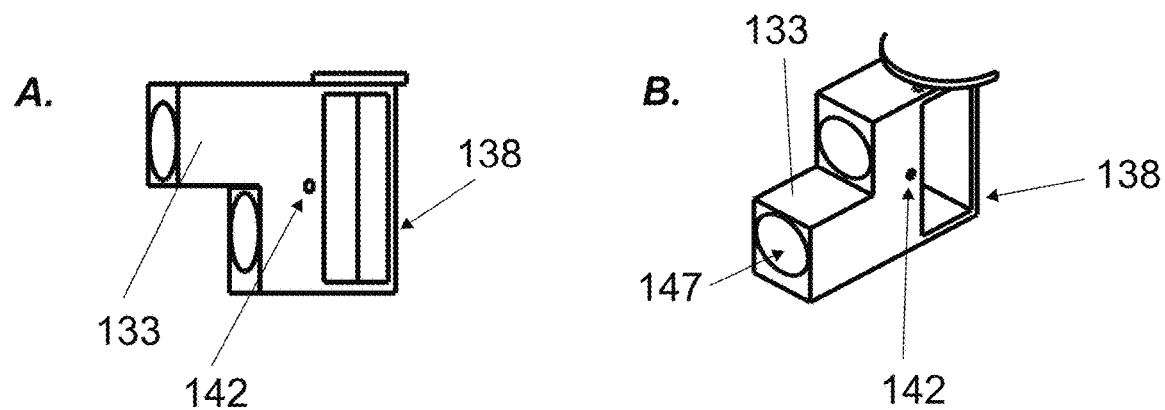
FIG. 24 schematically shows alternative views A and B of pistons within the abuse deterrent device in accordance with illustrative embodiments of the invention, as shown in FIGS. 16-23.

If the drug 4 is improperly accessed (e.g., by cutting through the walls 5 or breaking or cutting into the lid 70), the negative pressure inside the walls 5 of the housing 1 is reduced or released. In illustrative embodiments, cutting through the walls 5 causes the pressure inside the walls 5 to equalize with pressure outside the walls 5. In some embodiments, the release of vacuum releases a blade 136, which cuts the retainer line 135, releasing the spring-loaded pistons 133, crushing the drug and, in some embodiments, releasing the abuse deterrent substance 34 into the spaces 103 containing the crushed drug 4. In some embodiments, the retainer line 135 is inserted into a channel 142 in each piston 133, preventing the pistons 133 from releasing until the retainer line 135 is cut (FIG. 24). In some embodiments, the retainer line 135 is wound around pegs 148 on each piston 133, preventing the pistons 133 from releasing until the retainer line 135 is cut (FIGS. 20 and 21). In some embodiments, the retainer line 135 may be cut by pushing a trigger 137 located on the carousel 102. Manually pushing the trigger 137 will release the spring-loaded pistons 133, crushing the drug and, in some embodiments, releasing the abuse deterrent substance 34 into the spaces 103 containing the crushed drug 4, even if the negative pressure or vacuum has not been reduced or released.

Figure 16:
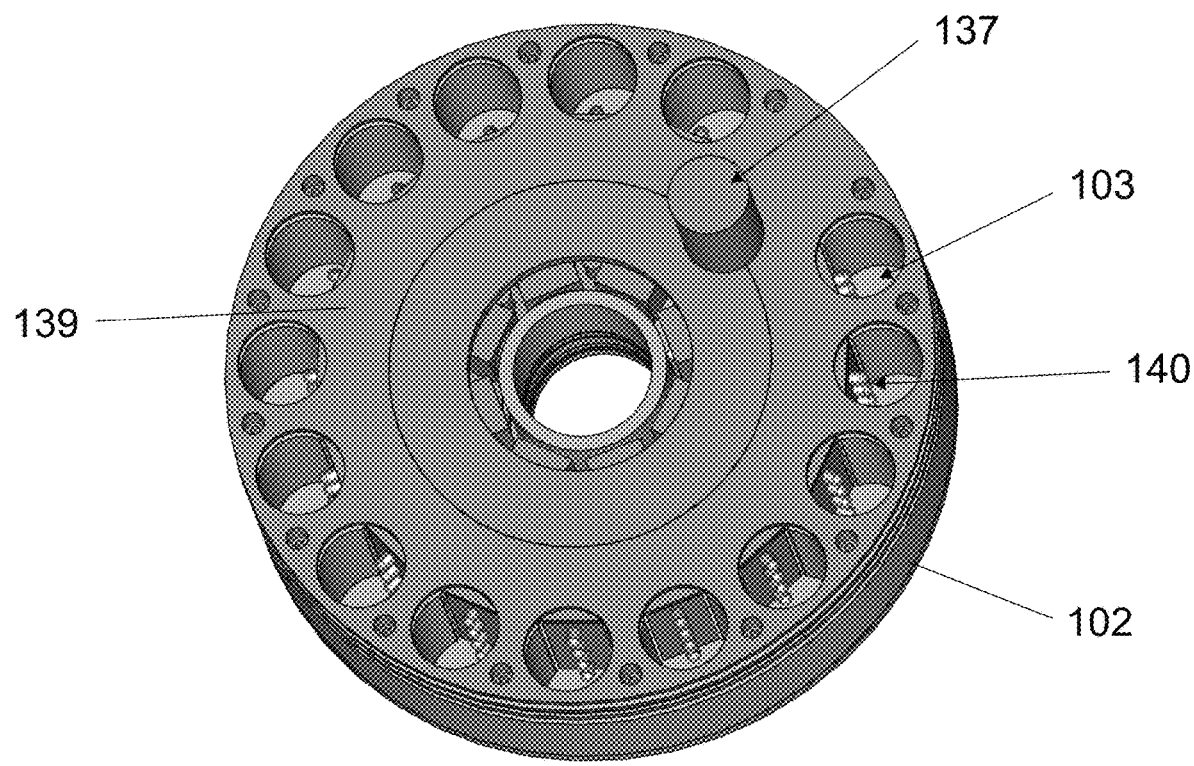
FIG. 16 schematically shows an alternative embodiment of the abuse deterrent device that is removable from and may be used apart from a reusable drug housing in accordance with illustrative embodiments of the invention.
Figure 28:
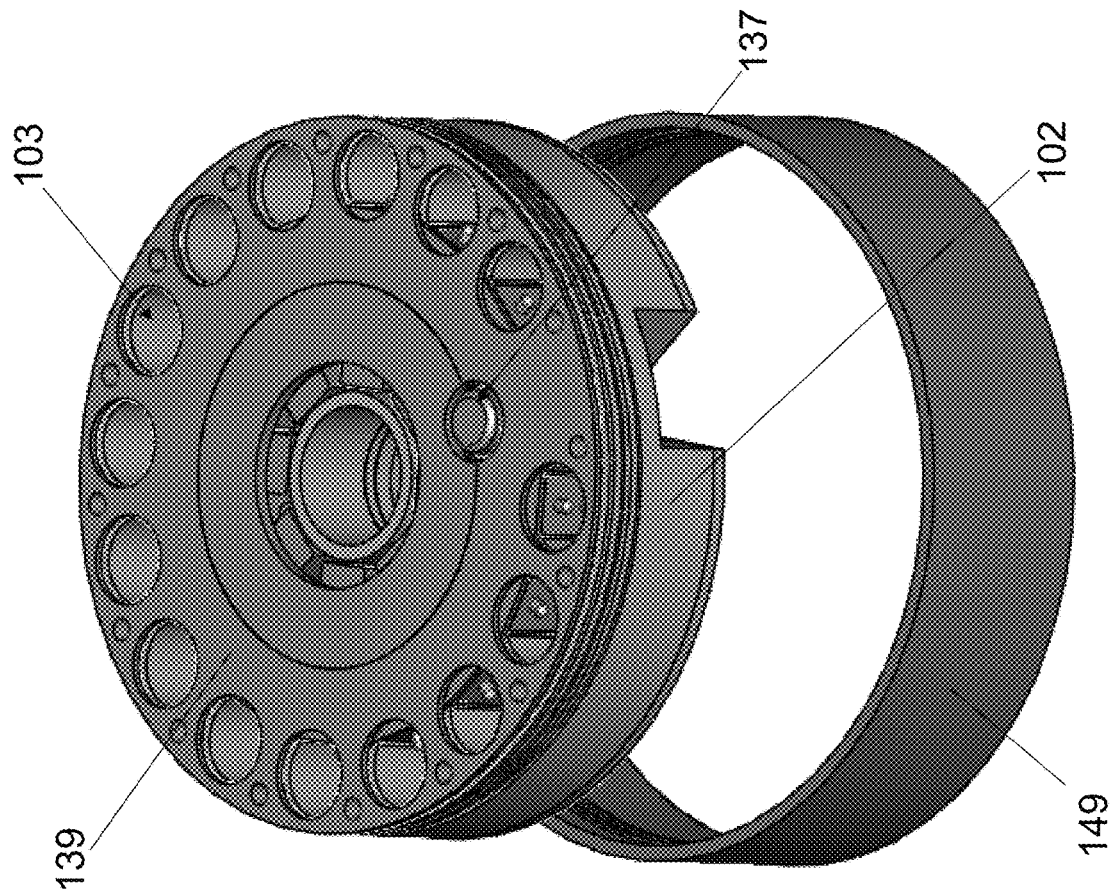
FIG. 28 schematically shows an alternative view of the abuse deterrent device that may be used apart from a reusable drug housing and inserted into a protective case in accordance with illustrative embodiments of the invention.
Figure 27:
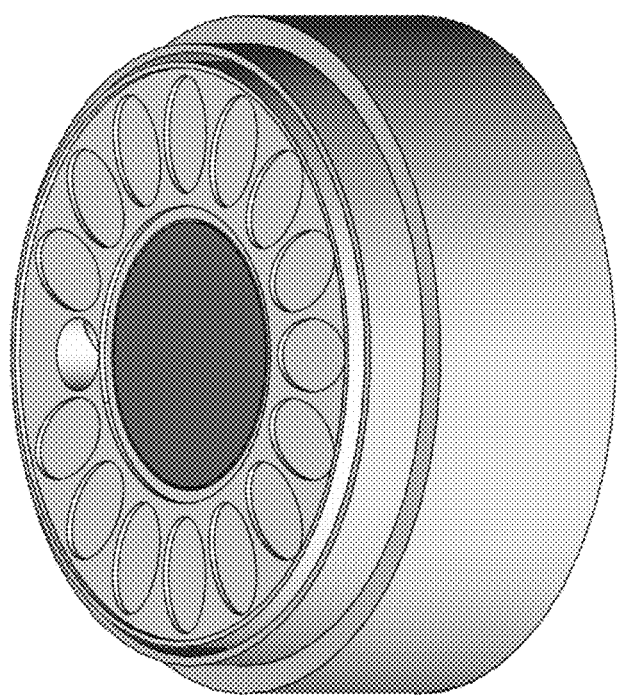
FIG. 27 schematically shows an isometric view of the abuse deterrent device that is inserted into a drug housing and assembled in accordance with illustrative embodiments of the invention, as shown in FIGS. 16-26.

In some embodiments, the abuse deterrent device 2 or carousel 102 does not need to be inserted into the housing for the trigger 137 to be pressed. In such embodiments, the carousel 102 which contains the abuse deterrent device 2 may be used separately without the housing 1 (FIGS. 16, 28). The trigger 137 may be depressed manually to release the spring-loaded pistons 133, crushing the drug and releasing the abuse deterrent substance 34 into the spaces containing the crushed drug 4. Such embodiments enable safe and cost-effective destruction and disposal of any unused or remaining medicine 4 within the spaces 103 of the carousel 102 by, for example, a patient, a pharmacy, or a physician's office.

In some embodiments, the carousel 102 containing the abuse deterrent device 2 may be inserted into a protective case 149 (FIG. 28). In some embodiments, the protective case 149 includes ridges on the inside wall of the protective case 149 which line up with ridges on the outside of the carousel 102. In illustrative embodiments, the protective case 149 protects the sides of the carousel 102. However, the protective case 149 may also protect the bottom and/or the top of the carousel 102. In embodiments where the protective case 149 protects the top of the carousel 102, the protective case 149 may be solid or include cutouts to enable access to each space of the carousel 102 capable of holding the drug 4. The protective case 149 may be made of any acceptable material. In some embodiments, the protective case 149 is made of HDPE (high-density polyethylene), polypropylene, polyethylene terephthalate, high density polyethylene, polyvinyl chloride, polystyrene, or polylactide, and may be made of any color.

The piston 133 may be formed from any pharmaceutically acceptable material. In some embodiments the piston may be formed from stainless steel, high carbon steel, polycarbonate, or plastics. In some embodiments, the one or more openings of the compartment which hold the abuse deterrent substance 34 is surrounded by a washer 138, which prevents the abuse deterrent substance 34 from leaking into the spaces 103 containing the drug 4 while the piston 133 is in the inactive position. Such a washer 138 may be made of any pharmaceutically acceptable material. In some embodiments, the washer 138 may be formed from one or more of fluoropolymers, silicone, resins, polypropylene, or polyethylene terephthalate. In some embodiments, the washer 138 may also aid in reducing friction of the pistons 133 when in the active position, moving into the spaces 103 and crushing the drug 4.

Figure 23:
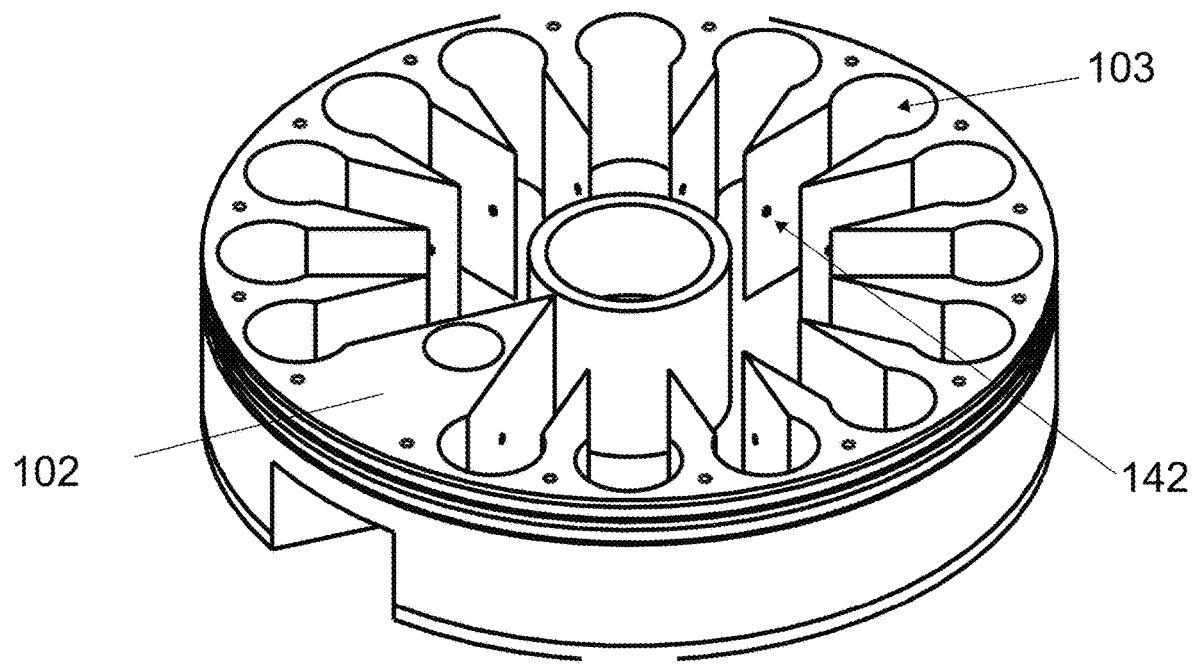
FIG. 23 schematically shows an alternative view of the carousel without the abuse deterrent device inserted in accordance with illustrative embodiments of the invention, as shown in FIGS. 16-22.

Like many containers that hold medication 4, the housing 1 has a lid 70. In some embodiments, the lid 70 is clear, which provides a benefit of easy visibility to load the medication 4 and determine quantity of medication 4 remaining in the container. In some embodiments, the lid 70 includes an access port 29, through which the medication 4 may be loaded and/or dispensed. (FIG. 23). In some embodiments, the lid 70 includes indentations 141 to aid in loading the proper number of doses of medicine 4 into the spaces 103. In some embodiments, the hollows walls 5 and the lid 70 are fluidly connected (e.g., by a tube 81, as shown in FIG. 1) to form a connected uniform pressure. Thus, even if the user cuts through the lid 70, the reduction in negative pressure activates the release of the deterrent substance. In some embodiments, the hollow walls 5 of the housing 1, the lid 70, the carousel 102, and/or the blade 136 are connected such that tampering with any one of these results in cutting the retainer line 135, which activates the piston 133 and releases the abuse deterrent substance 34 into the spaces 103 containing the medication 4.

Some embodiments include a button which must be depressed to access the medication 4. In some embodiments, the button is located on the housing 1. In some embodiments, the button is located on the lid 70. In some embodiments the button may be many buttons, a touch screen, a biomentric sensor, and/or a wireless receiver. The term button is simply an illustrative term and not intended to limit the ways a user may attempt to unlock or access the drug.

Figure 17:
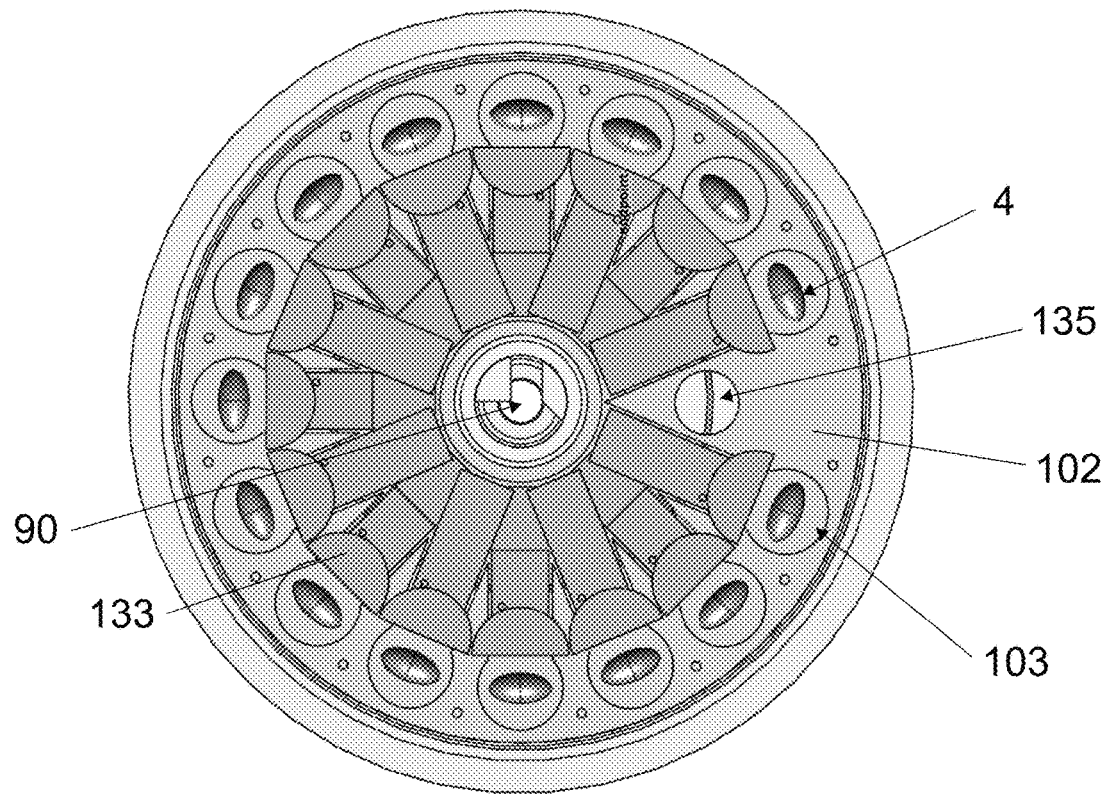
FIG. 17 schematically shows an alternative view of the abuse deterrent device that is inserted into a drug housing in accordance with illustrative embodiments of the invention, as shown in FIG. 16.
Figure 18:
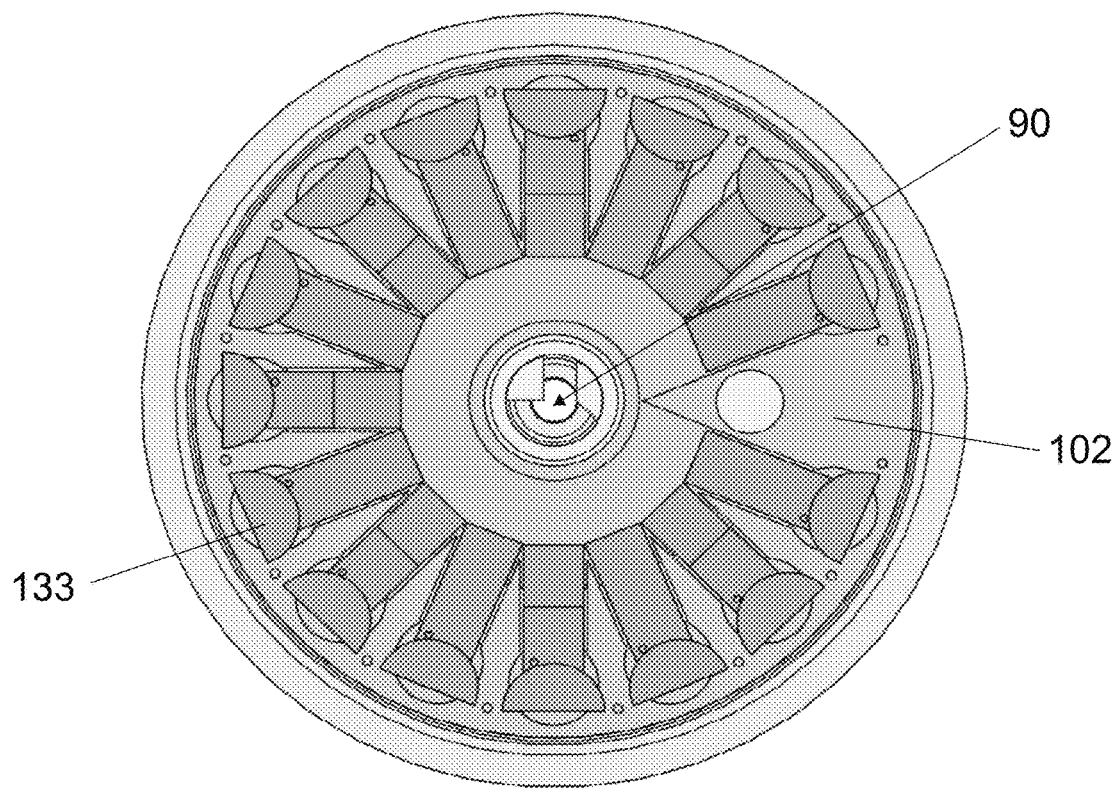
FIG. 18 schematically shows the device of FIG. 17 in an activated position in accordance with illustrative embodiments of the invention, as shown in FIGS. 16-20.
Figure 19:
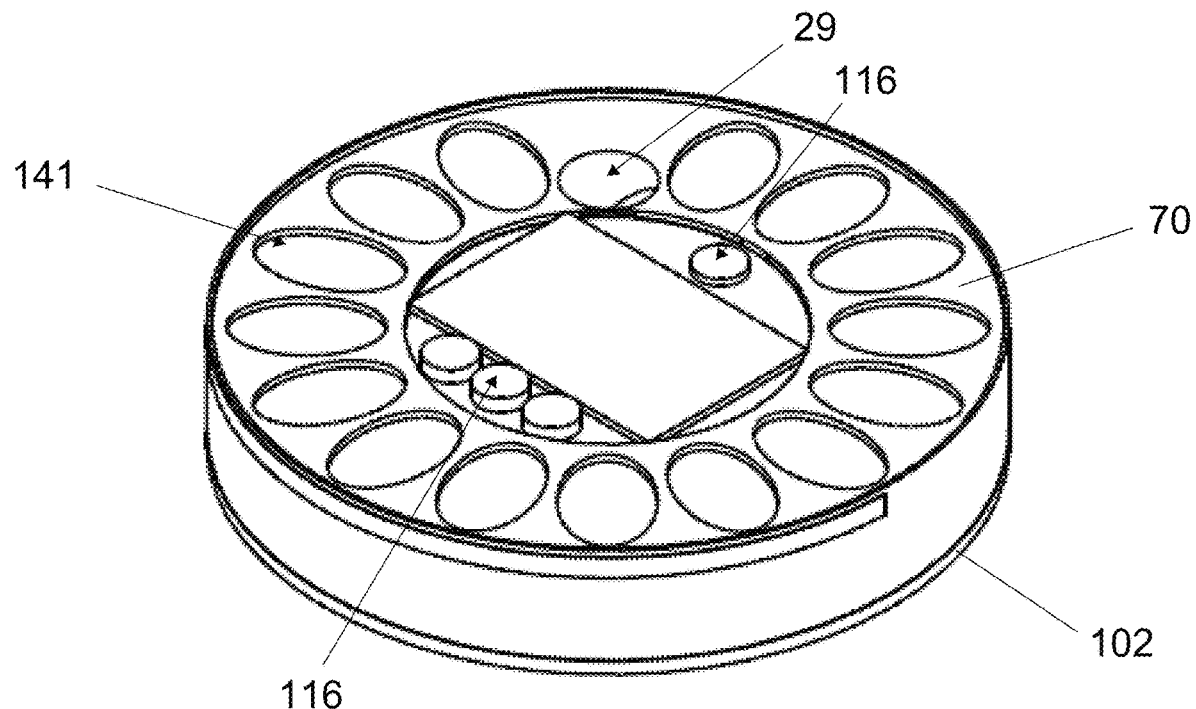
FIG. 19 schematically shows an alternative view of the lid of the device in accordance with illustrative embodiments of the invention, as shown in FIGS. 16-18.
Figure 25:
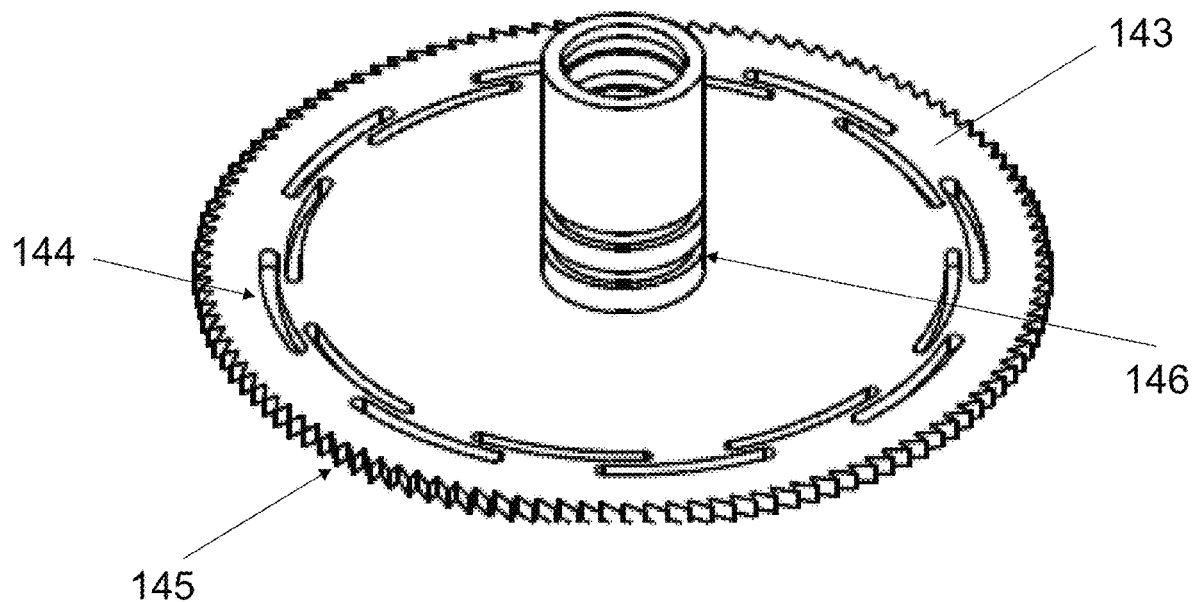
FIG. 25 schematically shows an alternative view of the positioner, in accordance with illustrative embodiments of the invention, as shown in FIGS. 16-24.
Figure 26:
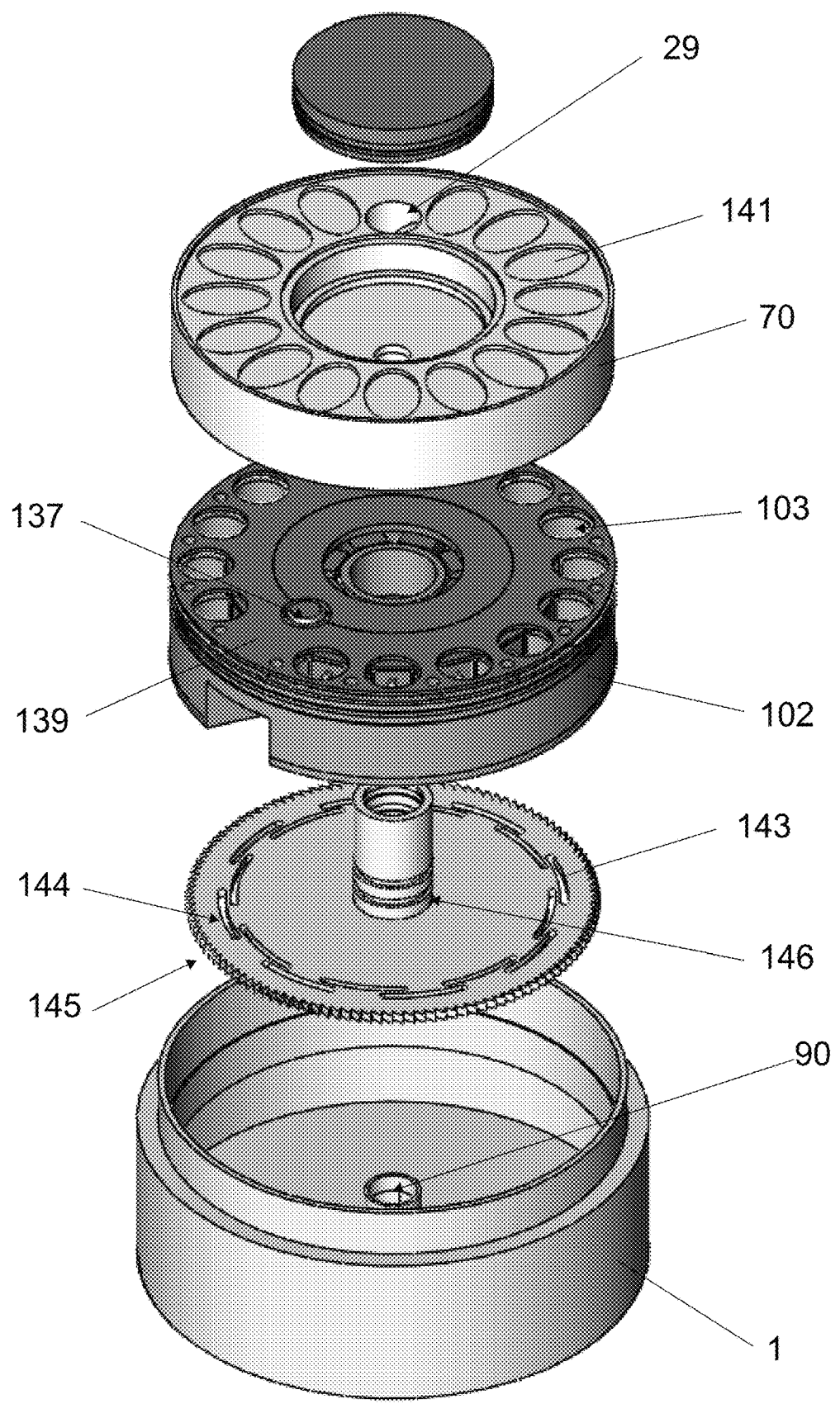
FIG. 26 schematically shows an alternative view of the abuse deterrent device that is inserted into a drug housing in accordance with illustrative embodiments of the invention, as shown in FIGS. 16-25.

In some embodiments, the carousel has spaces 103 for multiple dosage units (as shown in FIGS. 17, 19 and 21). However, the carousel may have more or less spaces 103. Not all the spaces 103 need to be filled by medicine 4. In some embodiments, the spaces 103 may be angled and/or elongated to prevent tampering or improper access of the medication 4. In some embodiments, the carousel 102 contains a fixed quantity unit of a drug or unit of use, and is packaged in 5, 10 or 15 counts of medication 4. In some embodiments, the medication 4 is placed into the spaces 103 of the carousel 102 before covering the top of the carousel 102 with pharmaceutical foil (not shown) to keep the pistons 133 in place and/or prevent direct access to the drug 4. In some embodiments, a cover 139 (FIG. 22) is attached to the filled carousel 102 to keep the pistons 133 in place. In some embodiments, the pharmaceutical foil is affixed to the cover 139 before attaching the cover 139 to the filled carousel 102. In some embodiments, the cover 139 is provided with the pharmaceutical foil already affixed to it. In some embodiments, the medication 4 may be placed into the carousel 102 by a pharmaceutical manufacturing or packaging facility. In some embodiments, the medication 4 may be placed into the carousel 102 by a physician or a pharmacist. The disposable, filled carousel 102 may then be inserted into the reusable housing 1 prior to distributing to physician's offices, pharmacies and/or patients. Alternatively, as previously described, the disposable, filled carousel 102 may be distributed to physician's offices, pharmacies and/or patients as prescribed, for use without the housing 1. In illustrative embodiments, once the lid 70 is closed, it cannot be opened without causing the abuse deterrent substance to deploy, even if the button 116 is depressed or the passcode is correctly entered (e.g., because the button and/or the passcode rotate the carousel 102—they do not open the lid 70). In some embodiments, the carousel 102 rotates in one direction only. In such embodiments, a positioner 143 is attached to the housing 1 and the carousel 102 is affixed on top of the positioner 143 (FIGS. 25 and 26). The slots 44 and/or teeth 145 in the positioner 143 only allow the positioner 143, carousel 102 and lid 70 to rotate in one direction to the next space 103 in the carousel 102. In some embodiments, the positioner 143 may contain one or more o-rings 146, which may provide a fluid connection between the housing 1, the positioner 143, the carousel 102, and the lid 70.

In some embodiments there is no motor 96. In these embodiments pressing the button 116 may allow for the manual rotation of the carousel within the housing 1. In some embodiments, pressing the button 116 unlocks the carousel 102 for about one second, or about five seconds, or about ten seconds, or about twenty seconds, or about thirty seconds, or about forty-five seconds, or about one minute, or about two minutes, or about three minutes, or about four minutes, or about five minutes, or for an unlimited period of time. In some embodiments pressing the button does not automatically rotate the carousel 102, but rather unlocks the carousel 102 to allow for manual rotation.

In some embodiments the device has sensors that will activate the release of the deterrent substance if tampering is detected. Illustrative sensors may detect immersion in water, inversion, shaking, freezing, heating, and or forcing the access port. In some embodiments the access port 29 is elongated and/or angled to prevent improper access of the drug 4. In some embodiments the port 29 is made of a material that will easily break or tear if manipulation of the port 29 is attempted. Example materials include foil or glass.

Figure 29:
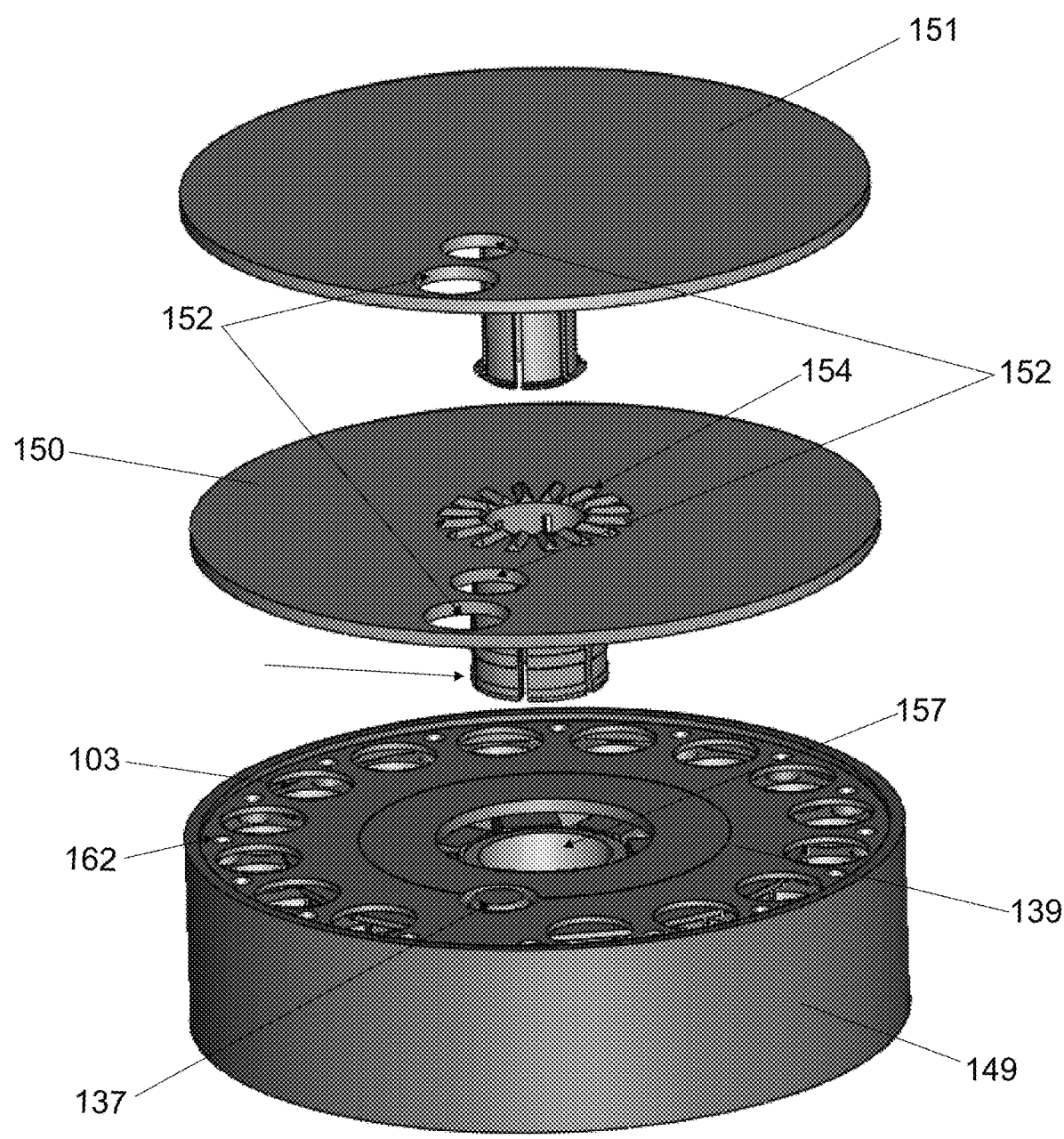
FIG. 29 schematically shows an alternative embodiment of the abuse deterrent device that includes a child-resistant cap in accordance with illustrative embodiments of the invention, as shown in FIGS. 16 and 28.
Figure 30:
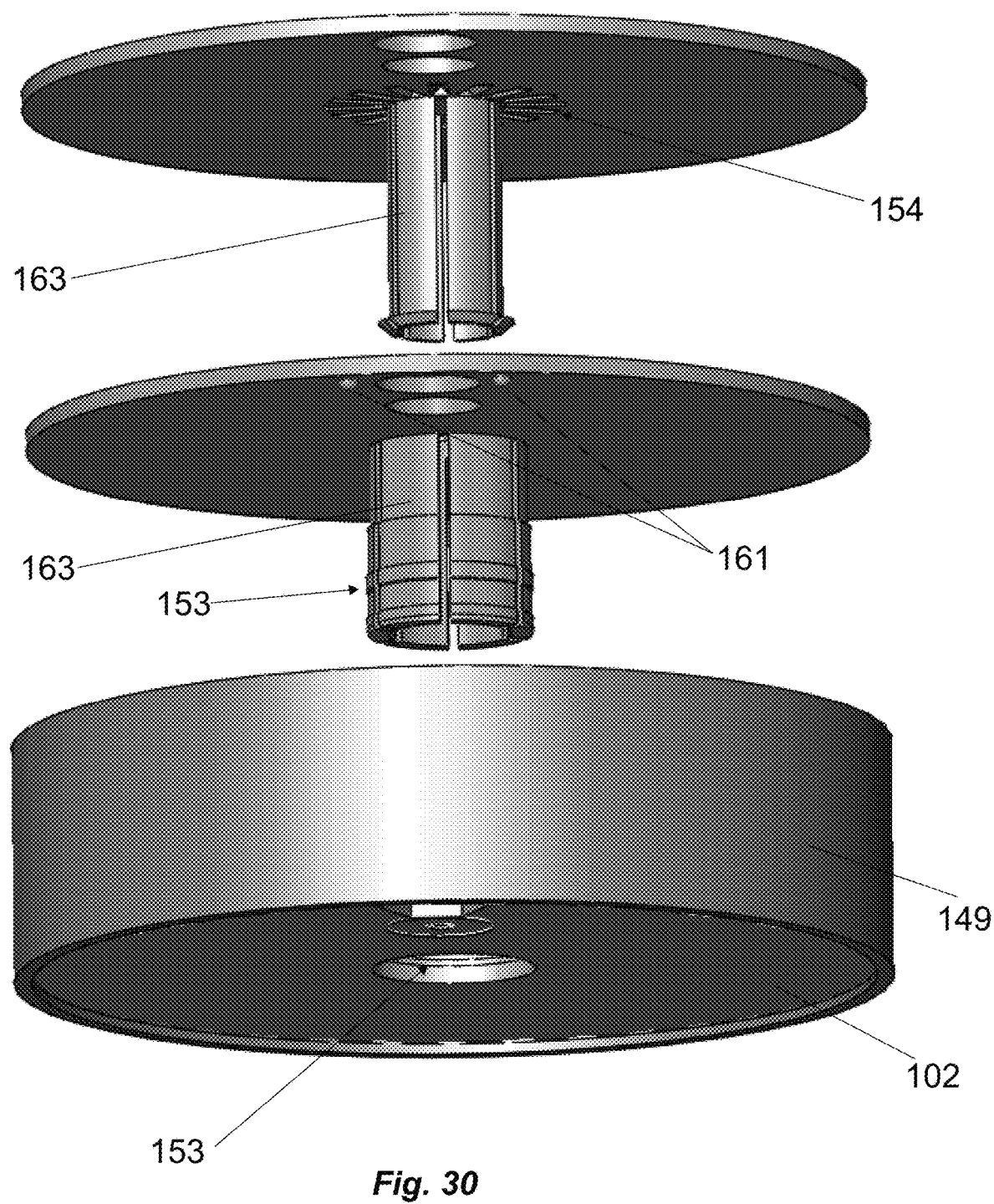
FIG. 30 schematically shows an alternative view of the abuse deterrent device that includes a child-resistant cap in accordance with the illustrative embodiments of the invention, as shown in FIGS. 26, 28 and 29.

In embodiments where the carousel 102 is intended for use without the housing 1, as described above, a child-resistant cap may be attached to the carousel 102 or to the cover 139 attached to the carousel 102. In some embodiments, as shown in FIGS. 29 and 30, the child-resistant cap is a two-piece cap with a lower piece 150 and an upper piece 151. A lower piece 150 of the child-resistant cap includes a tubular projection 163 in the center which is inserted into and attaches to the center 157 of the carousel 102. The outer surface of the tubular projection 163 on the lower piece 150 of the child-resistant cap includes one or more striations 153 such that the lower piece 150 is securely affixed to the carousel 102 and does not normally rotate around the carousel 102. In some embodiments, the bottom surface of the lower piece 150 further includes one or more raised protrusions 161 that interact with and fit into holes 162 on the cover 139, the holes 162 being located on each side of a space 103. The top surface of the lower piece 150 further includes ridges, teeth, grooves or slots 164 around the opening for the tubular projection 163. An upper piece 151 of the child-resistant cap also includes a tubular projection 163 in the center which is inserted into and attaches to the tubular projection 163 of the lower piece 150. The bottom surface of the upper piece 151 of the child-resistant cap further includes raised ridges or teeth 154 around the base of the tubular projection 163. In some embodiments, both the lower piece 150 and the upper piece 151 of the child-resistant cap include an access port 152 which may be lined up, respectively. When the respective access ports line up, a drug dose may be dispensed through the access port 152. In some embodiments, the upper piece 151 will rotate without rotating the lower piece 150 when the upper piece 151 is not depressed. The lower piece may be rotated by depressing the top of the two-piece cap and turning the two-piece child-resistant cap until the outer access port 152 exposes the next space 103 filled with a drug 4. When the top of the two-piece cap is depressed, the ridges, teeth, grooves or slots 164 on the bottom surface of the upper piece 151 and the raised ridges or teeth 154 on the top surface of the bottom piece 150 interact and the two-piece cap may be turned clockwise or counter-clockwise to the next space 103 filled with a drug 4. In some embodiments, the two-piece cap may also include a second access port 152 that may line up with the trigger 137. When the trigger 137 is exposed, it may be manually depressed to release the spring-loaded pistons 133, crushing the drug and releasing the abuse deterrent substance 34 into the spaces containing the crushed drug 4. In such embodiments, this allows for safe and effective disposal of unused or unneeded drug 4 doses.

Figure 31:
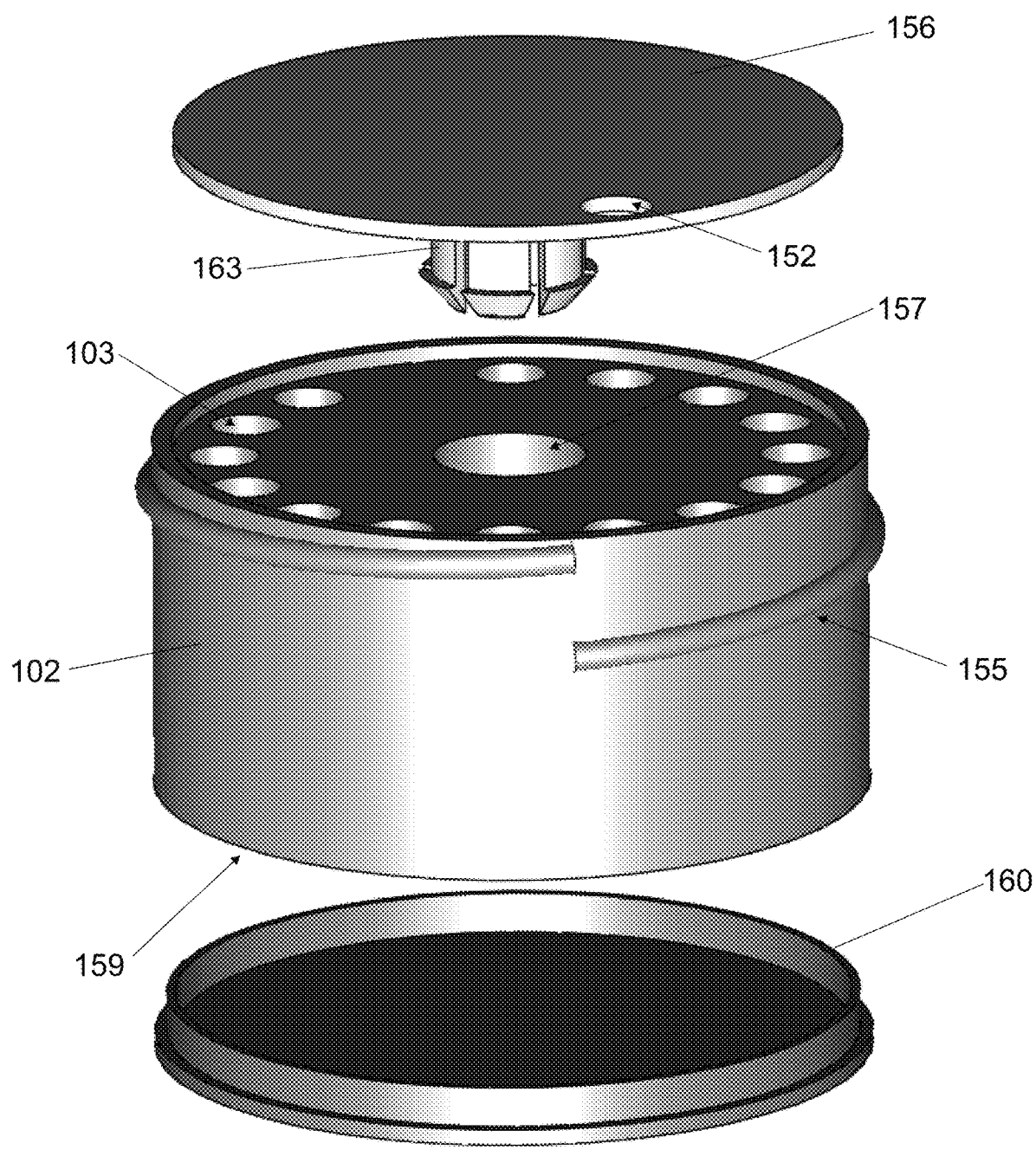
FIG. 31 schematically shows an alternative embodiment of a fixed quantity unit of use device that includes a child-resistant cap in accordance with illustrative embodiments of the invention.
Figure 32:
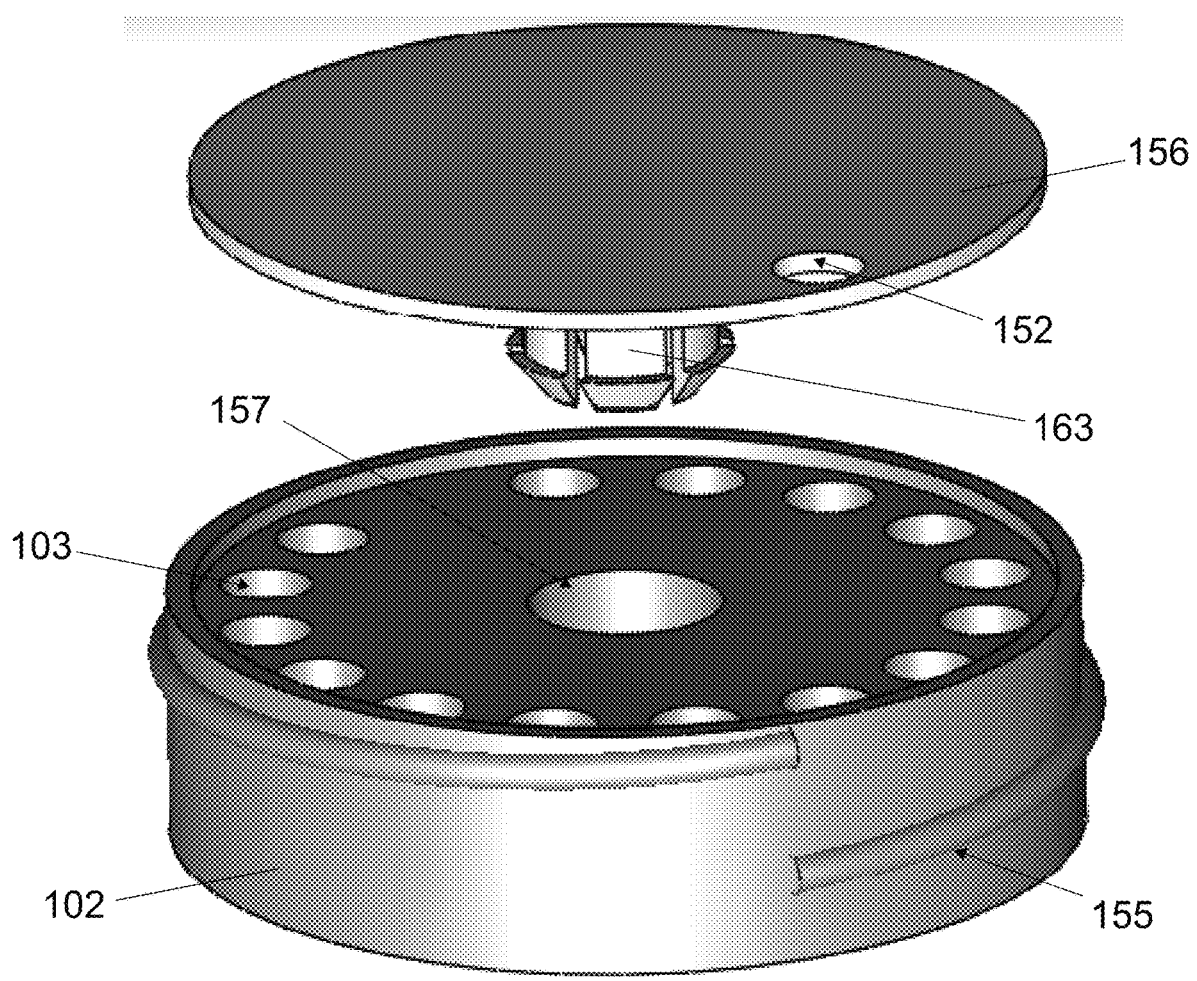
FIG. 32 schematically shows an alternative embodiment of the fixed quantity unit of use device that includes a child-resistant cap in accordance with illustrative embodiments of the invention, as shown in FIG. 31.
Figure 34:
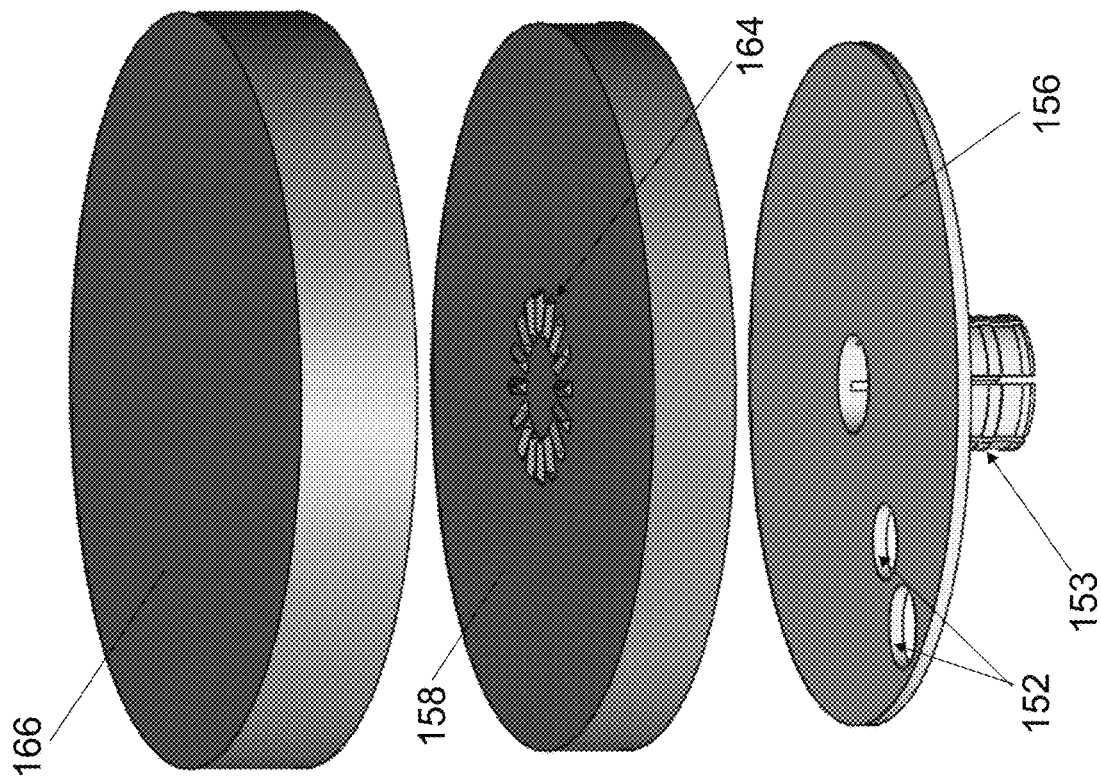
FIG. 34 schematically shows an alternative view of the child-resistant cap in accordance with illustrative embodiments of the invention, as shown in FIGS. 31-33.
Figure 33:
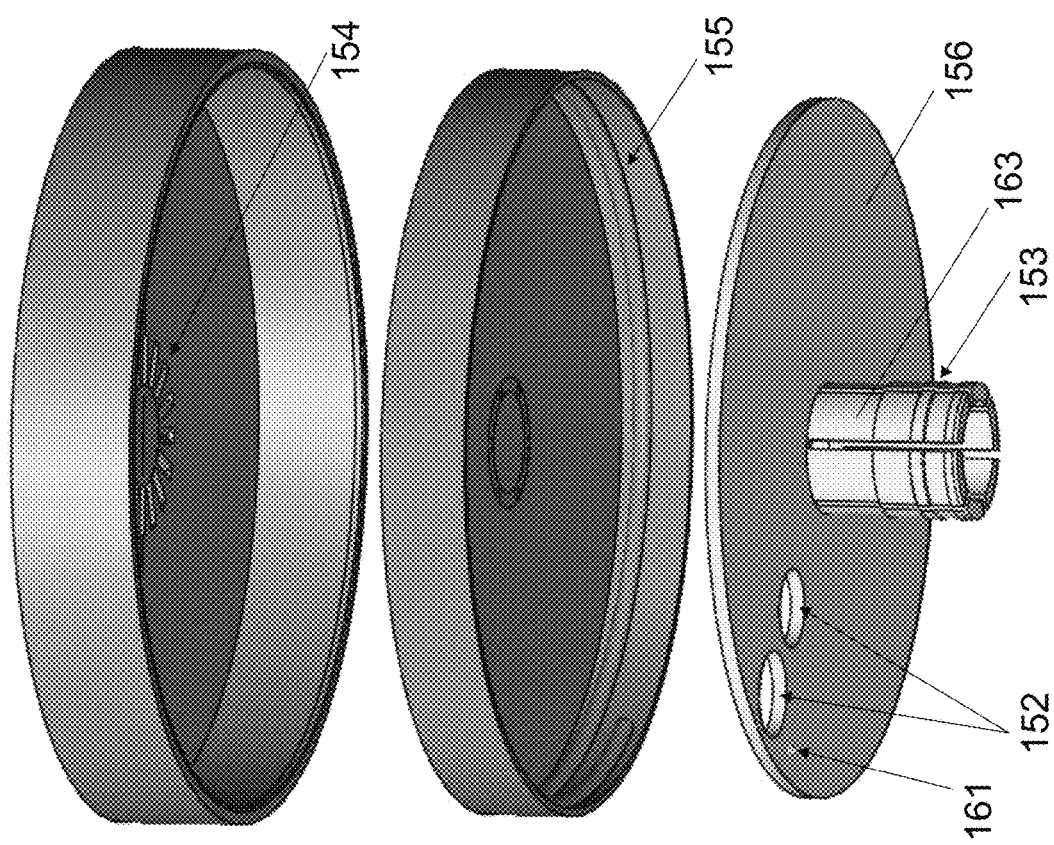
FIG. 33 schematically shows an alternative embodiment of the child-resistant cap in accordance with illustrative embodiments of the invention, as shown in FIGS. 31 and 32.
Figure 35:
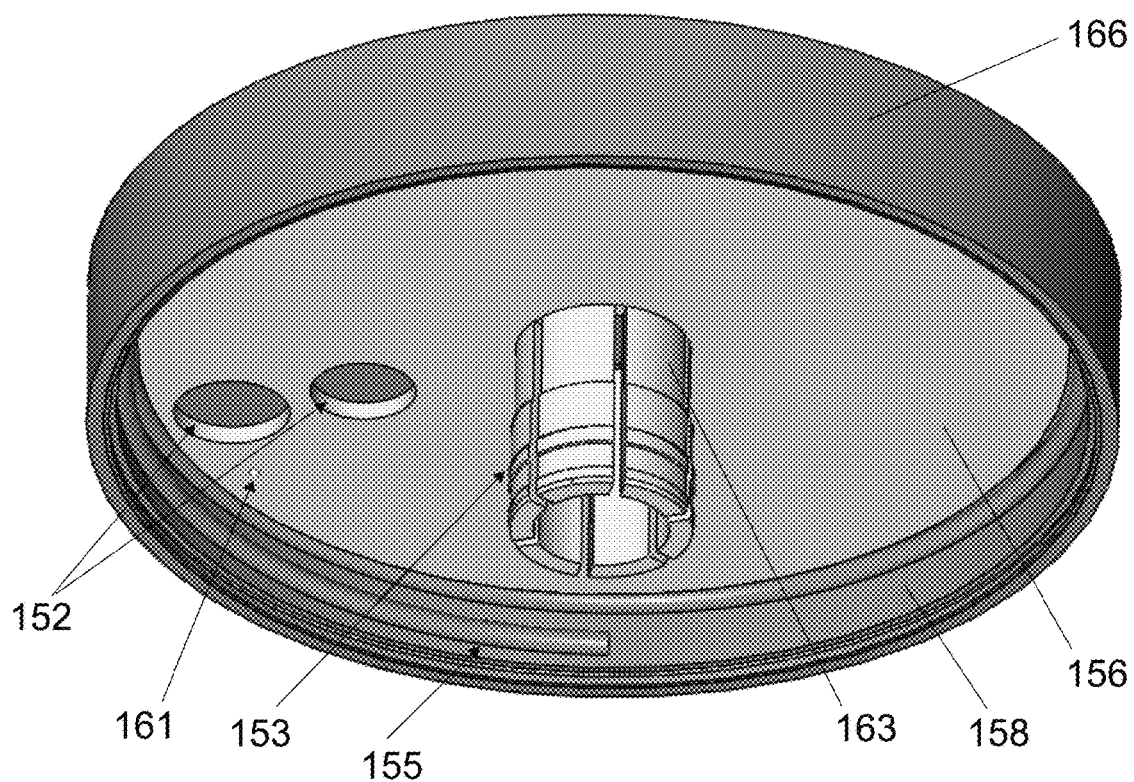
FIG. 35 schematically shows an alternative view of the child-resistant cap in accordance with illustrative embodiments of the invention, as shown in FIGS. 31-34.
Figure 36:
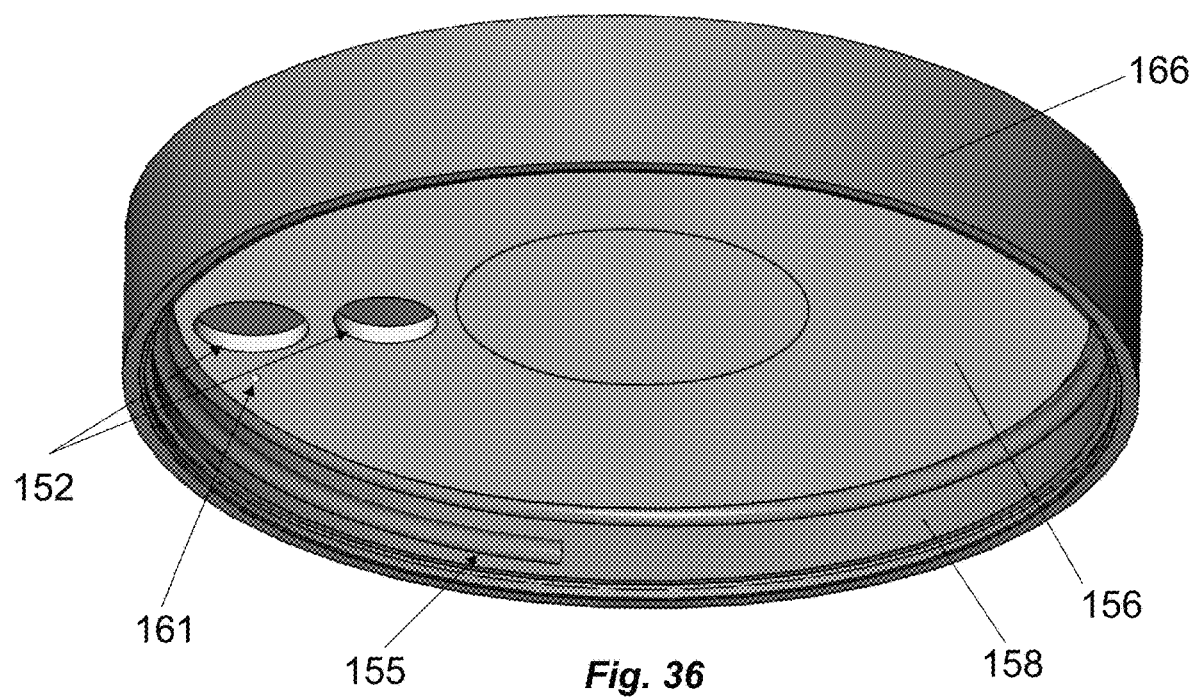
FIG. 36 schematically shows an alternative embodiment of the child-resistant cap in accordance with illustrative embodiments of the invention.
Figure 37:
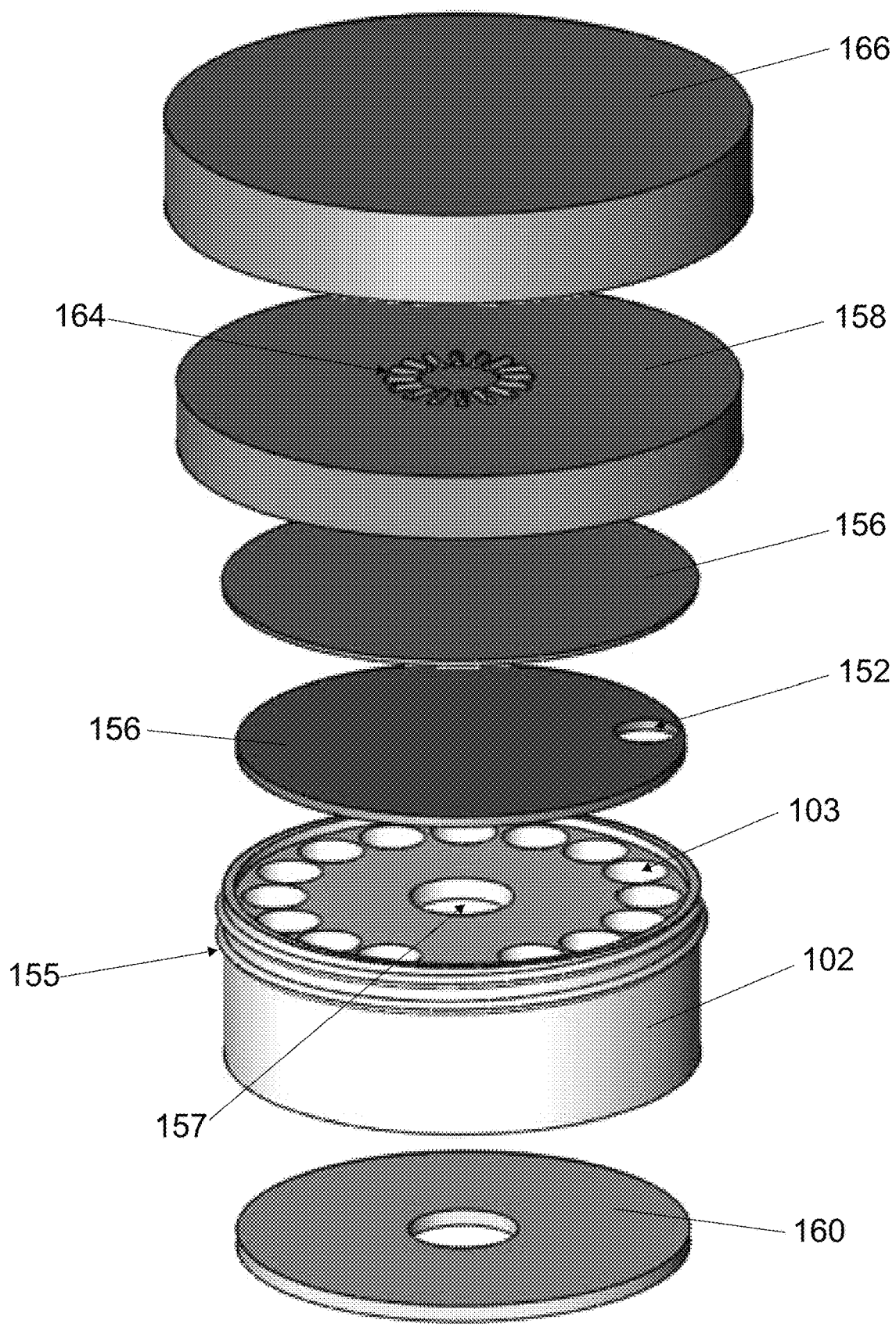
FIG. 37 schematically shows an alternative embodiment of a fixed-quantity unit of use device that includes a child-resistant cap in accordance with the illustrative embodiments of the invention.
Figure 38:
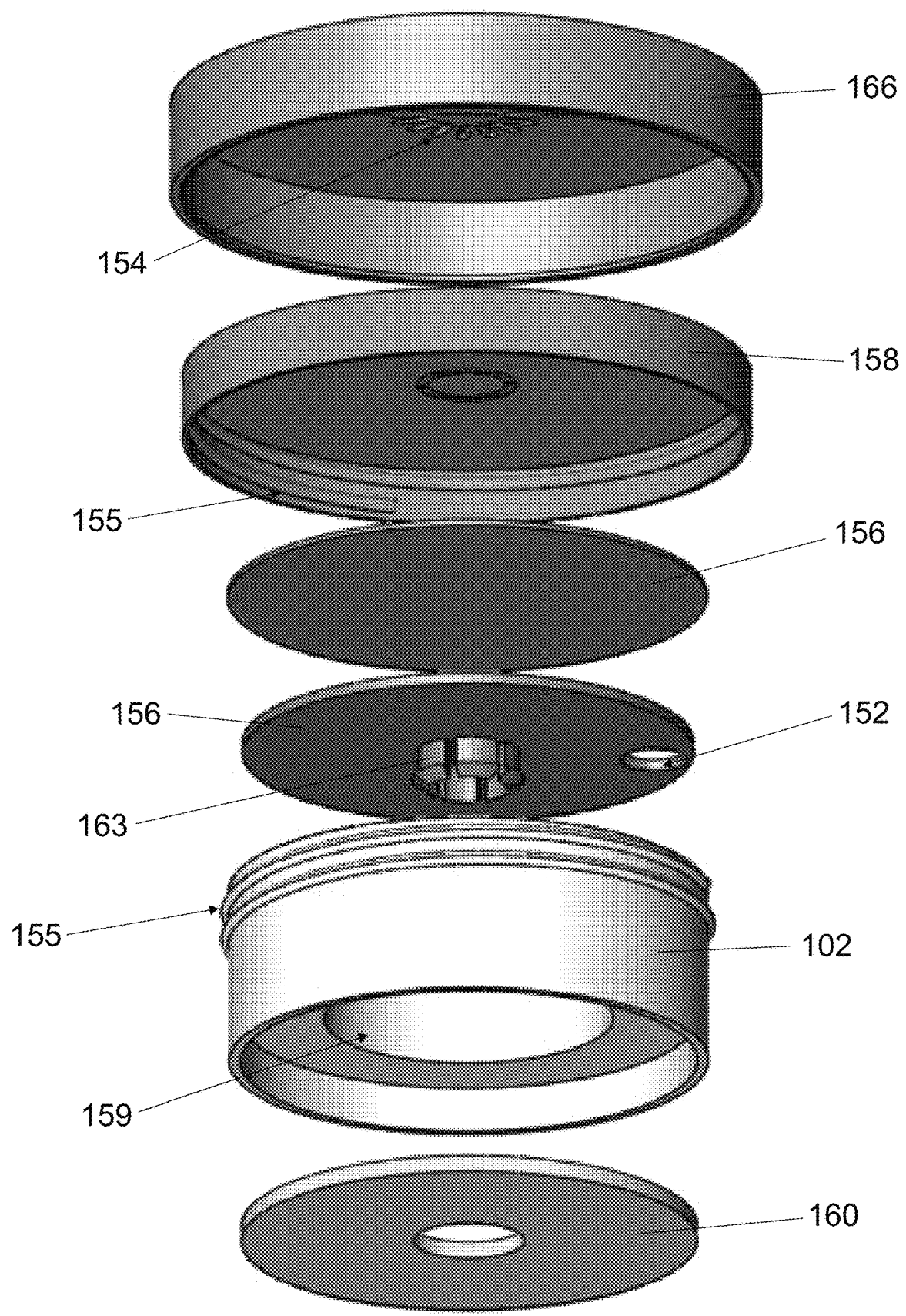
FIG. 38 schematically shows an alternative view of a fixed-quantity unit of use device that includes a child-resistant cap in accordance with the illustrative embodiments of the invention, as shown in FIG. 37.

In some embodiments, a multi-piece child-resistant cap may be attached to the carousel 102. In such embodiments, the carousel 102 includes threading 155 on the outer surface of the carousel 102. In some embodiments, the child-resistant cap is a four-piece cap. In some embodiments, the child-resistant cap is a three-piece cap. In some embodiments, a first piece 156 of the multi-piece child-resistant cap includes a tubular projection 163 in the center, wherein the tubular projection 163 is inserted into and attaches to the center 157 of the carousel 102. In some embodiments, the first piece 156 of the child-resistant cap does not include a tubular projection, as shown in FIG. 36. The first piece 156 further includes an access port 152 through which a dose of medication 4 may be dispensed. In some embodiments, the first piece 156 further includes a second access port 152 that is capable of lining up with the trigger 137. When the trigger 137 is exposed, it may be manually depressed to release the spring-loaded pistons 133, crushing the drug and releasing the abuse deterrent substance 34 into the spaces containing the crushed drug 4. In such embodiments, this allows for safe and effective disposal of unused or unneeded drug 4 doses. In some embodiments, the first piece 156 is capable of freely rotating around the center 157 of the carousel 102 to enable the one or more access ports 152 to be aligned with a space 103 containing medication 4 or the trigger 137. In some embodiments, a further portion 158 of the child-resistant cap is attached to the carousel 102 by the threads 155 located on the outside of the carousel 102. In some embodiments, the further portion 158 includes two pieces, an inner cap 165 and an outer cap 166. In such embodiments, threading 155 is included on the inside of the inner cap 165. The top of the inner cap 165 also includes ridges, teeth, grooves or slots 164 around its center, as shown in FIG. 34. In some embodiments, raised ridges or teeth 154 are also included around the center of the bottom of an outer cap 166, as shown in FIG. 33. The inner cap 165 fits securely inside the outer cap 166. In some embodiments, the inner cap 165 may be secured inside the outer cap 166 by one or more features, such as a striation, ridge, lip or other feature that prevents the inner cap 165 from begin removed or separated from the outer cap 166, but allows for or enables some movement of the inner cap 165 within the outer cap 166 when the outer cap 166 is not depressed. In some embodiments, movement of the inner cap 165 includes compression such that the ridges, teeth, grooves or slots 164 on the inner cap 165 interact with the raised ridges or teeth 154 on the outer cap 166. When the raised ridges or teeth 154 interact with the ridges, teeth, grooves or slots 164, the further portion 158 (including the inner cap 165 and the outer cap 166) may be removed by turning in the opposite direction of the threads on the carousel 102. In some embodiments, the second portion 158 is removed by turning in a counter-clockwise direction. After the further portion 158 is removed, the medication 4 may be accessed as indicated above. In some embodiments, the child-resistant cap further includes another piece that is a sealing surface or liner 167 made of a pharmaceutically acceptable material such as polystyrene, polyethylene or compressible polyethylene foam, as shown in FIGS. 37 and 38. In some embodiments, the carousel 102 may include a separate compartment 159 in which a deterrent system may be contained. The deterrent system may be a mail-back or disposal bag. As shown in FIG. 31, the compartment 159 may be located on the bottom of the carousel 102, and may include a removable cap 160 which secures the mail-back or disposal bag. In some embodiments, the removable cap 160 may include a hole 168 to assist in removal of the cap. The mail-back or disposal bag of the deterrent system may be arranged in any manner to fit into the compartment. In some embodiments, the mail-back or disposal bag may be rolled or folded, such that it fits into the compartment. In some embodiments, the carousel 102 is intended for use without the housing 1, and does not contain a chemical deterrent 34 or an abuse deterrent device 2 as described above. As shown in FIGS. 31 and 32, in such embodiments, the carousel 102 includes spaces 103 for the medication 4 and threading 155 on the outer surface of the carousel 102.

The pieces of the child-resistant cap may be made of any pharmaceutically acceptable material, as previously described herein, such as HDPE, polypropylene, polyethylene terephthalate, high density polyethylene, polyvinyl chloride, polystyrene, fluoropolymers, silicone, resins, polypropylene, polyethylene terephthalate and/or polylactide, which may be clear, tinted or opaque.

Although this disclosure includes various exemplary embodiments of the invention, it should be apparent that those skilled in the art can make various modifications that will achieve some of the advantages of the invention without departing from the true scope of the invention.

EXAMPLES

Example 1: Naltrexone Recovered from Small IR Tablets

A solution of naltrexone in 60% Ethanol/40% water at a concentration of 19 mg/ml was achieved without precipitation.

Five (5) small immediate release ("IR") tablets (Homeopathy Blank 5 Grain, Lactose, Lot #: 07090710H3, Exp. 08/23) were individually placed in a small weigh boats and coated with a 10 mg/mL Naltrexone solution prepared in 60% Ethanol/40% water. After 1 minute, one tablet was removed from solution and an assay was performed to test for Naltrexone. This procedure was repeated at 2, 5, 10 and 30 minutes. Results show that Naltrexone was recovered in a range of 1.12 mg to 3.77 mg, which increased along with an increased time in the Naltrexone solution. See Table 1.

TABLE 1

| Small IR Tablet-Recovered Naltrexone | | | |
|---|---|---|---|
| Dosage Form | API | Time (min) | Recovered Naltrexone (mg) |
| Small IR Tablet | Naltrexone Base | 1 | 1.12 |
| | | 2 | 1.09 |
| | | 5 | 1.80 |
| | | 10 | 2.31 |
| | | 30 | 3.77 |

Example 2: Increasing Solubility of Naltrexone Recovered from Small IR Tablets

To determine a formulation which will deposit 3.6-9.6 mg of Naltrexone onto small IR tablets within a specified period of time, the ratio of ethanol to water was adjusted to increase solubility of Naltrexone. Naltrexone was dissolved in ethanol and titrated with water until precipitates formed, resulting in a final ratio of 75:25 ethanol to water, with a final concentration of 37.5 mg/ml Naltrexone solution.

Four (4) small IR tablets (Homeopathy Blank 5 Grain, Lactose, Lot #: 07090710H3, Exp. 08/23) were individually distributed into 2 small weigh boats and 2 test tubes. Each tablet was coated with 37.5 mg/mL of Naltrexone solution (75:25 ethanol to water). After 6 minutes, one tablet was removed from one weigh boat and one test tube each, and an assay was performed to test for Naltrexone. This procedure was repeated at 10 minutes. Results show that Naltrexone was recovered in a range of 4.06 mg to 8.51 mg, with the test tube preparations showing higher recovery than the weigh boats at both time points. See Table 2. The concentration of 37.5 mg/mL Naltrexone solution was adequate to achieve 3.6-9.6 mg of Naltrexone onto tablets within 6 minutes. Higher concentration solutions required an increase of ethanol in the diluent to improve the solubility of Naltrexone Base. This can present challenges relating to the flammability of the formulation. The more water soluble Naltrexone Hydrochloride is a potential option to balance concentration and flammability concerns.

TABLE 2

Small IR Tablet-Recovered Naltrexone

| Dosage Form | API | Time (min) | Container | Recovered Naltrexone (mg) |
|---|---|---|---|---|
| Small IR Tablet | Naltrexone Base | 6 | Weigh Boat | 4.06 |
| | | 6 | Test Tube | 5.32 |
| | | 10 | Weigh Boat | 4.92 |
| | | 10 | Test Tube | 8.51 |

Example 3: Naltrexone Hydrochloride Solubility

To determine the solubility of Naltrexone HCl in solutions of 100% water or 60%/40% Ethanol/water, solutions of Naltrexone HCl were prepared at 50 mg/mL and 100 mg/mL in 100% water or 60%/40% ethanol/water for a total of 4 solutions. Solutions were vortex mixed, placed on a mechanical shaker and evaluated every 30 minutes for complete dissolution. Once fully dissolved, each solution was prepared for HPLC by diluting to 2 mg/mL in methanol and 0.1M phosphoric acid and analyzed on an HPLC.

The 50 mg/mL samples were fully dissolved into solution following 1 hour on the mechanical shaker with periodic vortex mixing. The 100 mg/mL solution prepared in the ethanol/water mixture was dissolved after a total of 2 hours shaking with periodic vertex mixing. The 100 mg/mL solution in 100% water was also sonicated. HPLC results are included in Table 3. These results indicate that Naltrexone HCl is soluble up to 100 mg/mL in 100% water or in a 60%/40% ethanol/water solution.

TABLE 3

HPLC analysis of Naltrexone HCl solubility

| Sample Concentration | Diluent | Solubilized Concentration (mg/mL) |
|---|---|---|
| 50 mg/mL | 100% water | 49.0 |
| | 60:40 Ethanol:water | 48.6 |
| 100 mg/mL | 100% water | 96.9 |
| | 60:40 Ethanol:water | 96.1 |

Example 4: Naltrexone Recovered from Immediate Release and Extended Release Tablets To compare formulations of Naltrexone and Naltrexone HCl which will deposit 3.6-9.6 mg of Naltrexone onto small IR tablets, small extended release ("ER") tablets and large ER tablets, Naltrexone (23 mg/ml) and Naltrexone HCl (23 mg/ml) solutions were used. Six (6) small IR tablets (Homeopathy Blank 5 Grain, Lactose, Lot #: 07090710H3, Exp. 08/23), six (6) small ER Tablets (Mucus Relief Guaifenesin Extended-Release Tablets, 600 mg, Lot #: F07210, Exp. 04/20), and three (3) large ER tablets (Mucus Relief Guaifenesin Extended-Release Tablets, 1200 mg, Lot #: F08474, Exp. 05/20) were tested. Tablets were placed in test tubes or kept in their blister packaging and spiked with a 23 mg/mL spiking solution containing either Naltrexone Base or Naltrexone HCl. Small tablets (IR and ER) were divided into two groups of 3 and coated with a solution prepared with either Naltrexone base (23 mg/ml) or Naltrexone HCl (23 mg/ml). Large ER tablets were spiked with Naltrexone base solution only while remaining in their original blister packaging. Each tablet remained in solution for a period of 2, 6 or 10 minutes before removal and testing form Naltrexone. The large ER tablets spiked with Naltrexone NCl were not completed due to time limitations The results, summarized in Tables 4 and 5, are comparable for Naltrexone base and Naltrexone HCl. Recovered Naltrexone ranged from 6.06-7.50 mg for small IR tablets, 2.48-3.50 mg for small ER tablets, and 2.50-4.72 mg for large ER tablets. Specifically, the small IR tablets began disintegrating by the 2 minute time-point and a small amount of residue remained in the test tube after transfer for analysis. Both sizes of ER tablets did not fully disintegrate while coated in ethanol/water Naltrexone base solution or in the final sample preparation solution consisting primarily of 0.1M phosphoric acid. The results for Naltrexone base and Naltrexone HCl were similar, but the Naltrexone base comes out of solution over time likely due to the lower proportion of ethanol present. Based on results and observations of this experiment, Naltrexone HCl is the preferred API.

TABLE 4

Small IR Tablet-Recovered Naltrexone from Naltrexone base or Naltrexone HCl

| Dosage Form | API | Time (min) | Average Recovered Naltrexone (mg) |
|---|---|---|---|
| Small IR Tablet | Naltrexone Base | 2 | 7.50 |
| | | 6 | 6.91 |
| | | 10 | 6.85 |
| | Naltrexone HCl | 2 | 4.44 |
| | | 6 | 6.06 |
| | | 10 | 6.55 |

TABLE 5

ER Tablet-Recovered Naltrexone from Naltrexone base or Naltrexone HCl

| Dosage Form | API | Time (min) | Average Recovered Naltrexone (mg) |
|---|---|---|---|
| Small ER Tablet | Naltrexone Base | 2 | 2.76 |
| | | 6 | 2.48 |
| | | 10 | 3.50 |
| | Naltrexone HCl | 2 | 2.64 |
| | | 6 | 2.85 |
| | | 10 | 3.45 |
| Large ER Tablet | Naltrexone Base | 2 | 2.50 |
| | | 6 | 3.75 |
| | | 10 | 4.72 |

Example 5 a. Naltrexone Recovered from IR and ER Tablets and Empty Capsules

To determine the approximate time in solution needed to deposit 8 mg or more of Naltrexone onto various tablets and capsules using a 25 mg/mL solution of Naltrexone HCl in 60% Ethanol/40% water, four (4) of each of small IR tablets (Homeopathy Blank 5 Grain, Lactose, Lot #: 07090710H3, Exp. 08/23), small ER tablet (Mucus Relief Guaifenesin Extended-Release Tablets, 600 mg, Lot #: F07210, Exp. 04/20), large ER tablet (Mucus Relief Guaifenesin Extended-Release Tablets, 1200 mg, Lot #: F08474, Exp. 05/20), small capsule (Gelatin, Lot #: XT0702018, Exp. 08/21), and large capsule (Gelatin, Lot #: C1800166792, Exp. 01/23) were distributed amongst test tubes (or scintillation vials for large size tablets). Each tablet or capsule was covered with a 25 mg/mL Naltrexone HCl solution. After 3 minutes, two (2) of each tablet or capsule type were removed from solution and a Naltrexone assay was performed.

Results are summarized in Table 6. No sample category met the objective of recovering 8 mg or more of Naltrexone. The highest recovery was observed for the small IR tablets at 6.11-7.60 mg but low recoveries were noted for both capsule sizes. Both sizes of ER tablets were in the mid-range of results.

TABLE 6

Recovered Naltrexone from IR and ER tablets, and empty capsules

| Dosage Form | API | Time (min) | Average Recovered Naltrexone (mg) |
|---|---|---|---|
| Small IR Tablet | Naltrexone HCl | 3 | 6.11 |
| | | 6 | 7.60 |
| Small ER Tablet | | 3 | 1.60 |
| | | 6 | 3.96 |
| Large ER Tablet | | 3 | 4.01 |
| | | 6 | N/A* |
| Small Capsule (empty) | | 3 | 0.48 |
| | | 6 | 0.72 |
| Large Capsule (empty) | | 3 | 1.40 |
| | | 6 | 1.83 |

*Insufficient spiked solution to complete the experiment b. Naltrexone Recovered from Large ER Tablets and Filled Capsules This experiment was repeated for large ER tablets and both sizes of capsules. The ER tablets were not completed in the initial experiment due to an insufficient amount of spiking solution. The capsules were previously tested empty; in the repeat experiment, capsules were filled with crushed lactose pills to investigate effect of filling.

Ten (10) small IR tablets (Homeopathy Blank 5 Grain, Lactose, Lot #: 07090710H3, Exp. 08/23) were ground with a mortar and pestle and used to fill four (4) small capsules (Gelatin, Lot #: XT0702018, Exp. 08/21), and four (4) large capsules (Gelatin, Lot #: C1800166792, Exp. 01/23) for testing. Eight (8) large ER tablets (Mucus Relief Guaifenesin Extended-Release Tablets, 1200 mg, Lot #: F08474, Exp. 05/20) were also obtained for testing. Weights for 2-4 of the large ER tablets were obtained. The filled capsules were distributed to test tubes and large ER tablets were put into small scintillation vials. Each tablet and filled capsule was covered with a 25 mg/mL Naltrexone solution. After 3 minutes, two (2) of each sample type (large ER tablets, small capsules and large capsules) were removed from solution and an assay was performed for Naltrexone. This procedure was repeated at six (6) minutes. At six (6) hours, two (2) large ER tablets were removed from solution, gently rinsed with water and patted dry. Weight of the tablets was obtained and an assay for Naltrexone was performed. The remaining two (2) large ER tablets were reserved for observation after 8 hours of exposure to Naltrexone solution.

Results are shown in Table 7. Filled capsules did not show significant improvement in recovery of Naltrexone compared to empty. The Naltrexone recovered from large ER tablets increased with longer contact time. At the 6 hour time point, some amount of the outer layer of the large ER tablets was dissolved and washed away, which accounts for the lower amount of recovered Naltrexone. After 8 hours, the large ER tablets remained largely intact. Approximately 30-50% of the outermost layer had dissolved in solution and what remained had become a gelatinous consistency.

TABLE 7

Recovered Naltrexone from large ER tablets and filled capsules

| Dosage Form | API | Time | Recovered Naltrexone (mg) |
|---|---|---|---|
| Large ER Tablet | Naltrexone HCl | 3 min | 3.474 |
| | | 6 min | 4.681 |
| | | 6 hour | 2547 |
| Small Capsule (filled) | | 3 min | 0.546 |
| | | 6 min | 0.630 |
| Large Capsule (filled) | | 3 min | 2.109 |
| | | 6 min | 2.848 |

Example 6 a. Exposure Time to Ethanol/Water Solution to Render Medication Unusable

To determine the approximate time of exposure to an ethanol/water solution to make a tablet or capsule unusable, two (2) of each of small IR tablets (Homeopathy Blank 5 Grain, Lactose, Lot #: 07090710H3, Exp. 08/23), small ER tablets (Mucus Relief Guaifenesin Extended-Release Tablets, 600 mg, Lot #: F07210, Exp. 04/20), large ER tablets (Mucus Relief Guaifenesin Extended-Release Tablets, 1200 mg, Lot #: F08474, Exp. 05/20), small capsules (Gelatin, Lot #: XT0702018, Exp. 08/21), and large capsules (Gelatin, Lot #: C1800166792, Exp. 01/23) were obtained.

Small IR tablets and capsules were distributed to test tubes and covered with solution of 60% Ethanol/40% water without naltrexone. Samples were observed at periodic intervals beginning at 20 minutes. Observations and time for complete destruction of tablet or capsule were recorded.

ER tablets were distributed to test tubes or small scintillation vials (depending on size of the tablet) and covered with a 25 mg/mL Naltrexone spiking solution in 60% Ethanol/40% water. Samples were observed a minimum of 3 times, beginning at 1 hr and lasting until 24 hrs or until tablet was determined to be unusable. Any ER tablets intact after 24 hours were to be assayed for Naltrexone.

Observations are summarized in Tables 8 and 9. Naltrexone assay was not performed on remaining small and large ER tablets because spiking solution had all been absorbed and created a gelatinous mass.

TABLE 8

Observations-time for destruction of small IR tablets and capsules in ethanol/water solution

| Dosage Form | Time | Destruction Observation |
|---|---|---|
| Small IR Tablet #1 | 30 min | Completely destroyed, no sign of tablet shape or form after 20 min. Loose powder at bottom of tube |
| Small IR Tablet #2 | | Completely destroyed, no sign of tablet shape or form after 20 min. Loose powder at bottom of tube |
| Small IR Tablet #1 | 60 min | Completely destroyed, no sign of tablet shape or form after 20 min. Loose powder at bottom of tube |

TABLE 8-continued

Observations-time for destruction of small IR tablets and capsules in ethanol/water solution

| Dosage Form | Time | Destruction Observation |
|---|---|---|
| Small IR Tablet #2 | | Completely destroyed, no sign of tablet shape or form after 20 min. Loose powder at bottom of tube |
| Small IR Tablet #1 | Overnight and 24 hrs | Completely destroyed, no sign of tablet shape or form after 20 min. Loose powder at bottom of tube |
| Small IR Tablet #2 | | Completely destroyed, no sign of tablet shape or form after 20 min. Loose powder at bottom of tube |
| Small Capsule #1 | 30 min | Capsule intact and shape remains |
| Small Capsule #2 | | Capsule intact and shape remains |
| Small Capsule #1 | 60 min | Capsule intact; ends of capsule beginning to deform |
| Small Capsule #2 | | Capsule intact; ends of capsule beginning to deform |
| Small Capsule #1 | Overnight | Capsule deforming and collapsing; no absorption of solution |
| Small Capsule #2 | and 24 hrs | Capsule deforming and collapsing; no absorption of solution |
| Large Capsule #1 | 30 min | Capsule intact and shape remains |
| Large Capsule #2 | | Capsule intact and shape remains |
| Large Capsule #1 | 60 min | Capsule intact; ends of capsule beginning to deform |
| Large Capsule #2 | | Capsule intact; ends of capsule beginning to deform |
| Large Capsule #1 | Overnight | Capsule deforming and collapsing; no absorption of solution |
| Large Capsule #2 | and 24 hrs | Capsule deforming and collapsing; no absorption of solution |

TABLE 9

Observations-time for destruction of ER tablets in Naltrexone solution

| Dosage Form | Time | Destruction Observation |
|---|---|---|
| Small ER Tablet #1 | 1 hr | Beginning to dissolve; solution is blue |
| Small ER Tablet #2 | | Beginning to dissolve; solution is blue |
| Small ER Tablet #1 | Overnight | Gelatinous mass; all solution absorbed |
| Small ER Tablet #2 | | Gelatinous mass; all solution absorbed |
| Small ER Tablet #1 | 24 hrs | Gelatinous mass; all solution absorbed |
| Small ER Tablet #2 | | Gelatinous mass; all solution absorbed |
| Large ER Tablet #1 | 1 hr | No change; tablet intact |
| Large ER Tablet #2 | | No change; tablet intact |
| Large ER Tablet #1 | Overnight | Gelatinous mass; all solution absorbed |
| Large ER Tablet #2 | | Gelatinous mass; all solution absorbed |
| Large ER Tablet #1 | 24 hrs | Gelatinous mass; all solution absorbed |
| Large ER Tablet #2 | | Gelatinous mass; all solution absorbed | b. Destruction Potential of Capsules in Differing Ratios of Ethanol/Water

To identify the rate of swelling and destruction potential of capsules in differing ratios of ethanol/water in the formulations, large empty capsules were obtained. The capsules were tested in triplicate in 60% Ethanol/40% water, 50% Ethanol/50% water, and 30% Ethanol/70% water over a period of 5 hours. Each ratio of solution was tested at a volume of 1 mL, 2 mL and 4 mL added to three caplets per ratio of Ethanol/water. Capsules were placed in test tubes where 1 mL of solution covered approximately ⅔ of a large capsule. Observations were made starting 2 minutes after solution was added to each capsule Results, shown in Table 10, provide that the greatest effect on disintegration rate was the amount of purified water in the solution added. The solution containing the highest ratio of water (30% Ethanol/70% water) resulted in collapse or destruction of the capsules starting in about 1-2 hours and all of the solution was absorbed after 3 hours. The solution with the least amount of purified water (60% Ethanol/40% water) did not begin to soften or cause destruction to the capsules to a point of collapse until about 4 hours. Secondary observations are that most of the solution was not absorbed, and varying volumes of the solution did not appear to affect the disintegration rate (data not shown).

TABLE 10

Observations-Destruction of large capsules in Ethanol/water ratio formulations.

a. 60% Ethanol/40% Purified water solution (1 mL) added to large capsules
60:40 Ethanol:Purified Water-10 mL added to large capsules (covers approx. 2/3 capsule)

| Observation Time Point | Capsule #1 | Capsule #2 | Capsule #3 |
|---|---|---|---|
| 2 min | No change | | |
| 6 min | No change | | |
| 30 min | Softening-some deforming when pressure applied (can push in ~1/4) returns to shape when pressure removed | | |
| 1 hour | Pressure applied (can push in ~1/3) mostly returns to shape when pressure removed | | |
| 2 hour | No significant change from 1 hour | | |
| 3 hour | No significant change from 1 hour | | |
| 4 hour | No significant change from 1 hour | | |
| 5 hour | No significant change from 1 hour | | |
| 1 hour | Pressure applied (can push in ~1/3) mostly returns to shape when pressure removed | | |

TABLE 10-continued

Observations-Destruction of large capsules in Ethanol/water ratio formulations.

| | | | |
|---|---|---|---|
| 2 hour | No significant change from 1 hour | | |
| 3 hour | No significant change from 1 hour | | |
| 4 hour | Collapsed-prior puncture | Collapsing | Collapsing |
| 5 hour | No significant change from 1 hour | | | b. 50% Ethanol/50% purified water solution (1 mL) added to large capsules
50:50 Ethanol:Purified Water-1 mL added to large capsules (covers aporoximately 2/3 capsule)

| Observation Time Point | Capsule #1 | Capsule #2 | Capsule #3 |
|---|---|---|---|
| 2 minutes | No change | | |
| 6 minutes | No change | | |
| 30 minutes | Submerged part of capsule softened, pressure applied will deform but bounces back when pressure removed | | |
| 1 hour | Pressure applied and capsule deforms, pressure removed and mostly returns to shape but deflating | | |
| 2 hour | Collapsed when pressure added and does not return shape | | |
| 3 hour | Completely collapsed | | |
| 4 hour | No change | | |
| 5 hour | Most solution absorbed | Some solution absorbed | Some solution absorbed | c. 30% Ethanol/70% purified water solution (1 mL) added to large capsules
30:70 Ethanol:Purified Water-1 mL added to large capsules (covers approximately 2/3 capsule)

| Observation Time Point | Capsule #1 | Capsule #2 | Capsule #3 |
|---|---|---|---|
| 2 minutes | No change | | |
| 6 minutes | Capsule bottom (fully submerged end) softening-will dimple if pressure applied | | |
| 30 minutes | Entire capsule softened-applying pressure collapses capsule, does not return to shape when pressure removed | | |
| 1 hour | Completely collapsed, not dissolved | | |
| 2 hour | Breaks apart if poked with disposable pipette | | |
| 3 hour | Most of solution absorbed | | |
| 4 hour | No change | | |
| 5 hour | No change | | |

Example 7: Exposure Time to Solution with Hydroxpropyl Cellulose to Render Medication Unusable To determine the approximate time needed to make tablets and capsules unusable after exposure to an enhanced formulation of Ethanol and Water containing 0.3% Hydroxpropyl Cellulose with added yellow color dye, two (2) of each of small IR tablet (Homeopathy Blank 5 Grain, Lactose, Lot #: 07090710H3, Exp. 08/23), small ER tablet (Mucus Relief Guaifenesin to Extended-Release Tablets, 600 mg, Lot #: F07210, Exp. 04/20), large ER tablet (Mucus Relief Guaifenesin Extended-Release Tablets, 1200 mg, Lot #: F08474, Exp. 05/20), small capsule (Gelatin, Lot #: XT0702018, Exp. 08/21), and large capsule (Gelatin, Lot #: C1800166792, Exp. 01/23) were individually distributed into test tubes or small scintillation vials and covered with the enhanced solution containing 60% Ethanol/40% water and 0.3% Hydroxpropyl Cellulose. The tablets and capsules were observed a minimum of 3 times beginning at 1 hr and lasting until 24 hrs or until medication was determined to be unusable.

Results are summarized in Table 11, and show that all IR tablets were completely disintegrated after overnight exposure to the 60% Ethanol/40% water solution with 0.3% Hydroxpropyl Cellulose. ER tablets tested remained intact but were deemed unusable due to the formation of a gelatinous outer layer. Capsules tested were deformed but remained mostly intact. There was no significant absorption of the yellow color.

TABLE 11

Small IR Tablet, Small/Large ER Tablets and Capsules - Observations

| Dosage Form | Time | Destruction Observation |
|---|---|---|
| Small IR Tablet #1 | 1 hr. | Absorbing solution, expanding/cracking, maintaining shape |
| Small IR Tablet #2 | | Absorbing solution, expanding/cracking, maintaining shape |
| Small IR Tablet #1 | Overnight | Disintegrated and suspended in solution, Handling will cause complete destruction |
| Small IR Tablet #2 | | Disintegrated and suspended in solution, Handling will cause complete destruction |
| Small IR Tablet #1 | 24 hrs. | Same as overnight observation |
| Small IR Tablet #2 | | Same as overnight observation |
| Small ER Tablet #1 | 1 hr. | Slight removal of outer layer, tablet in-tact |
| Small ER Tablet #2 | | Slight removal of outer layer, tablet in-tact |
| Small ER Tablet #1 | Overnight | Gelatinous mass and all solution absorbed |
| Small ER Tablet #2 | | Gelatinous mass and all solution absorbed |

TABLE 11-continued

Small IR Tablet, Small/Large ER Tablets and Capsules - Observations

| Dosage Form | Time | Destruction Observation |
|---|---|---|
| Small ER Tablet #1 | 24 hrs. | Same as overnight observation |
| Small ER Tablet #2 | | Same as overnight observation |
| Large ER Tablet #1 | 1 hr. | No change |
| Large ER Tablet #2 | | No change |
| Large ER Tablet #1 | Overnight | Gelatinous mass and all solution absorbed |
| Large ER Tablet #2 | | Gelatinous mass and all solution absorbed |
| Large ER Tablet #1 | 24 hrs. | Same as overnight observation |
| Large ER Tablet #2 | | Same as overnight observation |
| Small Capsule #1 | 1 hr. | Capsule intact, ends of capsules beginning to deform |
| Small Capsule #2 | | Capsule intact, ends of capsules beginning to deform |
| Small Capsule #1 | Overnight | Softened, bloated and deforming |
| Small Capsule #2 | | Softened, bloated and deforming |
| Small Capsule #1 | 24 hrs. | Same as overnight observation |
| Small Capsule #2 | | Same as overnight observation |
| Large Capsule #1 | 1 hr. | Capsule intact |
| Large Capsule #2 | | Capsule intact |
| Large Capsule #1 | Overnight | Softened, maintains shape in tube but will deform when manipulated |
| Large Capsule #2 | | Softened, maintains shape in tube but will deform when manipulated |
| Large Capsule #1 | 24 hrs. | Same as overnight observation |
| Large Capsule #2 | | Same as overnight observation |

What is claimed is:

1. A device for deterring drug abuse, the device comprising:
    a housing configured to contain a drug that may be accessed through an access port located on a lid attached to the housing;
    a rotatable portion of the housing or the lid which is capable of rotating a carousel, or rotating relative to a carousel, when in an unsecured position;
    a locking mechanism coupled with the rotatable portion of the housing or the lid, the locking mechanism having a locked mode, wherein the rotatable portion of the housing or the lid is not normally able to move from a secure position;
    the locking mechanism further coupled with a piston;
    the device being configured such that attempts to improperly access the drug:
        a. when the rotatable portion of the housing or the lid is in the secure position, and
        b. when the locking mechanism is in the locked mode, move the piston and activate the release of a deterrent substance to the drug.

2. The device of claim 1, wherein the deterrent substance comprises one or more of a drug antagonist, a chemical irritant, a gelling agent, a colorant, an emetic, or an encapsulating agent.

3. The device of claim 1, wherein the locking mechanism is coupled to a timer, the locking mechanism locking after a predefined time.

4. The device of claim 1, wherein the locking mechanism is coupled to a dosage counter, the locking mechanism locking after a predefined dosage has been released from the housing.

5. The device of claim 1, further comprising a physical deterrent that is part of the housing.

6. The device of claim 1, further comprising a physical deterrent that is external to the housing.

7. The device of claim 1, wherein cutting a wall of the housing activates the piston, crushing the drug and releasing the deterrent substance into the space holding the drug.

8. The device of claim 1, wherein the housing has hollow walls under negative pressure.

* * * * *